United States Patent [19]

Muenster et al.

[11] Patent Number: 5,258,357
[45] Date of Patent: Nov. 2, 1993

[54] CARBOXAMIDES, THEIR PREPARATION AND THEIR USE AS HERBICIDES

[75] Inventors: Peter Muenster, Neulussheim; Gerd Steiner, Kirchheim; Wolfgang Freund, Neustadt; Bruno Wuerzer, Otterstadt; Karl-Otto Westphalen, Speyer, all of Fed. Rep. of Germany

[73] Assignee: BASF Aktiengesellschaft, Ludwigshafen, Fed. Rep. of Germany

[21] Appl. No.: 947,538

[22] Filed: Sep. 21, 1992

Related U.S. Application Data

[63] Continuation of Ser. No. 592,287, Oct. 3, 1990, Pat. No. 5,201,934.

[30] Foreign Application Priority Data

Oct. 7, 1989 [DE] Fed. Rep. of Germany ....... 3933573

[51] Int. Cl.$^5$ .................... A01N 43/08; A01N 57/08; C07D 307/38
[52] U.S. Cl. .................... 504/193; 549/473; 549/474; 549/487; 546/283; 546/276; 546/275; 548/195; 548/204; 548/206; 548/214; 548/233; 548/236; 548/245; 548/246; 548/247; 548/406; 548/413; 548/517; 548/518; 548/950; 548/315.4; 548/365.7; 548/312.1; 548/314.7; 548/364.7; 548/313.1; 548/365.1; 548/312.4; 548/315.1; 504/196; 504/239; 504/251; 504/252; 504/253; 504/269; 504/270; 504/271; 504/275; 504/277; 504/280; 504/282; 504/283; 504/287; 504/289; 504/299
[58] Field of Search .................... 71/88, 95, 92, 90, 94, 71/91; 548/527; 549/60, 487, 473, 474; 504/193, 196, 289

Primary Examiner—C. Warren Ivy
Assistant Examiner—A. A. Owens
Attorney, Agent, or Firm—Keil & Weinkauf

[57] ABSTRACT

Carboxamides of the formulae Ia to Ic

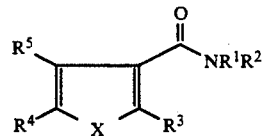

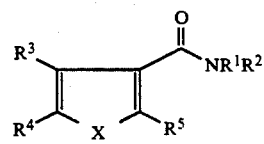

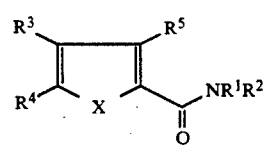

where
X is oxygen or sulfur;
$R^1$ is hydrogen or substituted or unsubstituted cycloalkyl or alkyl;
$R^2$ is hydroxy, alkoxy, cyanoalkyl, substituted or unsubstituted alkenyl, alkynyl, phenyl or naphthyl, a substituted or unsubstituted 5- to 6-membered heterocyclic structure or one of the groups stated for $R^1$, or
$R^1$ and $R^2$ together are a 4- to 7-membered chain which contains, in addition to methylene groups, one of the following groups as ring member: oxygen, sulfur, N-methyl or carbonyl;
$R^3$ and $R^4$ are each nitro, cyano, halogen, substituted or unsubstituted amino, alkoxy, alkylthio, a substituted or unsubstituted 5- to 6-membered heterocyclic structure, substituted or unsubstituted alkenyl, alkynyl, phenyl, phenoxy or phenylthio, or one of the groups stated for $R^1$;
$R^5$ is formyl, 4,5-dihydrooxazol-2-yl or COYR$^6$ (Y=O,S);
$R^6$ is hydrogen, cycloalkyl, substituted or unsubstituted alkyl, alkenyl, alkynyl, cycloalkenyl or phenyl, a 5- to 6-membered heterocyclic structure, phthalimido, tetrahydrophthalimido, succinimido, maleimido, benzotriazolyl or (Abstract continued on next page.)

a group $-N=CR^7R^8$, where
$R^7$ and $R^8$ are hydrogen or alkyl, and $R^8$ may also be cycloalkyl, phenyl, furyl or $R^7$ and $R^8$ together form a 4- to 7-membered alkylene chain;

and if $R^5$ is carboxyl, methoxycarbonyl or ethoxycarbonyl and $R^2$ is hydrogen, $R^3$ is not hydrogen and $R^4$ is not hydrogen or methyl, and if $R^5$ is carboxyl, methoxycarbonyl or ethoxycarbonyl and $R^4$ is hydrogen, $R^3$ is not hydrogen or $R^2$ is not one of the following groups: hydrogen; $C_1$-$C_4$-alkyl, phenyl; 2-(3,4-dimethoxyphenyl)ethyl or 2,5-dichlorothien-3-yl;

processes for the manufacture of compounds I and herbicidal agents containing them.

3 Claims, No Drawings

CARBOXAMIDES, THEIR PREPARATION AND THEIR USE AS HERBICIDES

This is a continuation of application Ser. No. 07/592,287, filed Oct. 3, 1990 now U.S. Pat. No. 5,201,934.

The present invention relates to carboxamides of the general formulae Ia, Ib and Ic

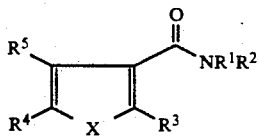   Ia

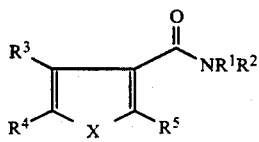   Ib

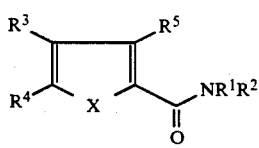   Ic where
X is oxygen or sulfur,
$R^1$ is hydrogen,
$C_3-C_8$-cycloalkyl which may carry from one to three of the following radicals: halogen, $C_1-C_4$-alkyl, $C_1-C_4$-haloalkyl, $C_1-C_4$-alkoxy and/or $C_1-C_4$-haloalkoxy,
$C_1-C_6$-alkyl which may carry from one to three of the following radicals:
hydroxyl, halogen, $C_3-C_8$-cycloalkyl, $C_1-C_4$-alkoxy, $C_1-C_4$-haloalkoxy, $C_1-C_4$-alkylthio, $C_1-C_4$-haloalkylthio, $C_1-C_4$-alkylamino, di-$C_1-C_4$-alkylamino and/or $C_3-C_6$-cycloalkylamino and/or a radical

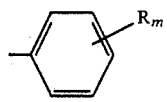

where
is cyano, nitro, halogen, $C_1-C_4$-alkyl, $C_1-C_4$-haloalkyl, $C_1-C_4$-alkoxy, $C_1-C_4$-haloalkoxy, $C_1-C_4$-alkylthio, $C_2-C_4$-alkynyloxy, $C_1-C_4$-haloalkylthio, $C_3-C_6$-alkoxycarbonylalkoxy and/or $C_1-C_4$-alkoxycarbonyl and
m is 0, 1, 2 or 3, and the radicals R may be different when m is 2 or 3,
$R^2$ is hydroxyl, $C_1-C_4$-alkoxy, $C_1-C_6$-cyanoalkyl, $C_3-C_6$-alkenyl, $C_3-C_6$-alkynyl, phenyl or naphthyl, where these groups may carry from one to three of the radicals stated for R,
a 5-membered or 6-membered heterocyclic structure containing one or two heteroatoms selected from the group consisting of nitrogen, oxygen and sulfur, where this ring may carry one or two of the following radicals: halogen, $C_1-C_4$-alkyl, $C_1-C_4$-haloalkyl, $C_1-C_4$-alkoxy, $C_1-C_4$-haloalkoxy and/or $C_1-C_4$-alkylthio, or
one of the groups stated for $R^1$, or $R^1$ and $R^2$ together form a 4-membered to 7-membered chain which, in addition to methylene groups, may contain one of the following groups as a ring member: oxygen, sulfur, N-methyl or carbonyl,
$R^3$ and $R^4$ are each nitro, cyano, halogen,
amino which may carry one or two $C_1-C_4$-alkyl groups and/or a $C_1-C_4$-alkylcarbonyl group,
$C_1-C_4$-alkoxy or $C_1-C_4$-alkylthio, where these groups may carry from one to nine halogen atoms,
a 5-membered or 6-membered heterocyclic structure containing one or two heteroatoms selected from the group consisting of oxygen, sulfur and nitrogen, where this ring may carry one or two of the following radicals: halogen, $C_1-C_4$-alkyl, $C_1-C_4$-haloalkyl, $C_1-C_4$-alkoxy, $C_1-C_4$-haloalkoxy and/or $C_1-C_4$-alkylthio,
$C_2-C_6$-alkenyl, $C_2-C_6$-alkynyl, phenyl, phenoxy or phenylthio, where these groups may carry from one to three of the radicals stated for R, or
one of the groups stated for $R^1$,
$R^5$ is formyl, 4,5-dihydrooxazol-2-yl or a group $COYR^6$,
Y is oxygen or sulfur,
$R^6$ is hydrogen,
$C_3-C_8$-cycloalkyl,
$C_1-C_6$-alkyl which may carry from one to five halogen atoms or hydroxyl groups and/or one of the following radicals: cyano, aminocarbonyl, carboxyl, trimethylsilyl, $C_1-C_4$-alkoxy, $C_1-C_4$-alkoxy-$C_1-C_4$-alkoxy, $C_1-C_4$-alkylthio, $C_1-C_4$-alkylamino, di-$C_1-C_4$-alkylamino, $C_1-C_4$-alkylsulfinyl, $C_1-C_4$-alkylsulfonyl, $C_1-C_4$-alkoxycarbonyl, $C_2-C_4$-alkoxycarbonyl-$C_1-C_3$-alkoxy, $C_2-C_4$-alkoxycarbonyl-$C_1-C_3$-alkoxycarbonyl, $C_1-C_4$-alkylaminocarbonyl, di-$C_1-C_4$-alkylaminocarbonyl, di-$C_1-C_4$-alkylphosphonyl, $C_1-C_4$-alkyliminoxy, phenyl, thienyl, benzyloxy, benzylthio, furyl, tetrahydrofuryl, phthalimido, pyridyl and/or benzoyl, where the cyclic radicals in turn may carry from one to three of the radicals stated for R,
$C_3-C_6$-alkenyl, $C_3-C_6$-alkynyl or $C_5-C_7$-cycloalkenyl, where these groups may carry one of the following radicals: hydroxyl, halogen, $C_1-C_4$-alkoxy or phenyl, and the phenyl radical in turn may carry from one to three of the radicals stated for R,
a 5-membered or 6-membered heterocyclic structure containing one or two heteroatoms selected from the group consisting of nitrogen, oxygen and sulfur,
phthalimido, tetrahydrophthalimido, succinimido, maleimido, benzotriazolyl,
phenyl which may carry from one to three of the radicals stated for R, or
a group $—N=CR^7R^8$ where
$R^7$ is hydrogen or $C_1-C_6$-alkyl and
$R^8$ is $C_3-C_6$-cycloalkyl, phenyl, furyl or a radical $R^7$ or
$R^7$ and $R^8$ together form a 4-membered to 7-membered alkylene chain, and if
$R^5$ is carboxyl, methoxycarbonyl or ethoxycarbonyl and $R^2$ is hydrogen, $R^3$ is not hydrogen or $R^4$ is not hydrogen or methyl, and if
$R^5$ is carboxyl, methoxycarbonyl or ethoxycarbonyl and $R^4$ is hydrogen, $R^3$ is not hydrogen or $R^2$ is not one of the following groups: hydrogen, $C_1-C_4$-alkyl, phenyl, 2-(3,4-dimethoxyphenyl)ethyl or 2,5-dichlorothien-3-yl,
and their agriculturally suitable salts.

The present invention furthermore relates to a process for the preparation of the compounds Ia, Ib or Ic and herbicides containing one or more carboxamides Ia, Ib or Ic and/or a carboxamide of the general formula IA, IB or IC

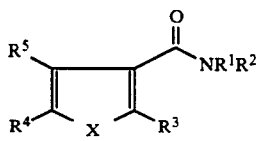

IA

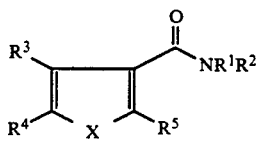

IB

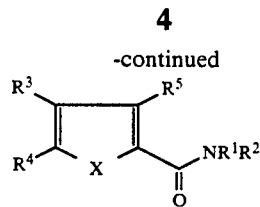

IC where the substituents have the meanings stated in claim 1 and in addition $R^5$ is carboxyl, methoxycarbonyl or ethoxycarbonyl and $R^2$ is hydrogen when $R^3$ is hydrogen or $R^4$ is not hydrogen or methyl, and $R^5$ is carboxyl, methoxycarbonyl or ethoxycarbonyl and $R^4$ is hydrogen when $R^3$ is hydrogen or $R^2$ is not one of the following groups: hydrogen, $C_1$–$C_4$-alkyl, phenyl, 2-(3,4-dimethoxyphenyl)ethyl or 2,5-dichlorothien-3-yl.

The literature discloses for example carboxamides of the following formulae I', I" and I''':

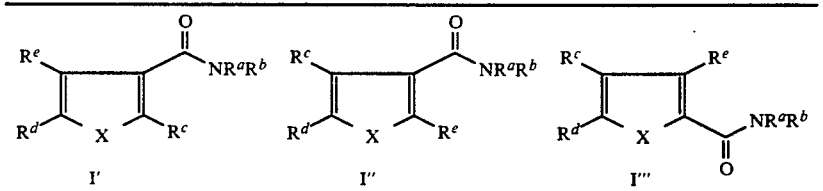

| Formula | X | $R^a$ | $R^b$ | $R^c$ | $R^d$ | $R^3$ | Reference |
|---|---|---|---|---|---|---|---|
| I' | O | H | H | H | CH$_3$ | CO$_2$CH$_3$ | 1. |
| I' | O | H | H | H | H | CO$_2$H | 1. |
| I' | O | H | H | H | H | CO$_2$CH$_2$CH$_3$ | 2. |
| I' | O | H | (CH$_2$)$_2$–C$_6$H$_3$(OCH$_3$)$_2$ | H | H | CO$_2$H | 3. |
| I' | O | H | (CH$_2$)$_2$–C$_6$H$_3$(OCH$_3$)$_2$ | H | H | CO$_2$CH$_2$CH$_3$ | 3. |
| I' | O | H | H | H | CH$_3$ | CO$_2$CH$_2$CH$_3$ | 4. |
| I' | S | H | 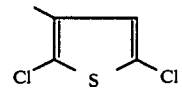 | H | H | CO$_2$H | 5. |
| I' | S | H | –C$_6$H$_5$ | H | H | 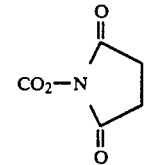 | 5. |
| I' | S | H | –C$_6$H$_5$ | H | H | CO$_2$H | 5. |
| I" | O | H | H | H | H | CO$_2$H | 1. |
| I" | O | H | H | H | H | CO$_2$CH$_2$CH$_3$ | 6. |
| I" | S | H | H | H | H | CHO | 7. |
| I" | S | CH$_3$ | –C$_6$H$_5$ | H | H | CO$_2$CH$_3$ | 8. |
| I" | S | CH$_3$ | –C$_6$H$_5$ | H | H | CO$_2$H | 8. |
| I" | S | H | H | H | H | CO$_2$H | 9. |
| I''' | O | H | –C$_6$H$_5$ | H | H | CO$_2$H | 10. |
| I''' | O | H | H | CH$_3$ | H | CO$_2$H | 11. |
| I''' | O | H | C(CH$_3$)$_3$ | H | H | CO$_2$H | 12. |

-continued

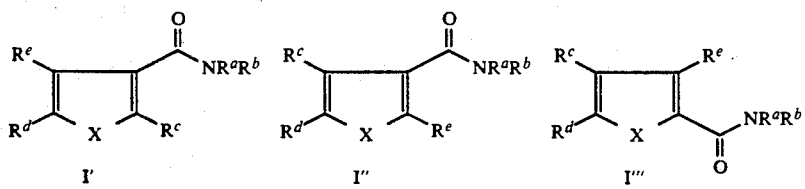

| Formula | X | $R^a$ | $R^b$ | $R^c$ | $R^d$ | $R^3$ | Reference |
|---|---|---|---|---|---|---|---|
| I''' | S | H | H | H | H | CHO | 7b. |
| I''' | S | CH$_3$ | —C$_6$H$_5$ | H | H | CO$_2$CH$_3$ | 8. |
| I''' | S | CH$_3$ | —C$_6$H$_5$ | H | H | CO$_2$H | 8. |
| I''' | S | H | H | H | H | CO$_2$H | 9. |
| I''' | S | H | CH$_2$CH$_3$ | H | H | CO$_2$H | 12. |
| I''' | S | H | C(CH$_3$)$_3$ | H | H | CHO | 12. |
| I''' | S | H | C(CH$_3$)$_3$ | H | H | CO$_2$H | 12. |

References:
1. Bull. Soc. Chim. Fr., 1970, 1445
2. Rocz. Chem., 38, 511 (1964)
3. DE-A-31 43 876
4. C.R. Acad. Sci., Ser. C, 268 (1969), 1884
5. DE-A 35 24 743
6. J. Am. Chem. Soc., 77 (1955), 4069
7a. Bull. Soc. Chim. Fr, 1976, 628
7b. Acad. Sci., Ser. C, 276 (1973), 871
8. J. Orq. Chem., 189 (1953), 138
9. J. Chem. Soc., 1937, 911
10. Acta Polytochim., 2 (1924/26), 19
11. Helv. Chim. Acta, 14 (1931), 1270
12. J. Org. Chem., 50 (1985), 4362.

It is an object of the present invention to provide novel herbicidal substances.

We have found that this object is achieved by the carboxamides Ia, Ib and Ic defined at the outset and processes for their preparation.

We have also found that the carboxamides Ia, Ib and Ic as well as the carboxamides IA, IB and IC are suitable for controlling undesirable plant growth.

The novel carboxamides Ia, Ib and Ic can be prepared by various methods. They are obtained, for example, by the following processes.

1. Process for the preparation of the compounds Ia in which $R^5$ is carboxyl:

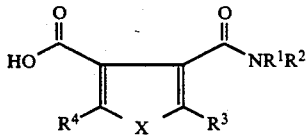

These carboxamides are obtained by converting a corresponding dicarboxylic anhydride of formula II in a conventional manner into an amine of the formula III.

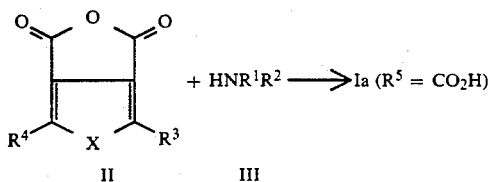

The action is carried out, as a rule, at from $-10°$ to $100°$ C., preferably from $0°$ to $30°$ C., in an inert organic solvent.

Suitable solvents are ethers, such as methyl tert-butyl ether, 1,2-dimethoxyethane, diethylene glycol dimethyl ether, tetrahydrofuran and dioxane.

The concentration of the educts in the solvent is is general from 0.1 to 5, preferably from 0.2 to 2, mol/l.

The molar ratio of II to III is in general from 1:5 to 1:1, preferably from 1:2 to 1:1.

The required dicarboxylic anhydrides II are known or can be prepared in a conventional manner by reacting the corresponding dicarboxylic acids with the anhydride of a lower carboxylic acid, in particular acetic anhydride.

2. Process for the preparation of the compounds Ia, Ib and Ic in which $R^3$ and $R^4$ are not bromine or iodine and $R^5$ is formyl or carboxyl:

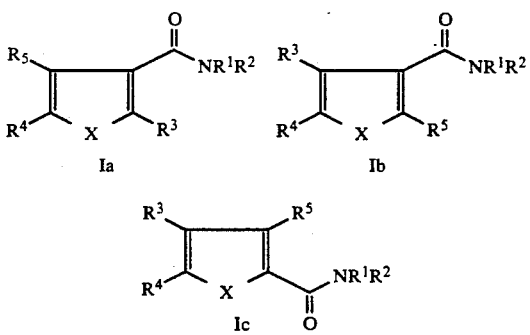

($R^3$ and $R^4 \neq$ Br or I; $R^5$ = CHO or CO$_2$H)

These compounds Ia, Ib and Ic are obtained by converting a corresponding carboxylic acid of the formula IVa, IVb or IVc in a conventional manner into the halide or another activated form of the carboxylic acid, then reacting these derivatives with an amine of the formula III and thereafter reacting the resulting carboxamide Va, Vb or Vc with a formylating or carboxylating reagent in the presence of a base.

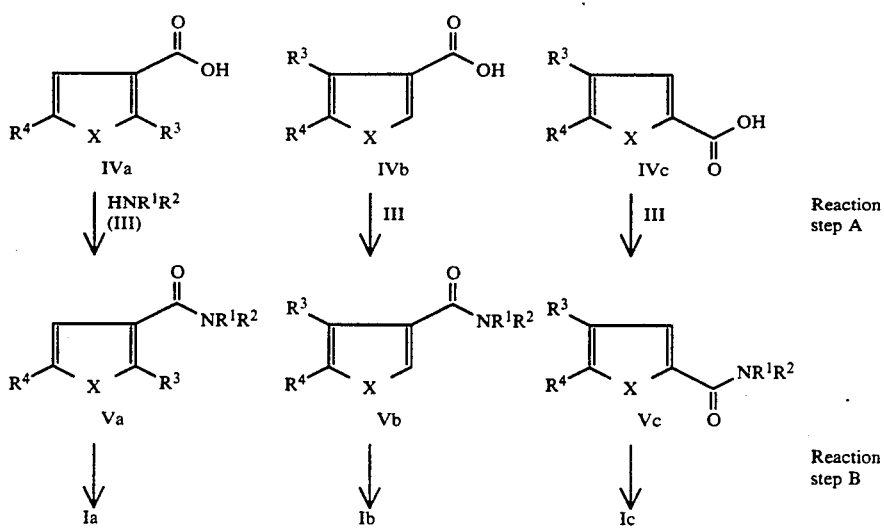

($R^3$ and $R^4 \neq$ Br or I; $R^5$ = CHO or $CO_2H$)

The individual reaction steps of this synthesis sequence can be carried out in general as follows:

Reaction step A:

The compounds Va, Vb or Vc are obtained from the acids IVa, IVb and IVc by first converting IVa, IVb or IVc in a conventional manner into the halide or another activated form of the carboxylic acid function and then amidating these derivatives with an amine III.

In addition to halides, in particular the chlorides and the bromides, other activated forms of the carboxylic acid are, for example, imidazolides. In general, the halides are preferred.

They are obtained by reacting the carboxylic acids IVa, IVb or IVc with an halogenating agent, such as thionyl chloride, thionyl bromide, phosphorus oxychloride or -bromide, phosphorus tri- and pentachloride or -bromide, phosgene and elemental chlorine and bromine.

The halogenating agent is used in an amount of from 1 to 5, preferably from 1 to 2, mole equivalents.

The reaction takes place at from 20° C. to the boiling point of the halogenating agent or, if the reaction is carried out in the presence of an inert organic solvent, to the boiling point of the latter.

Examples of suitable solvents are hydrocarbons and halohydrocarbons, such as benzene, toluene and dichloromethane.

The activated carboxylic acid derivatives are usually isolated, for example by distilling off the halogenating agent and, where present, the solvent, before being reacted with the amines III.

In this case, the amidation is carried out at from −20° to 50° C., preferably from 0° to 30° C., in an inert aprotic polar organic solvent.

Halohydrocarbons, such as dichloromethane and ethers, such as diethyl ether and tert-butyl methyl ether, are particularly suitable solvents for this reaction.

Since hydrogen halide is formed in the amidation of acyl halides, it is advisable to add the amine III in an excess of from 2 to 5 and preferably 2 to 3, mole equivalents. If the amine is used in equimolar amounts (from 1 to 1.2 mole equivalents), a base, in particular a tertiary amine, such as triethylamine or pyridine, should be added to bind the hydrogen halide.

Reaction step B:

The formylation or carboxylation of the carboxamides Va or Vb or Vc is carried out, as a rule, at from −100° to −20° C., preferably from −80° to −40° C., in an aprotic polar inert organic solvent in the absence of moisture and in the presence of a base.

In particular, dimethylformamide and N-formylmorpholine are used as formylating reagents, a preferred carboxylating agent being carbon dioxide.

Particularly suitable solvents are diethyl ether, tert-butyl methyl ether, tetrahydrofuran and dioxane.

Preferably used bases are alkali metal hydrocarbons, such as methyllithium, n-butyllithium, tert-butyllithium and phenyllithium.

The reaction is usually carried out in such a way that from 1.3 to 2.5 mole equivalents of the dissolved base are first added to the carboxamide Va or Vb to give a carboxamide derivative which is metalized in the ring, said derivative reacting to give the desired product Ia, Ib or Ic on subsequent addition of the electrophilic formylating or carboxylating reagent.

Since, where $R^1$ or $R^2$ is H, the first mole equivalent base merely deprotonates the amide nitrogen, in this case less than 2 mole equivalents of base are required to metalize the heterocycle; in this case, the reaction is preferably carried out in the presence of from 2 to 2.5 mole equivalents of the base.

The carboxylic acids IVa, IVb and IVc required for this process are known from the literature or can be prepared by general methods known from the literature, for example by oxidation of the corresponding alcohols or aldehydes or by hydrolysis of the corresponding nitriles (Beilstein, main section and 1st to 5th supplements, Volume 18, The Chemistry of Heterocyclic Compounds, Interscience Publishers, New York, 1976, John Wiley & Sons, Inc., 1988, Vol. 44, Part I-III).

3. Process for the preparation of the compounds Ib and Ic in which $R^3$ or $R^4$ is halogen, $R^5$ is $CO_2R^6$ and $R^6$ is alkyl:

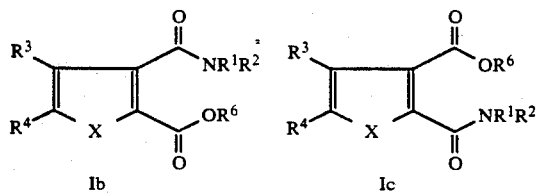

($R^3$ or $R^4$ = halogen; $R^6$ = alkyl)

These compounds Ib and Ic are obtained by a method in which a dicarboxylic diester of the general formula VIa or VIb is first diazotized in a conventional manner and the diazotized compound is converted with an inorganic halide into the corresponding derivative VIIa or VIIb, VIIa or VIIb is then amidated with an amine of the formula III and the resulting mixture of the isomeric compounds Ib and Ic is separated into the individual components.

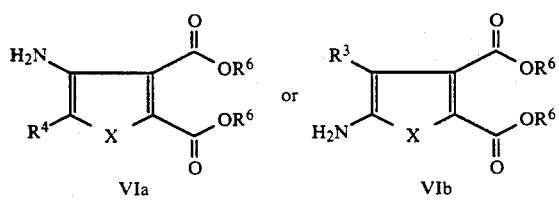

Reaction step A

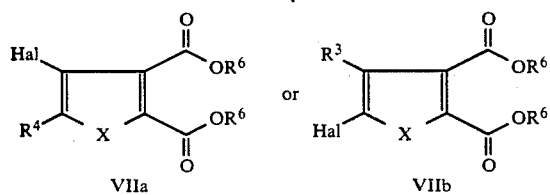

Reaction step B

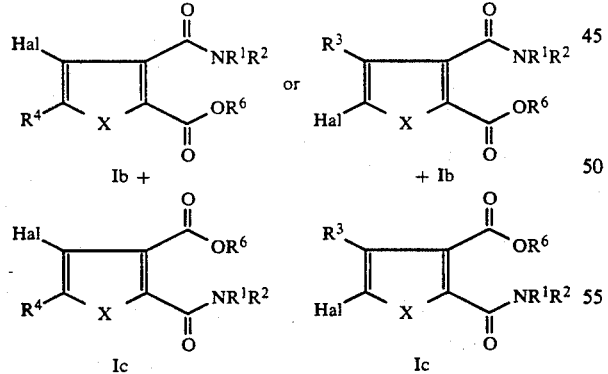

In formulae VIIa, VIIb, Ib and Ic, Hal is halogen, such as fluorine, chlorine, bromine or iodine.

The reaction steps of this synthesis sequence can be carried out in general as follows:

Reaction step A:

The diazotization of the dicarboxylic ester of the general formula VIa or IVb is carried out, as a rule, at from −20° to +20° C., preferably from −5° to +10° C., in a mineral acid, in particular hydrochloric acid, in the presence of an alkali metal nitrite, such as sodium nitrite.

The diazonium salt thus obtained is then reacted in situ with from 1 to 5, preferably from 1.5 to 2.5, moles of an inorganic halide, in particular a copper (I) halide.

The reaction conditions may be varied within the limits of the processes known for the Sandmeyer reaction (also see Houben-Weyl, Vol. X/3, pages 1–212 (1965); Chem. Zvesti 36 (1982), 401).

Reaction step B:

The reaction of the resulting dicarboxylic ester VIIa and VIIb with the amine III is carried out in general and in particular under conditions similar to those described in process 1.

However, solvents used in particular here are halohydrocarbons, such as methylene chloride, and ethers, such as diethyl ether, tert-butyl methyl ether and tetrahydrofuran.

The amine III is generally used in equimolar amounts or in excess, preferably in amounts of from 1 to 1.2 mole equivalents, based on VIIa or VIIb.

This process gives the isomeric carboxamides of the formulae Ib or Ic in different amounts. The isomeric mixture is separated either by fractional crystallization or by a chromatographic method.

Dicarboxylic diesters VIa and VIb required for this process are known or can be prepared from the corresponding oxo esters Xa, for example under conditions similar to those described in Synthesis, 1977, 200, in accordance with the following reaction scheme:

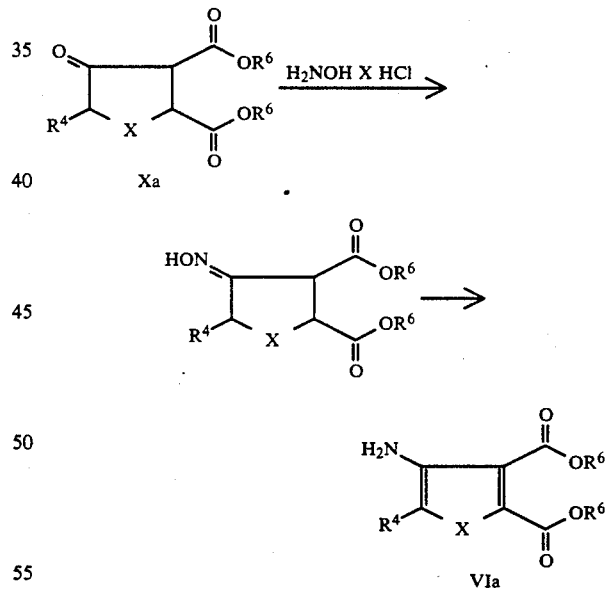

4. Process for the preparation of the compounds Ib and Ic in which $R^5$ is carboxyl:

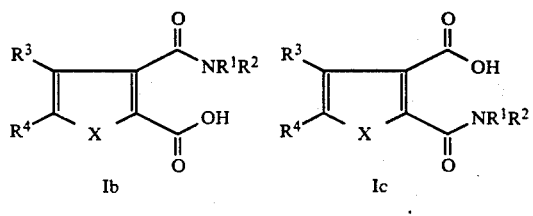

These carboxamides Ib and Ic are obtained, for example, by hydrolyzing a corresponding carboxamide of the formula Ib or Ic where $R^5$ is $CO_2R^6$ and $R^6$ is alkyl in a conventional manner with an aqueous base.

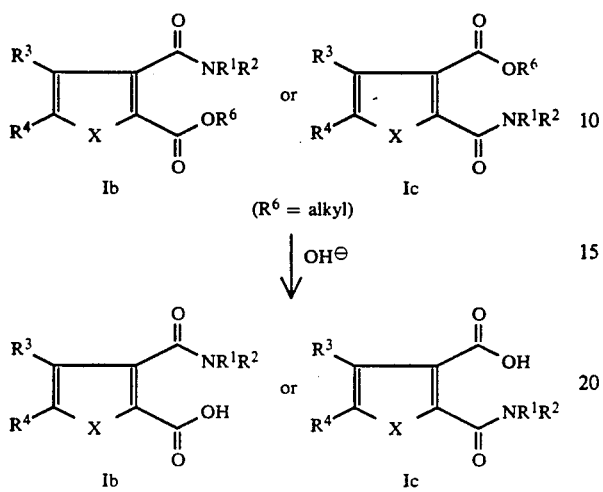

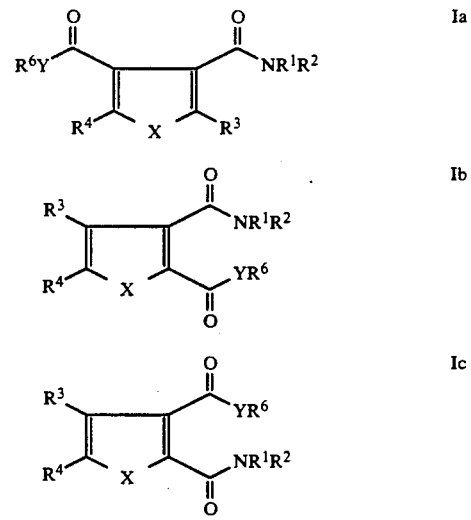

The reaction is carried out by a method in which a carboxamide Ib or Ic ($R^6$=alkyl) in an inert solvent is initially taken and is reacted with an aqueous base at from $-30°$ to $120°$ C., preferably from $-10°$ to $40°$ C. The carboxamides of the formula Ib or Ic ($R^5=CO_2H$) are then liberated at from $-30°$ to $100°$ C., preferably from $-10°$ to $10°$ C., by adding mineral acids.

Suitable solvents for this ester cleavage are alcohols, such as methanol, ethanol, propanol or ethylene glycol; the reaction is particularly preferably carried out in the alcohol corresponding to the ester component $R^6OH$. The concentration of the educt Ib or Ic is in general from 0.1 to 5.0, preferably from 0.2 to 2.0, mole/l.

Solutions of alkali metal or alkaline earth metal hydroxides, such as LiOH, NaOH, KOH, Ca(OH)$_2$ or Ba(OH)$_2$, preferably NaOH or KOH, are used as the aqueous base. The hydroxides are used in the form of a 5-20% strength aqueous solution.

The molar ratios in which esters Ib and Ic and hydroxides are used are from 1:0.95 to 1:1 for alkali metal hydroxides and from 1:0.48 to 1:0.55 for alkaline earth metal hydroxides.

5. Process for the preparation of the compounds Ia, Ib and Ic in which $R^5$ is $COYR^6$:

These compounds are obtained, for example, if a carboxamide Ia, Ib or Ic in which $R^5$ is $CO_2H$ is converted in a conventional manner into or an activated form of the carboxylic acid, and these derivatives are then esterified with a compound VIII.

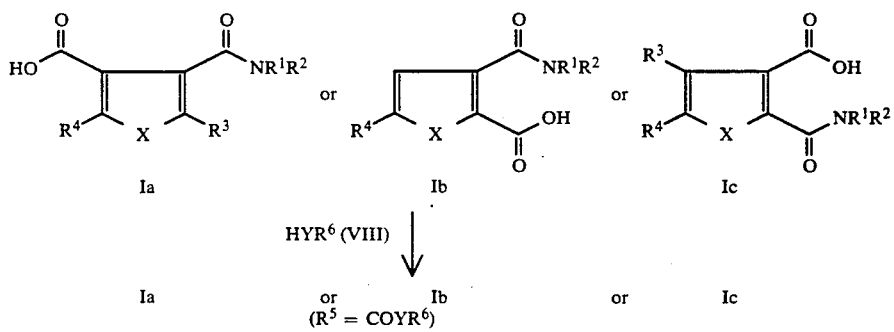

This reaction is usually carried out at from $-20°$ to $60°$ C., preferably from $0°$ to $40°$ C.

Advantageously used solvents are halohydrocarbons, such as chlorobenzene and 1,2-dichlorobenzene, ethers, e.g. methyl tert-butyl ether, 1,2-dimethoxyethane, diethylene glycol dimethyl ether, tetrahydrofuran and dioxane, dipolar aprotic solvents, e.g. acetonitrile, dimethylformamide, dimethylacetamide, dimethyl sulfoxide, N-methylpyrrolidone, 1,3-dimethyltetrahydro-2(1H)-pyrimidinone and 1,3-dimethylimidazolin-2-one, or aromatics, e.g. benzene, toluene and xylene. The concentration of the educts in the solvent is in general from 0.1 to 5.0, preferably from 0.2 to 2.0, mole/l.

As a rule, from 1 to 1.5, preferably from 1 to 1.15, mole equivalents, based on the carboxylic acid Ia, Ib or Ic ($R^5=CO_2H$), of the compound V are used.

Suitable dehydrating agents are diimides, such as dicyclohexylcarbodiimide (also see Angew. Chem. 90 (1978), 556) or anhydrides, such as propanephosphonic anhydride. The reaction also takes place in the presence of 1-methyl-2-halopyridinium iodides as dehydrating agents (cf. Chem. Lett., 1045 (1975); ibid., 13 (1976); ibid., 49 (1976)).

The reaction is particularly preferably carried out in an inert solvent, such as tetrahydrofuran, dichloromethane or toluene, in the presence of dicyclohexylcarbodiimide as a dehydrating agent with the use of the carboxylic acid I, the compound IV and the dehydrating agent in stoichiometric amounts at from 20° to 40° C.

The reaction is complete in general after 14 hours; the carboxamides Ia, Ib and Ic are isolated in a conventional manner (for example by diluting the reaction mixture with water and extracting the product with an organic solvent) and are purified by conventional standard methods, such as recrystallization or chromatography.

6. Process for the preparation of the compounds Ia, Ib and Ic in which $R^5$ is 4,5-dihydrooxazol-2-yl:

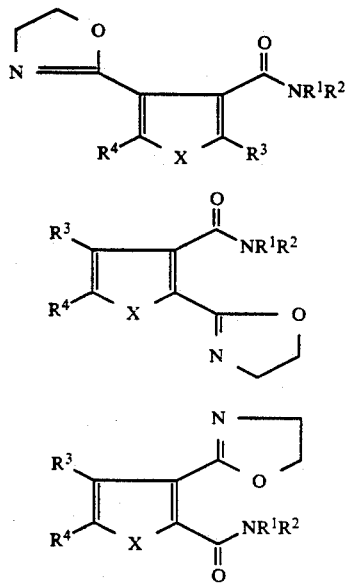

These compounds Ia, Ib and Ic are obtained, for example, by subjecting a corresponding dicarboxamide from Ia, Ib or Ic where $R^5$ is carboxyl to a cyclization reaction with 2-aminoethanol IX in a conventional manner. For the sake of clarity, this reaction is described below using a typical example for the compounds Ia.

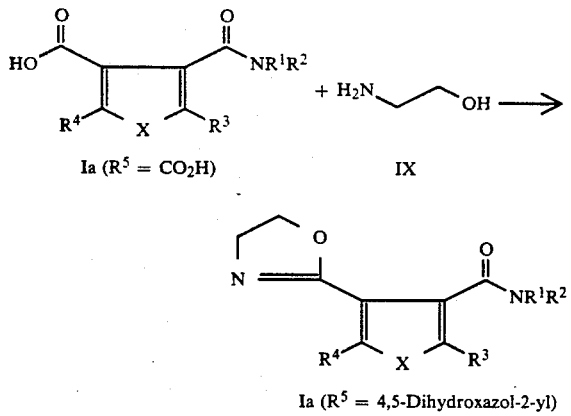

The reaction is carried out by a method in which the compounds are reacted with an amino alcohol IX in the presence or absence of an inert solvent at from 0° to 180° C., preferably at the reflux temperature of the mixture used. The ester or carboxylic acid Ia, Ib or Ic and amino alcohol IX are used in a ratio of from 1:1 to 1:2.5, preferably from 1:1 to 1:1.5.

Advantageously used solvents are halohydrocarbons, such as chlorobenzene and 1,2-dichlorobenzene, ethers, e.g. methyl tert-butyl ether, 1,2-dimethoxyethane, diethylene glycol dimethyl ether, tetrahydrofuran and dioxane; alcohols, such as methanol, ethanol, propanol or ethylene glycol, dipolar aprotic solvents, e.g. acetonitrile, dimethylformamide, dimethylacetamide, dimethyl sulfoxide, N-methylpyrrolidone, 1,3-dimethyltetrahydro-2(1H)-pyrimidinone and 1,3-dimethylimidazolin-2-one, or aromatics, e.g. benzene, toluene and xylene. The concentration of the educts in the solvents is in general from 0.1 to 5.0, preferably from 0.2 to 2.0, mole/l.

The reaction is complete in general after 14 hours; the carboxamides Ia and Ib are, if required, then precipitated by the addition of water, filtered off under suction or extracted with an organic solvent and purified by conventional standard methods, such as recrystallization or chromatography.

In addition to the processes described above for the preparation of compounds Ia, Ib and Ic, there are further possible syntheses, which are described in the following publications:

Beilstein, main section and 1st to 5th supplements, Volume 27; R. W. Wiley, The Chemistry of Heterocyclic Compounds, Five- and Six-Membered Compounds with Nitrogen and Oxygen, Interscience Publishers, New York, London (1962), Heterocyclic Chemistry, Vol. 6, Five-membered Rings with Two or More Oxygen, Sulfur or Nitrogen Atoms, Programon Press, 1984, J. March, Advanced Organic Chemistry, Third Edition, John Wiley and Sons, 1985, Houben-Weyl, Methoden der organischen Chemie, 4th edition, Thieme Verlag, Volumes IV, VI, VII, VIII and X.

In view of the intended use of the compounds IA, IB and IC, the following substituents are preferred: $R^1$ is hydrogen;

$C_3$-$C_8$-cycloalkyl, such as cyclopropyl, cyclobutyl, cyclopentyl, cyclohexyl, cycloheptyl or cyclooctyl, in particular cyclopropyl, cyclobutyl, cyclopentyl or cyclohexyl, which may carry from one to three of the following radicals: halogen, such as fluorine, chlorine, bromine or iodine, in particular fluorine or chlorine, alkyl, such as methyl, ethyl, propyl, 1-methylethyl, butyl, 1-methylpropyl, 2-methylpropyl or 1,1-dimethylethyl, in particular methyl or ethyl, haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl, in particular trifluoromethyl, alkoxy, such as methoxy, ethoxy, n-propoxy, 2-methylethoxy, n-butoxy, 1-methylpropoxy, 2-methylpropoxy or 1,1-dimethylethoxy, in particular methoxy or ethoxy, haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy;

Alkyl as stated above, and pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1- methylpropyl or 1-ethyl-2-methylpropyl, in particular methyl, ethyl, 1-methylethyl or 1,1-dimethylethyl, which may carry from one to three of the following radicals: hydroxyl, halogen as stated above, in particular fluorine or chlorine, cycloalkyl as stated above, in particular cyclopropyl, alkoxy as stated above, in particular methoxy or ethoxy, haloalkoxy as stated above, in particular trifluoromethoxy, alkylthio, such as methylthio, ethylthio, n-propylthio, 1-methylethylthio, n-butylthio, 1-methylpropylthio, 2-methylpropylthio or 1,1-dimethylethylthio, in particular methylthio or ethylthio, haloalkylthio, such as difluoromethylthio, trifluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dichloro-2-fluoroethylthio, 2,2,2-trichloroethylthio or pentafluoroethylthio, in particular trifluoromethylthio or pentafluoroethylthio, alkylamino, such as methylamino, ethylamino, propylamino or isopropylamino, in particular methylamino, dialkylamino, such as dimethylamino, diethylamino, dipropylamino, diisopropylamino or methylethylamino, in particular dimethylamino, and cycloalkylamino, such as cyclopropylamino, cyclobutylamino, cyclopentylamino or cyclohexylamino, in particular cyclopropylamino, and/or may carry a radical where R is cyano, nitro, halogen, in particular fluorine or chlorine, alkyl, in particular methyl, ethyl or 1-methylethyl, haloalkyl, in particular trifluoromethyl, alkoxy, in particular methoxy, ethoxy or 1-methylethoxy, haloalkoxy, in particular difluoromethoxy or trifluoromethoxy, alkynyloxy, such as propargyloxy, alkylthio, in particular methylthio or ethylthio, haloalkylthio, in particular difluoromethylthio or trifluoromethylthio, alkoxycarbonylalkoxy, in particular methoxy- or ethoxycarbonylmethoxy, and/or alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl, in particular methoxycarbonyl or ethoxycarbonyl, and m is 0, 1, 2 or 3, and the radicals R may be different when m is 2 or 3, $R^2$ is hydroxyl;

alkoxy, in particular methoxy or ethoxy;

cyanoalkyl, such as cyanomethyl, cyanobutyl or 2-cyano-3-methylbut-2-yl;

alkenyl, such as 2-propenyl, 2-butenyl, 3-butenyl, 1-methyl-2-propenyl, 2-methyl-2-propenyl, 2-pentenyl, 3-pentenyl, 4-pentenyl, 3-methyl-2-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl; alkynyl, such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl; in particular 2-propenyl or 2-propynyl, or phenyl and naphthyl, where these groups may carry from one to three of the radicals stated in general and in particular for R;

a 5-membered or 6-membered heterocyclic structure containing one or two heteroatoms selected from the group consisting of nitrogen, oxygen and sulfur, such as 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 4-pyrrolyl, 3-pyrazolyl, 4-pyrazolyl, 5-pyrazolyl, 2-pyridyl, 3-pyridyl, 4-pyridyl and 2-(4,6-dimethylprimidinyl), where this ring may carry one or two of the following radicals: halogen, alkyl, haloalkyl, alkoxy, haloalkoxy and/or alkylthio as stated in general and in particular for $R^1$;

one of the groups stated in general or in particular for $R^1$, or $R^1$ and $R^2$ together form a 4-membered to 7-membered chain which, in addition to methylene groups, may contain one of the following groups as ring member: oxygen, sulfur, $N(CH_3)$— or —CO—, such as —$(CH_2)_3$—, —$(CH_2)_4$—, —$(CH_2)_5$—, $(CH_2)_6$—, —$CH_2$—O—$CH_2$—, —$CH_2$—CH$_2$—O—$CH_2$—$CH_2$—, —$CH_2$—S—$CH_2$—, —$CH_2$—$CH_2$—S—$CH_2$—$CH_2$—, —$CH_2$—$CH_2$—$N(CH_3)$—$CH_2$—$CH_2$ and —$(CH_2)_3$—CO—, in particular —$(CH_2)_5$— and —$CH_2$—$CH_2$—O—$CH_2$—$CH_2$;

$R^3$ and $R^4$ are each nitro; cyano;

halogen, in particular fluorine, chlorine or bromine;

amino which may carry one or two $C_1$-$C_4$-alkyl groups as stated for $R^1$, in particular methyl or ethyl, and/or an alkylcarbonyl group, such as methylcarbonyl, ethylcarbonyl, propylcarbonyl, 1-methylethylcarbonyl, butylcarbonyl, 1-methylpropylcarbonyl, 2-methylpropylcarbonyl or 1,1-dimethylethylcarbonyl, in particular methylcarbonyl or ethylcarbonyl;

alkoxy or alkylthio, in particular methoxy, methylthio or ethylthio, where these groups may carry from one to nine halogen atoms, in particular fluorine or chlorine;

a 5-membered or 6-membered heterocyclic structure containing one or two heteroatoms selected from the group consisting of oxygen, sulfur or nitrogen, as stated for $R^2$, where this ring may carry one or two of the following radicals: halogen, in particular fluorine or chlorine, alkyl, in particular methyl, haloalkyl, in particular trifluoromethyl or chlorodifluoromethyl, alkoxy, in particular methoxy or ethoxy, haloalkoxy, in particular trifluoromethoxy, trichloromethoxy or pentafluoroethoxy, and/or alkylthio, in particular methylthio;

alkenyl, such as ethenyl, 1-propenyl, 1-methylethenyl, 1-butenyl, 1-methyl-1-propenyl, 2-methyl-1-propenyl, 1-pentenyl, 1-methyl-1-butenyl, 2-methyl-1-butenyl, 1,1-dimethyl-1-propenyl, 1-ethyl-1-propenyl, 1-hexenyl, 1-methyl-1-pentenyl, 2-methyl-1-pentenyl, 3-methyl-1-pentenyl, 4-methyl-1-pentenyl, 1,2-dimethyl-1-butenyl, 1,3-dimethyl-1-butenyl, 2,3-dimethyl-1-butenyl, 3,3-dimethyl-1-butenyl, 1-ethyl-1-butenyl, 2-ethyl-1-butenyl or 1-ethyl-2-methyl-1-propenyl, in particular 2-propenyl;

alkynyl, such as ethynyl, 1-propynyl, 1-butynyl, 1-pentynyl, 1-methyl-3-butynyl, 1-hexynyl, 3-methyl-1-pentynyl, 4-methyl-1-pentynyl or 3,3-dimethyl-1-butynyl, in particular 2-propynyl, or phenyl, where these groups may carry from one to three of the radicals stated in general and in particular for R, or one of the groups stated in general and in particular for $R^1$;

$R^5$ is formyl, 4,5-dihydrooxazol-2-yl or $COYR^6$;

Y is oxygen or sulfur;

$R^6$ is hydrogen;

cycloalkyl as stated for $R^1$, in particular cyclopentyl or cyclohexyl;

alkyl as stated for $R^1$, in particular methyl, ethyl, propyl, 1-methylethyl or hexyl, which may carry from one to five halogen atoms, in particular fluorine or chlorine, or hydroxyl groups and/or one of the following radicals: cyano, aminocarbonyl, carboxyl, trimethylsilyl, alkoxy, in particular methoxy or ethoxy, alkoxyalkoxy, in particular methoxyethoxy, ethoxyethoxy or propoxyethoxy, in particular methoxyethoxy, alkylthio, in particular methylthio or ethylthio; alkylamino, in particular methylamino or ethylamino, dialkylamino, in particular dimethylamino or methylethylamino, alkylsulfynyl, such as methylsulfynyl, ethylsulfynyl, propylsulfynyl or isopropylsulfynyl, in particular methylsulfynyl or ethylsulfynyl, alkylsulfonyl, such as methylsulfonyl, ethylsulfonyl, propylsulfonyl or isopropylsulfonyl, in particular methylsulfonyl or ethylsulfonyl, alkoxycarbonyl, in particular methoxycarbonyl, alkoxycarbonylalkoxy, such as methoxycarbonylmethoxy, methoxycarbonylethoxy or ethoxycarbonylethoxy, alkoxycarbonylalkoxycarbonyl, such as methoxycarbonylmethoxycarbonyl, methoxycarbonylethoxycarbonyl or ethoxycarbonylethoxycarbonyl, alkylaminocarbonyl, such as methylaminocarbonyl, ethylaminocarbonyl, propylaminocarbonyl or isopropylaminocarbonyl, in particular methylaminocarbonyl or ethylaminocarbonyl, dialkylaminocarbonyl, such as dimethylaminocarbonyl, diethylaminocarbonyl, dipropylaminocarbonyl, diisopropylaminocarbonyl, dicyclopropylaminocarbonyl, or methylethylaminocarbonyl, in particular dimethylaminocarbonyl or diethylaminocarbonyl, dialkoxyphosphonyl, such as dimethoxyphosphonyl, diethoxyphosphonyl, dipropoxyphosphonyl or diisopropoxyphosphonyl, in particular dimethoxyphosphonyl or diethoxyphosphonyl, alkaneiminoxy, in particular 2-propaneiminoxy, phenyl, thienyl, benzyloxy, benzylthio, furyl, tetrahydrofuryl, phthalimido and/or benzoyl, where the cyclic radicals in turn may carry from one to three of the radicals stated in general and in particular for R;

alkenyl, in particular 2-propenyl or 2-butenyl, alkynyl, in particular 2-propynyl, or cycloalkenyl, in particular 2-cyclopentenyl or 2-cyclohexenyl, where these groups may carry one of the following radicals: hydroxyl, halogen, in particular fluorine or chlorine, alkoxy, in particular methoxy or ethoxy, or phenyl, where the phenyl radical in turn may carry from one to three of the radicals stated in general and in particular for R;

a 5-membered or 6-membered heterocyclic structure containing one or two heteroatoms selected from the group consisting of nitrogen, oxygen and sulfur, as stated for $R^2$, in particular tetrahydrofuranyl or tetrahydropyranyl;

phthalimido; tetrahydrophthalimido; succinimido; maleimido; benzotriazolyl;

phenyl which may carry from one to three of the radicals stated in general and in particular for R;

$N=CR^7R^8$, where $R^7$ is hydrogen or alkyl as stated for $R^1$, in particular methyl, ethyl or 1-methylethyl, and $R^8$ is cycloalkyl, in particular cyclopropyl, phenyl, furyl or one of the groups stated for $R^7$, or $R^7$ and $R^8$ together form an alkylene chain, such as butylene, pentylene, hexylene or heptylene, in particular butylene or pentylene.

TABLE

Ia/IA, Ib/IB, Ic/IC (structures)

| $R^3$ | $R^4$ | $R^1$ | $R^2$ | Y | $R^6$ |
|---|---|---|---|---|---|
| H | F | H | methyl | O | H |
| H | F | H | ethyl | O | H |
| H | F | H | n-propyl | O | H |
| H | F | H | iso-propyl | O | H |

TABLE-continued

Ia/IA, Ib/IB, Ic/IC structures

| R³ | R⁴ | R¹ | R² | Y | R⁶ |
|---|---|---|---|---|---|
| H | F | H | cyclopropyl | O | H |
| H | F | H | n-butyl | O | H |
| H | F | H | iso-butyl | O | H |
| H | F | H | sec.-butyl | O | H |
| H | F | H | tert.-butyl | O | H |
| H | F | H | n-pentyl | O | H |
| H | F | H | 2-pentyl | O | H |
| H | F | H | 3-pentyl | O | H |
| H | F | H | n-hexyl | O | H |
| H | F | H | 2-hexyl | O | H |
| H | F | H | 3-hexyl | O | H |
| H | F | H | 2-methyl-2-pentyl | O | H |
| H | F | H | cyclo-propylmethyl | O | H |
| H | F | H | cyclo-butyl | O | H |
| H | F | H | cyclo-pentyl | O | H |
| H | F | H | cyclo-hexyl | O | H |
| H | F | H | 1-methylcyclohexyl | O | H |
| H | F | H | 3-trifluoromethylcyclohexyl | O | H |
| H | F | H | allyl | O | H |
| H | F | H | 1-buten-3-yl | O | H |
| H | F | H | crotyl | O | H |
| H | F | H | propargyl | O | H |
| H | F | H | 1-butyn-3-yl | O | H |
| H | F | H | 3-methyl-1-butyn-3-yl | O | H |
| H | F | H | 2-pentyn-4-yl | O | H |
| H | F | H | benzyl | O | H |
| H | F | H | 2-phenylethyl | O | H |
| H | F | H | 2-methylthioethyl | O | H |
| H | F | H | 2-chloroethyl | O | H |
| H | F | H | 2-methoxyethyl | O | H |
| H | F | H | 2-(N,N-dimethylamino)ethyl | O | H |
| H | F | H | phenyl | O | H |
| H | F | H | 2-$CH_3$-phenyl | O | H |
| H | F | H | 3-$CH_3$-phenyl | O | H |
| H | F | H | 4-$CH_3$-phenyl | O | H |
| H | F | H | 2,4-($CH_3$,$CH_3$)-phenyl | O | H |
| H | F | H | 2,3,5-($CH_3$,$CH_3$,$CH_3$)-phenyl | O | H |
| H | F | H | 3-$CF_3$-phenyl | O | H |
| H | F | H | 3-F-phenyl | O | H |
| H | F | H | 2-Cl-phenyl | O | H |
| H | F | H | 4-Cl-phenyl | O | H |
| H | F | H | 2,4-(F,F)-phenyl | O | H |
| H | F | H | 2,3,5-(Cl,Cl,Cl)-phenyl | O | H |
| H | F | H | 2-CN-phenyl | O | H |
| H | F | H | 2-$OCH_3$-phenyl | O | H |
| H | F | H | 2,3-($OCH_3$,$OCH_3$)-phenyl | O | H |
| H | F | H | 3,4,5-($OCH_3$,$OCH_3$,$OCH_3$)-phenyl | O | H |
| H | F | H | 3-$OCF_3$-phenyl | O | H |
| H | F | H | 3-$OCF_2OHF_2$-phenyl | O | H |
| H | F | H | 4-$OCF_2CHF_2$-phenyl | O | H |
| H | F | H | 2-$SCH_3$-phenyl | O | H |
| H | F | H | 2,4-($SCH_3$,$SCH_3$)-phenyl | O | H |
| H | F | H | 2-$SCF_3$-phenyl | O | H |
| H | F | H | 4-$NO_2$-phenyl | O | H |
| H | F | H | 2,4-($NO_2$,$NO_2$)-phenyl | O | H |
| H | F | H | 3-$COCH_3$-phenyl | O | H |
| H | F | H | 3-$COCF_3$-phenyl | O | H |
| H | F | H | 1-naphthyl | O | H |
| H | F | H | 2-naphthyl | O | H |
| H | F | H | piperidino | O | H |
| H | F | H | 3-tetrahydrofuranyl | O | H |
| H | F | H | 4-tetrahydropyranyl | O | H |
| H | F | H | 2-thiazolyl | O | H |
| H | F | H | 5-$CH_3$-2-thiazolyl | O | H |
| H | F | H | 4-$CH_3$-5-COOH-2-thiazolyl | O | H |
| H | Cl | H | methyl | O | H |
| H | Cl | H | ethyl | O | H |
| H | Cl | H | n-propyl | O | H |
| H | Cl | H | iso-propyl | O | H |
| H | Cl | H | cyclopropyl | O | H |
| H | Cl | H | n-butyl | O | H |

TABLE-continued

| | | | | | |
|---|---|---|---|---|---|
| | | Ia/IA | Ib/IB | Ic/IC | |

| R³ | R⁴ | R¹ | R² | Y | R⁶ |
|---|---|---|---|---|---|
| H | Cl | H | iso-butyl | O | H |
| H | Cl | H | sec.-butyl | O | H |
| H | Cl | H | tert.-butyl | O | H |
| H | Cl | H | n-pentyl | O | H |
| H | Cl | H | 2-pentyl | O | H |
| H | Cl | H | 3-pentyl | O | H |
| H | Cl | H | n-hexyl | O | H |
| H | Cl | H | 2-hexyl | O | H |
| H | Cl | H | 3-hexyl | O | H |
| H | Cl | H | 2-methyl-2-pentyl | O | H |
| H | Cl | H | cyclo-propylmethyl | O | H |
| H | Cl | H | cyclo-butyl | O | H |
| H | Cl | H | cyclo-pentyl | O | H |
| H | Cl | H | cyclo-hexyl | O | H |
| H | Cl | H | 1-methylcyclohexyl | O | H |
| H | Cl | H | 3-trifluoromethylcyclohexyl | O | H |
| H | Cl | H | allyl | O | H |
| H | Cl | H | 1-buten-3-yl | O | H |
| H | Cl | H | crotyl | O | H |
| H | Cl | H | propargyl | O | H |
| H | Cl | H | 1-butyn-3-yl | O | H |
| H | Cl | H | 3-methyl-1-butyn-3-yl | O | H |
| H | Cl | H | 2-pentyn-4-yl | O | H |
| H | Cl | H | benzyl | O | H |
| H | Cl | H | 2-phenylethyl | O | H |
| H | Cl | H | 2-methylthioethyl | O | H |
| H | Cl | H | 2-chloroethyl | O | H |
| H | Cl | H | 2-methoxyethyl | O | H |
| H | Cl | H | 2-(N,N-dimethylamino)ethyl | O | H |
| H | Cl | H | phenyl | O | H |
| H | Cl | H | 2-$CH_3$-phenyl | O | H |
| H | Cl | H | 3-$CH_3$-phenyl | O | H |
| H | Cl | H | 4-$CH_3$-phenyl | O | H |
| H | Cl | H | 2,4-($CH_3$,$CH_3$)-phenyl | O | H |
| H | Cl | H | 2,3,5-($CH_3$,$CH_3$,$CH_3$)-phenyl | O | H |
| H | Cl | H | 3-$CF_3$-phenyl | O | H |
| H | Cl | H | 3-F-phenyl | O | H |
| H | Cl | H | 2-Cl-phenyl | O | H |
| H | Cl | H | 4-Cl-phenyl | O | H |
| H | Cl | H | 2,4-(F,F)-phenyl | O | H |
| H | Cl | H | 2,3,5-(Cl,Cl,Cl)-phenyl | O | H |
| H | Cl | H | 2-CN-phenyl | O | H |
| H | Cl | H | 2-$OCH_3$-phenyl | O | H |
| H | Cl | H | 2,3-($OCH_3$,$OCH_3$)-phenyl | O | H |
| H | Cl | H | 3,4,5-($OCH_3$,$OCH_3$,$OCH_3$)-phenyl | O | H |
| H | Cl | H | 3-$OCF_3$-phenyl | O | H |
| H | Cl | H | 3-$OCF_2OHF_2$-phenyl | O | H |
| H | Cl | H | 4-$OCF_2CHF_2$-phenyl | O | H |
| H | Cl | H | 2-$SCH_3$-phenyl | O | H |
| H | Cl | H | 2,4-($SCH_3$,$SCH_3$)-phenyl | O | H |
| H | Cl | H | 2-$SCF_3$-phenyl | O | H |
| H | Cl | H | 4-$NO_2$-phenyl | O | H |
| H | Cl | H | 2,4-($NO_2$,$NO_2$)-phenyl | O | H |
| H | Cl | H | 3-$COCH_3$-phenyl | O | H |
| H | Cl | H | 3-$COCF_3$-phenyl | O | H |
| H | Cl | H | 1-naphthyl | O | H |
| H | Cl | H | 2-naphthyl | O | H |
| H | Cl | H | piperidino | O | H |
| H | Cl | H | 3-tetrahydrofuranyl | O | H |
| H | Cl | H | 4-tetrahydropyranyl | O | H |
| H | Cl | H | 2-thiazolyl | O | H |
| H | Cl | H | 5-$CH_3$-2-thiazolyl | O | H |
| H | Cl | H | 4-$CH_3$-5-COOH-2-thiazolyl | O | H |
| H | Br | H | methyl | O | H |
| H | Br | H | ethyl | O | H |
| H | Br | H | n-propyl | O | H |
| H | Br | H | iso-propyl | O | H |
| H | Br | H | cyclopropyl | O | H |
| H | Br | H | n-butyl | O | H |
| H | Br | H | iso-butyl | O | H |
| H | Br | H | sec.-butyl | O | H |

TABLE-continued

Ia/IA: R⁶Y-C(=O)-C=C(-R⁴)(-X-)(-R³)-C(=O)-NR¹R²

Ib/IB: R³ structure with NR¹R² and YR⁶

Ic/IC: R³ structure with YR⁶ and NR¹R²

| R³ | R⁴ | R¹ | R² | Y | R⁶ |
|---|---|---|---|---|---|
| H | Br | H | tert.-butyl | O | H |
| H | Br | H | n-pentyl | O | H |
| H | Br | H | 2-pentyl | O | H |
| H | Br | H | 3-pentyl | O | H |
| H | Br | H | n-hexyl | O | H |
| H | Br | H | 2-hexyl | O | H |
| H | Br | H | 3-hexyl | O | H |
| H | Br | H | 2-methyl-2-pentyl | O | H |
| H | Br | H | cyclo-propylmethyl | O | H |
| H | Br | H | cyclo-butyl | O | H |
| H | Br | H | cyclo-pentyl | O | H |
| H | Br | H | cyclo-hexyl | O | H |
| H | Br | H | 1-methylcyclohexyl | O | H |
| H | Br | H | 3-trifluoromethylcyclohexyl | O | H |
| H | Br | H | allyl | O | H |
| H | Br | H | 1-buten-3-yl | O | H |
| H | Br | H | crotyl | O | H |
| H | Br | H | propargyl | O | H |
| H | Br | H | 1-butyn-3-yl | O | H |
| H | Br | H | 3-methyl-1-butyn-3-yl | O | H |
| H | Br | H | 2-pentyn-4-yl | O | H |
| H | Br | H | benzyl | O | H |
| H | Br | H | 2-phenylethyl | O | H |
| H | Br | H | 2-methylthioethyl | O | H |
| H | Br | H | 2-chloroethyl | O | H |
| H | Br | H | 2-methoxyethyl | O | H |
| H | Br | H | 2-(N,N-dimethylamino)ethyl | O | H |
| H | Br | H | phenyl | O | H |
| H | Br | H | 2-CH₃-phenyl | O | H |
| H | Br | H | 3-CH₃-phenyl | O | H |
| H | Br | H | 4-CH₃-phenyl | O | H |
| H | Br | H | 2,4-(CH₃,CH₃)-phenyl | O | H |
| H | Br | H | 2,3,5-(CH₃,CH₃,CH₃)-phenyl | O | H |
| H | Br | H | 3-CF₃-phenyl | O | H |
| H | Br | H | 3-F-phenyl | O | H |
| H | Br | H | 2-Cl-phenyl | O | H |
| H | Br | H | 4-Cl-phenyl | O | H |
| H | Br | H | 2,4-(F,F)-phenyl | O | H |
| H | Br | H | 2,3,5-(Cl,Cl,Cl)-phenyl | O | H |
| H | Br | H | 2-CN-phenyl | O | H |
| H | Br | H | 2-OCH₃-phenyl | O | H |
| H | Br | H | 2,3-(OCH₃,OCH₃)-phenyl | O | H |
| H | Br | H | 3,4,5-(OCH₃,OCH₃,OCH₃)-phenyl | O | H |
| H | Br | H | 3-OCF₃-phenyl | O | H |
| H | Br | H | 3-OCF₂OHF₂-phenyl | O | H |
| H | Br | H | 4-OCF₂CHF₂-phenyl | O | H |
| H | Br | H | 2-SCH₃-phenyl | O | H |
| H | Br | H | 2,4-(SCH₃,SCH₃)-phenyl | O | H |
| H | Br | H | 2-SCF₃-phenyl | O | H |
| H | Br | H | 4-NO₂-phenyl | O | H |
| H | Br | H | 2,4-(NO₂,NO₂)-phenyl | O | H |
| H | Br | H | 3-COCH₃-phenyl | O | H |
| H | Br | H | 3-COCF₃-phenyl | O | H |
| H | Br | H | 1-naphthyl | O | H |
| H | Br | H | 2-naphthyl | O | H |
| H | Br | H | piperidino | O | H |
| H | Br | H | 3-tetrahydrofuranyl | O | H |
| H | Br | H | 4-tetrahydropyranyl | O | H |
| H | Br | H | 2-thiazolyl | O | H |
| H | Br | H | 5-CH₃-2-thiazolyl | O | H |
| H | Br | H | 4-CH₃-5-COOH-2-thiazolyl | O | H |
| H | I | H | methyl | O | H |
| H | I | H | ethyl | O | H |
| H | I | H | n-propyl | O | H |
| H | I | H | iso-propyl | O | H |
| H | I | H | cyclopropyl | O | H |
| H | I | H | n-butyl | O | H |
| H | I | H | iso-butyl | O | H |
| H | I | H | sec.-butyl | O | H |
| H | I | H | tert.-butyl | O | H |
| H | I | H | n-pentyl | O | H |

TABLE-continued

|   | Ia/IA | | Ib/IB | | Ic/IC |
|---|---|---|---|---|---|

| $R^3$ | $R^4$ | $R^1$ | $R^2$ | Y | $R^6$ |
|---|---|---|---|---|---|
| H | I | H | 2-pentyl | O | H |
| H | I | H | 3-pentyl | O | H |
| H | I | H | n-hexyl | O | H |
| H | I | H | 2-hexyl | O | H |
| H | I | H | 3-hexyl | O | H |
| H | I | H | 2-methyl-2-pentyl | O | H |
| H | I | H | cyclo-propylmethyl | O | H |
| H | I | H | cyclo-butyl | O | H |
| H | I | H | cyclo-pentyl | O | H |
| H | I | H | cyclo-hexyl | O | H |
| H | I | H | 1-methylcyclohexyl | O | H |
| H | I | H | 3-trifluoromethylcyclohexyl | O | H |
| H | I | H | allyl | O | H |
| H | I | H | 1-buten-3-yl | O | H |
| H | I | H | crotyl | O | H |
| H | I | H | propargyl | O | H |
| H | I | H | 1-butyn-3-yl | O | H |
| H | I | H | 3-methyl-1-butyn-3-yl | O | H |
| H | I | H | 2-pentyn-4-yl | O | H |
| H | I | H | benzyl | O | H |
| H | I | H | 2-phenylethyl | O | H |
| H | I | H | 2-methylthioethyl | O | H |
| H | I | H | 2-chloroethyl | O | H |
| H | I | H | 2-methoxyethyl | O | H |
| H | I | H | 2-(N,N-dimethylamino)ethyl | O | H |
| H | I | H | phenyl | O | H |
| H | I | H | 2-$CH_3$-phenyl | O | H |
| H | I | H | 3-$CH_3$-phenyl | O | H |
| H | I | H | 4-$CH_3$-phenyl | O | H |
| H | I | H | 2,4-($CH_3$,$CH_3$)-phenyl | O | H |
| H | I | H | 2,3,5-($CH_3$,$CH_3$,$CH_3$)-phenyl | O | H |
| H | I | H | 3-$CF_3$-phenyl | O | H |
| H | I | H | 3-F-phenyl | O | H |
| H | I | H | 2-Cl-phenyl | O | H |
| H | I | H | 4-Cl-phenyl | O | H |
| H | I | H | 2,4-(F,F)-phenyl | O | H |
| H | I | H | 2,3,5-(Cl,Cl,Cl)-phenyl | O | H |
| H | I | H | 2-CN-phenyl | O | H |
| H | I | H | 2-$OCH_3$-phenyl | O | H |
| H | I | H | 2,3-($OCH_3$,$OCH_3$)-phenyl | O | H |
| H | I | H | 3,4,5-($OCH_3$,$OCH_3$,$OCH_3$)-phenyl | O | H |
| H | I | H | 3-$OCF_3$-phenyl | O | H |
| H | I | H | 3-$OCF_2OHF_2$-phenyl | O | H |
| H | I | H | 4-$OCF_2CHF_2$-phenyl | O | H |
| H | I | H | 2-$SCH_3$-phenyl | O | H |
| H | I | H | 2,4-($SCH_3$,$SCH_3$)-phenyl | O | H |
| H | I | H | 2-$SCF_3$-phenyl | O | H |
| H | I | H | 4-$NO_2$-phenyl | O | H |
| H | I | H | 2,4-($NO_2$,$NO_2$)-phenyl | O | H |
| H | I | H | 3-$COCH_3$-phenyl | O | H |
| H | I | H | 3-$COCF_3$-phenyl | O | H |
| H | I | H | 1-naphthyl | O | H |
| H | I | H | 2-naphthyl | O | H |
| H | I | H | piperidino | O | H |
| H | I | H | 3-tetrahydrofuranyl | O | H |
| H | I | H | 4-tetrahydropyranyl | O | H |
| H | I | H | 2-thiazolyl | O | H |
| H | I | H | 5-$CH_3$-2-thiazolyl | O | H |
| H | I | H | 4-$CH_3$-5-COOH-2-thiazolyl | O | H |
| F | H | H | methyl | O | H |
| F | H | H | ethyl | O | H |
| F | H | H | n-propyl | O | H |
| F | H | H | iso-propyl | O | H |
| F | H | H | cyclopropyl | O | H |
| F | H | H | n-butyl | O | H |
| F | H | H | iso-butyl | O | H |
| F | H | H | sec.-butyl | O | H |
| F | H | H | tert.-butyl | O | H |
| F | H | H | n-pentyl | O | H |
| F | H | H | 2-pentyl | O | H |
| F | H | H | 3-pentyl | O | H |

TABLE-continued

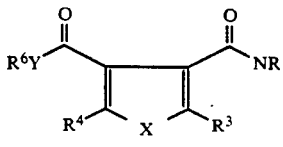

| R³ | R⁴ | R¹ | R² | Y | R⁶ |
|---|---|---|---|---|---|
| F | H | H | n-hexyl | O | H |
| F | H | H | 2-hexyl | O | H |
| F | H | H | 3-hexyl | O | H |
| F | H | H | 2-methyl-2-pentyl | O | H |
| F | H | H | cyclo-propylmethyl | O | H |
| F | H | H | cyclo-butyl | O | H |
| F | H | H | cyclo-pentyl | O | H |
| F | H | H | cyclo-hexyl | O | H |
| F | H | H | 1-methylcyclohexyl | O | H |
| F | H | H | 3-trifluoromethylcyclohexyl | O | H |
| F | H | H | allyl | O | H |
| F | H | H | 1-buten-3-yl | O | H |
| F | H | H | crotyl | O | H |
| F | H | H | propargyl | O | H |
| F | H | H | 1-butyn-3-yl | O | H |
| F | H | H | 3-methyl-1-butyn-3-yl | O | H |
| F | H | H | 2-pentyn-4-yl | O | H |
| F | H | H | benzyl | O | H |
| F | H | H | 2-phenylethyl | O | H |
| F | H | H | 2-methylthioethyl | O | H |
| F | H | H | 2-chloroethyl | O | H |
| F | H | H | 2-methoxyethyl | O | H |
| F | H | H | 2-(N,N-dimethylamino)ethyl | O | H |
| F | H | H | phenyl | O | H |
| F | H | H | 2-CH₃-phenyl | O | H |
| F | H | H | 3-CH₃-phenyl | O | H |
| F | H | H | 4-CH₃-phenyl | O | H |
| F | H | H | 2,4-(CH₃,CH₃)-phenyl | O | H |
| F | H | H | 2,3,5-(CH₃,CH₃,CH₃)-phenyl | O | H |
| F | H | H | 3-CF₃-phenyl | O | H |
| F | H | H | 3-F-phenyl | O | H |
| F | H | H | 2-Cl-phenyl | O | H |
| F | H | H | 4-Cl-phenyl | O | H |
| F | H | H | 2,4-(F,F)-phenyl | O | H |
| F | H | H | 2,3,5-(Cl,Cl,Cl)-phenyl | O | H |
| F | H | H | 2-CN-phenyl | O | H |
| F | H | H | 2-OCH₃-phenyl | O | H |
| F | H | H | 2,3-(OCH₃,OCH₃)-phenyl | O | H |
| F | H | H | 3,4,5-(OCH₃,OCH₃,OCH₃)-phenyl | O | H |
| F | H | H | 3-OCF₃-phenyl | O | H |
| F | H | H | 3-OCF₂OHF₂-phenyl | O | H |
| F | H | H | 4-OCF₂CHF₂-phenyl | O | H |
| F | H | H | 2-SCH₃-phenyl | O | H |
| F | H | H | 2,4-(SCH₃,SCH₃)-phenyl | O | H |
| F | H | H | 2-SCF₃-phenyl | O | H |
| F | H | H | 4-NO₂-phenyl | O | H |
| F | H | H | 2,4-(NO₂,NO₂)-phenyl | O | H |
| F | H | H | 3-COCH₃-phenyl | O | H |
| F | H | H | 3-COCF₃-phenyl | O | H |
| F | H | H | 1-naphthyl | O | H |
| F | H | H | 2-naphthyl | O | H |
| F | H | H | piperidino | O | H |
| F | H | H | 3-tetrahydrofuranyl | O | H |
| F | H | H | 4-tetrahydropyranyl | O | H |
| F | H | H | 2-thiazolyl | O | H |
| F | H | H | 5-CH₃-2-thiazolyl | O | H |
| F | H | H | 4-CH₃-5-COOH-2-thiazolyl | O | H |
| Cl | H | H | methyl | O | H |
| Cl | H | H | ethyl | O | H |
| Cl | H | H | n-propyl | O | H |
| Cl | H | H | iso-propyl | O | H |
| Cl | H | H | cyclopropyl | O | H |
| Cl | H | H | n-butyl | O | H |
| Cl | H | H | iso-butyl | O | H |
| Cl | H | H | sec.-butyl | O | H |
| Cl | H | H | tert.-butyl | O | H |
| Cl | H | H | n-pentyl | O | H |
| Cl | H | H | 2-pentyl | O | H |
| Cl | H | H | 3-pentyl | O | H |
| Cl | H | H | n-hexyl | O | H |
| Cl | H | H | 2-hexyl | O | H |

TABLE-continued

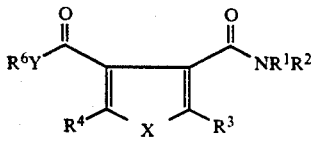

| | | | Ia/IA | | Ib/IB | | Ic/IC | |
|---|---|---|---|---|---|---|---|---|

| $R^3$ | $R^4$ | $R^1$ | $R^2$ | Y | $R^6$ |
|---|---|---|---|---|---|
| Cl | H | H | 3-hexyl | O | H |
| Cl | H | H | 2-methyl-2-pentyl | O | H |
| Cl | H | H | cyclo-propylmethyl | O | H |
| Cl | H | H | cyclo-butyl | O | H |
| Cl | H | H | cyclo-pentyl | O | H |
| Cl | H | H | cyclo-hexyl | O | H |
| Cl | H | H | 1-methylcyclohexyl | O | H |
| Cl | H | H | 3-trifluoromethylcyclohexyl | O | H |
| Cl | H | H | allyl | O | H |
| Cl | H | H | 1-buten-3-yl | O | H |
| Cl | H | H | crotyl | O | H |
| Cl | H | H | propargyl | O | H |
| Cl | H | H | 1-butyn-3-yl | O | H |
| Cl | H | H | 3-methyl-1-butyn-3-yl | O | H |
| Cl | H | H | 2-pentyn-4-yl | O | H |
| Cl | H | H | benzyl | O | H |
| Cl | H | H | 2-phenylethyl | O | H |
| Cl | H | H | 2-methylthioethyl | O | H |
| Cl | H | H | 2-chloroethyl | O | H |
| Cl | H | H | 2-methoxyethyl | O | H |
| Cl | H | H | 2-(N,N-dimethylamino)ethyl | O | H |
| Cl | H | H | phenyl | O | H |
| Cl | H | H | 2-$CH_3$-phenyl | O | H |
| Cl | H | H | 3-$CH_3$-phenyl | O | H |
| Cl | H | H | 4-$CH_3$-phenyl | O | H |
| Cl | H | H | 2,4-($CH_3$,$CH_3$)-phenyl | O | H |
| Cl | H | H | 2,3,5-($CH_3$,$CH_3$,$CH_3$)-phenyl | O | H |
| Cl | H | H | 3-$CF_3$-phenyl | O | H |
| Cl | H | H | 3-F-phenyl | O | H |
| Cl | H | H | 2-Cl-phenyl | O | H |
| Cl | H | H | 4-Cl-phenyl | O | H |
| Cl | H | H | 2,4-(F,F)-phenyl | O | H |
| Cl | H | H | 2,3,5-(Cl,Cl,Cl)-phenyl | O | H |
| Cl | H | H | 2-CN-phenyl | O | H |
| Cl | H | H | 2-$OCH_3$-phenyl | O | H |
| Cl | H | H | 2,3-($OCH_3$,$OCH_3$)-phenyl | O | H |
| Cl | H | H | 3,4,5-($OCH_3$,$OCH_3$,$OCH_3$)-phenyl | O | H |
| Cl | H | H | 3-$OCF_3$-phenyl | O | H |
| Cl | H | H | 3-$OCF_2OHF_2$-phenyl | O | H |
| Cl | H | H | 4-$OCF_2CHF_2$-phenyl | O | H |
| Cl | H | H | 2-$SCH_3$-phenyl | O | H |
| Cl | H | H | 2,4-($SCH_3$,$SCH_3$)-phenyl | O | H |
| Cl | H | H | 2-$SCF_3$-phenyl | O | H |
| Cl | H | H | 4-$NO_2$-phenyl | O | H |
| Cl | H | H | 2,4-($NO_2$,$NO_2$)-phenyl | O | H |
| Cl | H | H | 3-$COCH_3$-phenyl | O | H |
| Cl | H | H | 3-$COCF_3$-phenyl | O | H |
| Cl | H | H | 1-naphthyl | O | H |
| Cl | H | H | 2-naphthyl | O | H |
| Cl | H | H | piperidino | O | H |
| Cl | H | H | 3-tetrahydrofuranyl | O | H |
| Cl | H | H | 4-tetrahydropyranyl | O | H |
| Cl | H | H | 2-thiazolyl | O | H |
| Cl | H | H | 5-$CH_3$-2-thiazolyl | O | H |
| Cl | H | H | 4-$CH_3$-5-COOH-2-thiazolyl | O | H |
| Br | H | H | methyl | O | H |
| Br | H | H | ethyl | O | H |
| Br | H | H | n-propyl | O | H |
| Br | H | H | iso-propyl | O | H |
| Br | H | H | cyclopropyl | O | H |
| Br | H | H | n-butyl | O | H |
| Br | H | H | iso-butyl | O | H |
| Br | H | H | sec.-butyl | O | H |
| Br | H | H | tert.-butyl | O | H |
| Br | H | H | n-pentyl | O | H |
| Br | H | H | 2-pentyl | O | H |
| Br | H | H | 3-pentyl | O | H |
| Br | H | H | n-hexyl | O | H |
| Br | H | H | 2-hexyl | O | H |
| Br | H | H | 3-hexyl | O | H |
| Br | H | H | 2-methyl-2-pentyl | O | H |

TABLE-continued

| | Ia/IA | | Ib/IB | | Ic/IC |
|---|---|---|---|---|---|

| $R^3$ | $R^4$ | $R^1$ | $R^2$ | Y | $R^6$ |
|---|---|---|---|---|---|
| Br | H | H | cyclo-propylmethyl | O | H |
| Br | H | H | cyclo-butyl | O | H |
| Br | H | H | cyclo-pentyl | O | H |
| Br | H | H | cyclo-hexyl | O | H |
| Br | H | H | 1-methylcyclohexyl | O | H |
| Br | H | H | 3-trifluoromethylcyclohexyl | O | H |
| Br | H | H | allyl | O | H |
| Br | H | H | 1-buten-3-yl | O | H |
| Br | H | H | crotyl | O | H |
| Br | H | H | propargyl | O | H |
| Br | H | H | 1-butyn-3-yl | O | H |
| Br | H | H | 3-methyl-1-butyn-3-yl | O | H |
| Br | H | H | 2-pentyn-4-yl | O | H |
| Br | H | H | benzyl | O | H |
| Br | H | H | 2-phenylethyl | O | H |
| Br | H | H | 2-methylthioethyl | O | H |
| Br | H | H | 2-chloroethyl | O | H |
| Br | H | H | 2-methoxyethyl | O | H |
| Br | H | H | 2-(N,N-dimethylamino)ethyl | O | H |
| Br | H | H | phenyl | O | H |
| Br | H | H | 2-$CH_3$-phenyl | O | H |
| Br | H | H | 3-$CH_3$-phenyl | O | H |
| Br | H | H | 4-$CH_3$-phenyl | O | H |
| Br | H | H | 2,4-($CH_3$,$CH_3$)-phenyl | O | H |
| Br | H | H | 2,3,5-($CH_3$,$CH_3$,$CH_3$)-phenyl | O | H |
| Br | H | H | 3-$CF_3$-phenyl | O | H |
| Br | H | H | 3-F-phenyl | O | H |
| Br | H | H | 2-Cl-phenyl | O | H |
| Br | H | H | 4-Cl-phenyl | O | H |
| Br | H | H | 2,4-(F,F)-phenyl | O | H |
| Br | H | H | 2,3,5-(Cl,Cl,Cl)-phenyl | O | H |
| Br | H | H | 2-CN-phenyl | O | H |
| Br | H | H | 2-$OCH_3$-phenyl | O | H |
| Br | H | H | 2,3-($OCH_3$,$OCH_3$)-phenyl | O | H |
| Br | H | H | 3,4,5-($OCH_3$,$OCH_3$,$OCH_3$)-phenyl | O | H |
| Br | H | H | 3-$OCF_3$-phenyl | O | H |
| Br | H | H | 3-$OCF_2OHF_2$-phenyl | O | H |
| Br | H | H | 4-$OCF_2CHF_2$-phenyl | O | H |
| Br | H | H | 2-$SCH_3$-phenyl | O | H |
| Br | H | H | 2,4-($SCH_3$,$SCH_3$)-phenyl | O | H |
| Br | H | H | 2-$SCF_3$-phenyl | O | H |
| Br | H | H | 4-$NO_2$-phenyl | O | H |
| Br | H | H | 2,4-($NO_2$,$NO_2$)-phenyl | O | H |
| Br | H | H | 3-$COCH_3$-phenyl | O | H |
| Br | H | H | 3-$COCF_3$-phenyl | O | H |
| Br | H | H | 1-naphthyl | O | H |
| Br | H | H | 2-naphthyl | O | H |
| Br | H | H | piperidino | O | H |
| Br | H | H | 3-tetrahydrofuranyl | O | H |
| Br | H | H | 4-tetrahydropyranyl | O | H |
| Br | H | H | 2-thiazolyl | O | H |
| Br | H | H | 5-$CH_3$-2-thiazolyl | O | H |
| Br | H | H | 4-$CH_3$-5-COOH-2-thiazolyl | O | H |
| Cl | Cl | H | methyl | O | H |
| Cl | Cl | H | ethyl | O | H |
| Cl | Cl | H | n-propyl | O | H |
| Cl | Cl | H | iso-propyl | O | H |
| Cl | Cl | H | cyclopropyl | O | H |
| Cl | Cl | H | n-butyl | O | H |
| Cl | Cl | H | iso-butyl | O | H |
| Cl | Cl | H | sec.-butyl | O | H |
| Cl | Cl | H | tert.-butyl | O | H |
| Cl | Cl | H | n-pentyl | O | H |
| Cl | Cl | H | 2-pentyl | O | H |
| Cl | Cl | H | 3-pentyl | O | H |
| Cl | Cl | H | n-hexyl | O | H |
| Cl | Cl | H | 2-hexyl | O | H |
| Cl | Cl | H | 3-hexyl | O | H |
| Cl | Cl | H | 2-methyl-2-pentyl | O | H |
| Cl | Cl | H | cyclo-propylmethyl | O | H |
| Cl | Cl | H | cyclo-butyl | O | H |

TABLE-continued

| | Ia/IA | | Ib/IB | | Ic/IC | |
|---|---|---|---|---|---|---|

| $R^3$ | $R^4$ | $R^1$ | $R^2$ | Y | $R^6$ |
|---|---|---|---|---|---|
| Cl | Cl | H | cyclo-pentyl | O | H |
| Cl | Cl | H | cyclo-hexyl | O | H |
| Cl | Cl | H | 1-methylcyclohexyl | O | H |
| Cl | Cl | H | 3-trifluoromethylcyclohexyl | O | H |
| Cl | Cl | H | allyl | O | H |
| Cl | Cl | H | 1-buten-3-yl | O | H |
| Cl | Cl | H | crotyl | O | H |
| Cl | Cl | H | propargyl | O | H |
| Cl | Cl | H | 1-butyn-3-yl | O | H |
| Cl | Cl | H | 3-methyl-1-butyn-3-yl | O | H |
| Cl | Cl | H | 2-pentyn-4-yl | O | H |
| Cl | Cl | H | benzyl | O | H |
| Cl | Cl | H | 2-phenylethyl | O | H |
| Cl | Cl | H | 2-methylthioethyl | O | H |
| Cl | Cl | H | 2-chloroethyl | O | H |
| Cl | Cl | H | 2-methoxyethyl | O | H |
| Cl | Cl | H | 2-(N,N-dimethylamino)ethyl | O | H |
| Cl | Cl | H | phenyl | O | H |
| Cl | Cl | H | 2-$CH_3$-phenyl | O | H |
| Cl | Cl | H | 3-$CH_3$-phenyl | O | H |
| Cl | Cl | H | 4-$CH_3$-phenyl | O | H |
| Cl | Cl | H | 2,4-($CH_3$,$CH_3$)-phenyl | O | H |
| Cl | Cl | H | 2,3,5-($CH_3$,$CH_3$,$CH_3$)-phenyl | O | H |
| Cl | Cl | H | 3-$CF_3$-phenyl | O | H |
| Cl | Cl | H | 3-F-phenyl | O | H |
| Cl | Cl | H | 2-Cl-phenyl | O | H |
| Cl | Cl | H | 4-Cl-phenyl | O | H |
| Cl | Cl | H | 2,4-(F,F)-phenyl | O | H |
| Cl | Cl | H | 2,3,5-(Cl,Cl,Cl)-phenyl | O | H |
| Cl | Cl | H | 2-CN-phenyl | O | H |
| Cl | Cl | H | 2-$OCH_3$-phenyl | O | H |
| Cl | Cl | H | 2,3-($OCH_3$,$OCH_3$)-phenyl | O | H |
| Cl | Cl | H | 3,4,5-($OCH_3$,$OCH_3$,$OCH_3$)-phenyl | O | H |
| Cl | Cl | H | 3-$OCF_3$-phenyl | O | H |
| Cl | Cl | H | 3-$OCF_2OHF_2$-phenyl | O | H |
| Cl | Cl | H | 4-$OCF_2CHF_2$-phenyl | O | H |
| Cl | Cl | H | 2-$SCH_3$-phenyl | O | H |
| Cl | Cl | H | 2,4-($SCH_3$,$SCH_3$)-phenyl | O | H |
| Cl | Cl | H | 2-$SCF_3$-phenyl | O | H |
| Cl | Cl | H | 4-$NO_2$-phenyl | O | H |
| Cl | Cl | H | 2,4-($NO_2$,$NO_2$)-phenyl | O | H |
| Cl | Cl | H | 3-$COCH_3$-phenyl | O | H |
| Cl | Cl | H | 3-$COCF_3$-phenyl | O | H |
| Cl | Cl | H | 1-naphthyl | O | H |
| Cl | Cl | H | 2-naphthyl | O | H |
| Cl | Cl | H | piperidino | O | H |
| Cl | Cl | H | 3-tetrahydrofuranyl | O | H |
| Cl | Cl | H | 4-tetrahydropyranyl | O | H |
| Cl | Cl | H | 2-thiazolyl | O | H |
| Cl | Cl | H | 5-$CH_3$-2-thiazolyl | O | H |
| Cl | Cl | H | 4-$CH_3$-5-COOH-2-thiazolyl | O | H |
| Cl | Br | H | methyl | O | H |
| Cl | Br | H | ethyl | O | H |
| Cl | Br | H | n-propyl | O | H |
| Cl | Br | H | iso-propyl | O | H |
| Cl | Br | H | cyclopropyl | O | H |
| Cl | Br | H | n-butyl | O | H |
| Cl | Br | H | iso-butyl | O | H |
| Cl | Br | H | sec.-butyl | O | H |
| Cl | Br | H | tert.-butyl | O | H |
| Cl | Br | H | n-pentyl | O | H |
| Cl | Br | H | 2-pentyl | O | H |
| Cl | Br | H | 3-pentyl | O | H |
| Cl | Br | H | n-hexyl | O | H |
| Cl | Br | H | 2-hexyl | O | H |
| Cl | Br | H | 3-hexyl | O | H |
| Cl | Br | H | 2-methyl-2-pentyl | O | H |
| Cl | Br | H | cyclo-propylmethyl | O | H |
| Cl | Br | H | cyclo-butyl | O | H |
| Cl | Br | H | cyclo-pentyl | O | H |
| Cl | Br | H | cyclo-hexyl | O | H |

TABLE-continued

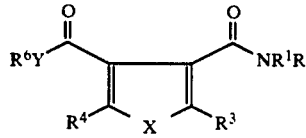

| | | | Ia/IA | Ib/IB | Ic/IC |

| $R^3$ | $R^4$ | $R^1$ | $R^2$ | Y | $R^6$ |
|---|---|---|---|---|---|
| Cl | Br | H | 1-methylcyclohexyl | O | H |
| Cl | Br | H | 3-trifluoromethylcyclohexyl | O | H |
| Cl | Br | H | allyl | O | H |
| Cl | Br | H | 1-buten-3-yl | O | H |
| Cl | Br | H | crotyl | O | H |
| Cl | Br | H | propargyl | O | H |
| Cl | Br | H | 1-butyn-3-yl | O | H |
| Cl | Br | H | 3-methyl-1-butyn-3-yl | O | H |
| Cl | Br | H | 2-pentyn-4-yl | O | H |
| Cl | Br | H | benzyl | O | H |
| Cl | Br | H | 2-phenylethyl | O | H |
| Cl | Br | H | 2-methylthioethyl | O | H |
| Cl | Br | H | 2-chloroethyl | O | H |
| Cl | Br | H | 2-methoxyethyl | O | H |
| Cl | Br | H | 2-(N,N-dimethylamino)ethyl | O | H |
| Cl | Br | H | phenyl | O | H |
| Cl | Br | H | 2-$CH_3$-phenyl | O | H |
| Cl | Br | H | 3-$CH_3$-phenyl | O | H |
| Cl | Br | H | 4-$CH_3$-phenyl | O | H |
| Cl | Br | H | 2,4-($CH_3$,$CH_3$)-phenyl | O | H |
| Cl | Br | H | 2,3,5-($CH_3$,$CH_3$,$CH_3$)-phenyl | O | H |
| Cl | Br | H | 3-$CF_3$-phenyl | O | H |
| Cl | Br | H | 3-F-phenyl | O | H |
| Cl | Br | H | 2-Cl-phenyl | O | H |
| Cl | Br | H | 4-Cl-phenyl | O | H |
| Cl | Br | H | 2,4-(F,F)-phenyl | O | H |
| Cl | Br | H | 2,3,5-(Cl,Cl,Cl)-phenyl | O | H |
| Cl | Br | H | 2-CN-phenyl | O | H |
| Cl | Br | H | 2-$OCH_3$-phenyl | O | H |
| Cl | Br | H | 2,3-($OCH_3$,$OCH_3$)-phenyl | O | H |
| Cl | Br | H | 3,4,5-($OCH_3$,$OCH_3$,$OCH_3$)-phenyl | O | H |
| Cl | Br | H | 3-$OCF_3$-phenyl | O | H |
| Cl | Br | H | 3-$OCF_2OHF_2$-phenyl | O | H |
| Cl | Br | H | 4-$OCF_2CHF_2$-phenyl | O | H |
| Cl | Br | H | 2-$SCH_3$-phenyl | O | H |
| Cl | Br | H | 2,4-($SCH_3$,$SCH_3$)-phenyl | O | H |
| Cl | Br | H | 2-$SCF_3$-phenyl | O | H |
| Cl | Br | H | 4-$NO_2$-phenyl | O | H |
| Cl | Br | H | 2,4-($NO_2$,$NO_2$)-phenyl | O | H |
| Cl | Br | H | 3-$COCH_3$-phenyl | O | H |
| Cl | Br | H | 3-$COCF_3$-phenyl | O | H |
| Cl | Br | H | 1-naphthyl | O | H |
| Cl | Br | H | 2-naphthyl | O | H |
| Cl | Br | H | piperidino | O | H |
| Cl | Br | H | 3-tetrahydrofuranyl | O | H |
| Cl | Br | H | 4-tetrahydropyranyl | O | H |
| Cl | Br | H | 2-thiazolyl | O | H |
| Cl | Br | H | 5-$CH_3$-2-thiazolyl | O | H |
| Cl | Br | H | 4-$CH_3$-5-COOH-2-thiazolyl | O | H |
| Br | Cl | H | methyl | O | H |
| Br | Cl | H | ethyl | O | H |
| Br | Cl | H | n-propyl | O | H |
| Br | Cl | H | iso-propyl | O | H |
| Br | Cl | H | cyclopropyl | O | H |
| Br | Cl | H | n-butyl | O | H |
| Br | Cl | H | iso-butyl | O | H |
| Br | Cl | H | sec.-butyl | O | H |
| Br | Cl | H | tert.-butyl | O | H |
| Br | Cl | H | n-pentyl | O | H |
| Br | Cl | H | 2-pentyl | O | H |
| Br | Cl | H | 3-pentyl | O | H |
| Br | Cl | H | n-hexyl | O | H |
| Br | Cl | H | 2-hexyl | O | H |
| Br | Cl | H | 3-hexyl | O | H |
| Br | Cl | H | 2-methyl-2-pentyl | O | H |
| Br | Cl | H | cyclo-propylmethyl | O | H |
| Br | Cl | H | cyclo-butyl | O | H |
| Br | Cl | H | cyclo-pentyl | O | H |
| Br | Cl | H | cyclo-hexyl | O | H |
| Br | Cl | H | 1-methylcyclohexyl | O | H |
| Br | Cl | H | 3-trifluoromethylcyclohexyl | O | H |

TABLE-continued

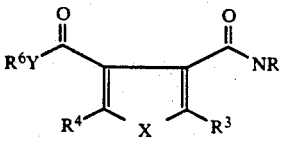

| R³ | R⁴ | R¹ | R² | Y | R⁶ |
|---|---|---|---|---|---|
| Br | Cl | H | allyl | O | H |
| Br | Cl | H | 1-buten-3-yl | O | H |
| Br | Cl | H | crotyl | O | H |
| Br | Cl | H | propargyl | O | H |
| Br | Cl | H | 1-butyn-3-yl | O | H |
| Br | Cl | H | 3-methyl-1-butyn-3-yl | O | H |
| Br | Cl | H | 2-pentyn-4-yl | O | H |
| Br | Cl | H | benzyl | O | H |
| Br | Cl | H | 2-phenylethyl | O | H |
| Br | Cl | H | 2-methylthioethyl | O | H |
| Br | Cl | H | 2-chloroethyl | O | H |
| Br | Cl | H | 2-methoxyethyl | O | H |
| Br | Cl | H | 2-(N,N-dimethylamino)ethyl | O | H |
| Br | Cl | H | phenyl | O | H |
| Br | Cl | H | 2-$CH_3$-phenyl | O | H |
| Br | Cl | H | 3-$CH_3$-phenyl | O | H |
| Br | Cl | H | 4-$CH_3$-phenyl | O | H |
| Br | Cl | H | 2,4-($CH_3$,$CH_3$)-phenyl | O | H |
| Br | Cl | H | 2,3,5-($CH_3$,$CH_3$,$CH_3$)-phenyl | O | H |
| Br | Cl | H | 3-$CF_3$-phenyl | O | H |
| Br | Cl | H | 3-F-phenyl | O | H |
| Br | Cl | H | 2-Cl-phenyl | O | H |
| Br | Cl | H | 4-Cl-phenyl | O | H |
| Br | Cl | H | 2,4-(F,F)-phenyl | O | H |
| Br | Cl | H | 2,3,5-(Cl,Cl,Cl)-phenyl | O | H |
| Br | Cl | H | 2-CN-phenyl | O | H |
| Br | Cl | H | 2-$OCH_3$-phenyl | O | H |
| Br | Cl | H | 2,3-($OCH_3$,$OCH_3$)-phenyl | O | H |
| Br | Cl | H | 3,4,5-($OCH_3$,$OCH_3$,$OCH_3$)-phenyl | O | H |
| Br | Cl | H | 3-$OCF_3$-phenyl | O | H |
| Br | Cl | H | 3-$OCF_2OHF_2$-phenyl | O | H |
| Br | Cl | H | 4-$OCF_2CHF_2$-phenyl | O | H |
| Br | Cl | H | 2-$SCH_3$-phenyl | O | H |
| Br | Cl | H | 2,4-($SCH_3$,$SCH_3$)-phenyl | O | H |
| Br | Cl | H | 2-$SCF_3$-phenyl | O | H |
| Br | Cl | H | 4-$NO_2$-phenyl | O | H |
| Br | Cl | H | 2,4-($NO_2$,$NO_2$)-phenyl | O | H |
| Br | Cl | H | 3-$COCH_3$-phenyl | O | H |
| Br | Cl | H | 3-$COCF_3$-phenyl | O | H |
| Br | Cl | H | 1-naphthyl | O | H |
| Br | Cl | H | 2-naphthyl | O | H |
| Br | Cl | H | piperidino | O | H |
| Br | Cl | H | 3-tetrahydrofuranyl | O | H |
| Br | Cl | H | 4-tetrahydropyranyl | O | H |
| Br | Cl | H | 2-thiazolyl | O | H |
| Br | Cl | H | 5-$CH_3$-2-thiazolyl | O | H |
| Br | Cl | H | 4-$CH_3$-5-COOH-2-thiazolyl | O | H |
| H | $OCH_3$ | H | methyl | O | H |
| H | $OCH_3$ | H | ethyl | O | H |
| H | $OCH_3$ | H | n-propyl | O | H |
| H | $OCH_3$ | H | iso-propyl | O | H |
| H | $OCH_3$ | H | cyclopropyl | O | H |
| H | $OCH_3$ | H | n-butyl | O | H |
| H | $OCH_3$ | H | iso-butyl | O | H |
| H | $OCH_3$ | H | sec.-butyl | O | H |
| H | $OCH_3$ | H | tert.-butyl | O | H |
| H | $OCH_3$ | H | n-pentyl | O | H |
| H | $OCH_3$ | H | 2-pentyl | O | H |
| H | $OCH_3$ | H | 3-pentyl | O | H |
| H | $OCH_3$ | H | n-hexyl | O | H |
| H | $OCH_3$ | H | 2-hexyl | O | H |
| H | $OCH_3$ | H | 3-hexyl | O | H |
| H | $OCH_3$ | H | 2-methyl-2-pentyl | O | H |
| H | $OCH_3$ | H | cyclo-propylmethyl | O | H |
| H | $OCH_3$ | H | cyclo-butyl | O | H |
| H | $OCH_3$ | H | cyclo-pentyl | O | H |
| H | $OCH_3$ | H | cyclo-hexyl | O | H |
| H | $OCH_3$ | H | 1-methylcyclohexyl | O | H |
| H | $OCH_3$ | H | 3-trifluoromethylcyclohexyl | O | H |
| H | $OCH_3$ | H | allyl | O | H |
| H | $OCH_3$ | H | 1-buten-3-yl | O | H |

TABLE-continued

Ia/IA, Ib/IB, Ic/IC structures

| R³ | R⁴ | R¹ | R² | Y | R⁶ |
|---|---|---|---|---|---|
| H | OCH₃ | H | crotyl | O | H |
| H | OCH₃ | H | propargyl | O | H |
| H | OCH₃ | H | 1-butyn-3-yl | O | H |
| H | OCH₃ | H | 3-methyl-1-butyn-3-yl | O | H |
| H | OCH₃ | H | 2-pentyn-4-yl | O | H |
| H | OCH₃ | H | benzyl | O | H |
| H | OCH₃ | H | 2-phenylethyl | O | H |
| H | OCH₃ | H | 2-methylthioethyl | O | H |
| H | OCH₃ | H | 2-chloroethyl | O | H |
| H | OCH₃ | H | 2-methoxyethyl | O | H |
| H | OCH₃ | H | 2-(N,N-dimethylamino)ethyl | O | H |
| H | OCH₃ | H | phenyl | O | H |
| H | OCH₃ | H | 2-CH₃-phenyl | O | H |
| H | OCH₃ | H | 3-CH₃-phenyl | O | H |
| H | OCH₃ | H | 4-CH₃-phenyl | O | H |
| H | OCH₃ | H | 2,4-(CH₃,CH₃)-phenyl | O | H |
| H | OCH₃ | H | 2,3,5-(CH₃,CH₃,CH₃)-phenyl | O | H |
| H | OCH₃ | H | 3-CF₃-phenyl | O | H |
| H | OCH₃ | H | 3-F-phenyl | O | H |
| H | OCH₃ | H | 2-Cl-phenyl | O | H |
| H | OCH₃ | H | 4-Cl-phenyl | O | H |
| H | OCH₃ | H | 2,4-(F,F)-phenyl | O | H |
| H | OCH₃ | H | 2,3,5-(Cl,Cl,Cl)-phenyl | O | H |
| H | OCH₃ | H | 2-CN-phenyl | O | H |
| H | OCH₃ | H | 2-OCH₃-phenyl | O | H |
| H | OCH₃ | H | 2,3-(OCH₃,OCH₃)-phenyl | O | H |
| H | OCH₃ | H | 3,4,5-(OCH₃,OCH₃,OCH₃)-phenyl | O | H |
| H | OCH₃ | H | 3-OCF₃-phenyl | O | H |
| H | OCH₃ | H | 3-OCF₂OHF₂-phenyl | O | H |
| H | OCH₃ | H | 4-OCF₂CHF₂-phenyl | O | H |
| H | OCH₃ | H | 2-SCH₃-phenyl | O | H |
| H | OCH₃ | H | 2,4-(SCH₃,SCH₃)-phenyl | O | H |
| H | OCH₃ | H | 2-SCF₃-phenyl | O | H |
| H | OCH₃ | H | 4-NO₂-phenyl | O | H |
| H | OCH₃ | H | 2,4-(NO₂,NO₂)-phenyl | O | H |
| H | OCH₃ | H | 3-COCH₃-phenyl | O | H |
| H | OCH₃ | H | 3-COCF₃-phenyl | O | H |
| H | OCH₃ | H | 1-naphthyl | O | H |
| H | OCH₃ | H | 2-naphthyl | O | H |
| H | OCH₃ | H | piperidino | O | H |
| H | OCH₃ | H | 3-tetrahydrofuranyl | O | H |
| H | OCH₃ | H | 4-tetrahydropyranyl | O | H |
| H | OCH₃ | H | 2-thiazolyl | O | H |
| H | OCH₃ | H | 5-CH₃-2-thiazolyl | O | H |
| H | OCH₃ | H | 4-CH₃-5-COOH-2-thiazolyl | O | H |
| OCH₃ | H | H | methyl | O | H |
| OCH₃ | H | H | ethyl | O | H |
| OCH₃ | H | H | n-propyl | O | H |
| OCH₃ | H | H | iso-propyl | O | H |
| OCH₃ | H | H | cyclopropyl | O | H |
| OCH₃ | H | H | n-butyl | O | H |
| OCH₃ | H | H | iso-butyl | O | H |
| OCH₃ | H | H | sec.-butyl | O | H |
| OCH₃ | H | H | tert.-butyl | O | H |
| OCH₃ | H | H | n-pentyl | O | H |
| OCH₃ | H | H | 2-pentyl | O | H |
| OCH₃ | H | H | 3-pentyl | O | H |
| OCH₃ | H | H | n-hexyl | O | H |
| OCH₃ | H | H | 2-hexyl | O | H |
| OCH₃ | H | H | 3-hexyl | O | H |
| OCH₃ | H | H | 2-methyl-2-pentyl | O | H |
| OCH₃ | H | H | cyclo-propylmethyl | O | H |
| OCH₃ | H | H | cyclo-butyl | O | H |
| OCH₃ | H | H | cyclo-pentyl | O | H |
| OCH₃ | H | H | cyclo-hexyl | O | H |
| OCH₃ | H | H | 1-methylcyclohexyl | O | H |
| OCH₃ | H | H | 3-trifluoromethylcyclohexyl | O | H |
| OCH₃ | H | H | allyl | O | H |
| OCH₃ | H | H | 1-buten-3-yl | O | H |
| OCH₃ | H | H | crotyl | O | H |
| OCH₃ | H | H | propargyl | O | H |

TABLE-continued

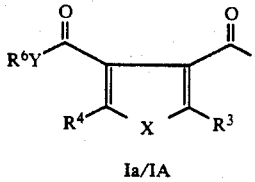

Ia/IA    Ib/IB    Ic/IC

| R³ | R⁴ | R¹ | R² | Y | R⁶ |
|---|---|---|---|---|---|
| OCH₃ | H | H | 1-butyn-3-yl | O | H |
| OCH₃ | H | H | 3-methyl-1-butyn-3-yl | O | H |
| OCH₃ | H | H | 2-pentyn-4-yl | O | H |
| OCH₃ | H | H | benzyl | O | H |
| OCH₃ | H | H | 2-phenylethyl | O | H |
| OCH₃ | H | H | 2-methylthioethyl | O | H |
| OCH₃ | H | H | 2-chloroethyl | O | H |
| OCH₃ | H | H | 2-methoxyethyl | O | H |
| OCH₃ | H | H | 2-(N,N-dimethylamino)ethyl | O | H |
| OCH₃ | H | H | phenyl | O | H |
| OCH₃ | H | H | 2-CH₃-phenyl | O | H |
| OCH₃ | H | H | 3-CH₃-phenyl | O | H |
| OCH₃ | H | H | 4-CH₃-phenyl | O | H |
| OCH₃ | H | H | 2,4-(CH₃,CH₃)-phenyl | O | H |
| OCH₃ | H | H | 2,3,5-(CH₃,CH₃,CH₃)-phenyl | O | H |
| OCH₃ | H | H | 3-CF₃-phenyl | O | H |
| OCH₃ | H | H | 3-F-phenyl | O | H |
| OCH₃ | H | H | 2-Cl-phenyl | O | H |
| OCH₃ | H | H | 4-Cl-phenyl | O | H |
| OCH₃ | H | H | 2,4-(F,F)-phenyl | O | H |
| OCH₃ | H | H | 2,3,5-(Cl,Cl,Cl)-phenyl | O | H |
| OCH₃ | H | H | 2-CN-phenyl | O | H |
| OCH₃ | H | H | 2-OCH₃-phenyl | O | H |
| OCH₃ | H | H | 2,3-(OCH₃,OCH₃)-phenyl | O | H |
| OCH₃ | H | H | 3,4,5-(OCH₃,OCH₃,OCH₃)-phenyl | O | H |
| OCH₃ | H | H | 3-OCF₃-phenyl | O | H |
| OCH₃ | H | H | 3-OCF₂OHF₂-phenyl | O | H |
| OCH₃ | H | H | 4-OCF₂CHF₂-phenyl | O | H |
| OCH₃ | H | H | 2-SCH₃-phenyl | O | H |
| OCH₃ | H | H | 2,4-(SCH₃,SCH₃)-phenyl | O | H |
| OCH₃ | H | H | 2-SCF₃-phenyl | O | H |
| OCH₃ | H | H | 4-NO₂-phenyl | O | H |
| OCH₃ | H | H | 2,4-(NO₂,NO₂)-phenyl | O | H |
| OCH₃ | H | H | 3-COCH₃-phenyl | O | H |
| OCH₃ | H | H | 3-COCF₃-phenyl | O | H |
| OCH₃ | H | H | 1-naphthyl | O | H |
| OCH₃ | H | H | 2-naphthyl | O | H |
| OCH₃ | H | H | piperidino | O | H |
| OCH₃ | H | H | 3-tetrahydrofuranyl | O | H |
| OCH₃ | H | H | 4-tetrahydropyranyl | O | H |
| OCH₃ | H | H | 2-thiazolyl | O | H |
| OCH₃ | H | H | 5-CH₃-2-thiazolyl | O | H |
| OCH₃ | H | H | 4-CH₃-5-COOH-2-thiazolyl | O | H |
| H | CH₃ | H | methyl | O | H |
| H | CH₃ | H | ethyl | O | H |
| H | CH₃ | H | n-propyl | O | H |
| H | CH₃ | H | iso-propyl | O | H |
| H | CH₃ | H | cyclopropyl | O | H |
| H | CH₃ | H | n-butyl | O | H |
| H | CH₃ | H | iso-butyl | O | H |
| H | CH₃ | H | sec.-butyl | O | H |
| H | CH₃ | H | tert.-butyl | O | H |
| H | CH₃ | H | n-pentyl | O | H |
| H | CH₃ | H | 2-pentyl | O | H |
| H | CH₃ | H | 3-pentyl | O | H |
| H | CH₃ | H | n-hexyl | O | H |
| H | CH₃ | H | 2-hexyl | O | H |
| H | CH₃ | H | 3-hexyl | O | H |
| H | CH₃ | H | 2-methyl-2-pentyl | O | H |
| H | CH₃ | H | cyclo-propylmethyl | O | H |
| H | CH₃ | H | cyclo-butyl | O | H |
| H | CH₃ | H | cyclo-pentyl | O | H |
| H | CH₃ | H | cyclo-hexyl | O | H |
| H | CH₃ | H | 1-methylcyclohexyl | O | H |
| H | CH₃ | H | 3-trifluoromethylcyclohexyl | O | H |
| H | CH₃ | H | allyl | O | H |
| H | CH₃ | H | 1-buten-3-yl | O | H |
| H | CH₃ | H | crotyl | O | H |
| H | CH₃ | H | propargyl | O | H |
| H | CH₃ | H | 1-butyn-3-yl | O | H |
| H | CH₃ | H | 3-methyl-1-butyn-3-yl | O | H |

TABLE-continued

| | Ia/IA | | Ib/IB | | Ic/IC | |
|---|---|---|---|---|---|---|
| R³ | R⁴ | R¹ | R² | | Y | R⁶ |
| H | CH₃ | H | 2-pentyn-4-yl | | O | H |
| H | CH₃ | H | benzyl | | O | H |
| H | CH₃ | H | 2-phenylethyl | | O | H |
| H | CH₃ | H | 2-methylthioethyl | | O | H |
| H | CH₃ | H | 2-chloroethyl | | O | H |
| H | CH₃ | H | 2-methoxyethyl | | O | H |
| H | CH₃ | H | 2-(N,N-dimethylamino)ethyl | | O | H |
| H | CH₃ | H | phenyl | | O | H |
| H | CH₃ | H | 2-CH₃-phenyl | | O | H |
| H | CH₃ | H | 3-CH₃-phenyl | | O | H |
| H | CH₃ | H | 4-CH₃-phenyl | | O | H |
| H | CH₃ | H | 2,4-(CH₃,CH₃)-phenyl | | O | H |
| H | CH₃ | H | 2,3,5-(CH₃,CH₃,CH₃)-phenyl | | O | H |
| H | CH₃ | H | 3-CF₃-phenyl | | O | H |
| H | CH₃ | H | 3-F-phenyl | | O | H |
| H | CH₃ | H | 2-Cl-phenyl | | O | H |
| H | CH₃ | H | 4-Cl-phenyl | | O | H |
| H | CH₃ | H | 2,4-(F,F)-phenyl | | O | H |
| H | CH₃ | H | 2,3,5-(Cl,Cl,Cl)-phenyl | | O | H |
| H | CH₃ | H | 2-CN-phenyl | | O | H |
| H | CH₃ | H | 2-OCH₃-phenyl | | O | H |
| H | CH₃ | H | 2,3-(OCH₃,OCH₃)-phenyl | | O | H |
| H | CH₃ | H | 3,4,5-(OCH₃,OCH₃,OCH₃)-phenyl | | O | H |
| H | CH₃ | H | 3-OCF₃-phenyl | | O | H |
| H | CH₃ | H | 3-OCF₂OHF₂-phenyl | | O | H |
| H | CH₃ | H | 4-OCF₂CHF₂-phenyl | | O | H |
| H | CH₃ | H | 2-SCH₃-phenyl | | O | H |
| H | CH₃ | H | 2,4-(SCH₃,SCH₃)-phenyl | | O | H |
| H | CH₃ | H | 2-SCF₃-phenyl | | O | H |
| H | CH₃ | H | 4-NO₂-phenyl | | O | H |
| H | CH₃ | H | 2,4-(NO₂,NO₂)-phenyl | | O | H |
| H | CH₃ | H | 3-COCH₃-phenyl | | O | H |
| H | CH₃ | H | 3-COCF₃-phenyl | | O | H |
| H | CH₃ | H | 1-naphthyl | | O | H |
| H | CH₃ | H | 2-naphthyl | | O | H |
| H | CH₃ | H | piperidino | | O | H |
| H | CH₃ | H | 3-tetrahydrofuranyl | | O | H |
| H | CH₃ | H | 4-tetrahydropyranyl | | O | H |
| H | CH₃ | H | 2-thiazolyl | | O | H |
| H | CH₃ | H | 5-CH₃-2-thiazolyl | | O | H |
| H | CH₃ | H | 4-CH₃-5-COOH-2-thiazolyl | | O | H |
| CH₃ | H | H | methyl | | O | H |
| CH₃ | H | H | ethyl | | O | H |
| CH₃ | H | H | n-propyl | | O | H |
| CH₃ | H | H | iso-propyl | | O | H |
| CH₃ | H | H | cyclopropyl | | O | H |
| CH₃ | H | H | n-butyl | | O | H |
| CH₃ | H | H | iso-butyl | | O | H |
| CH₃ | H | H | sec.-butyl | | O | H |
| CH₃ | H | H | tert.-butyl | | O | H |
| CH₃ | H | H | n-pentyl | | O | H |
| CH₃ | H | H | 2-pentyl | | O | H |
| CH₃ | H | H | 3-pentyl | | O | H |
| CH₃ | H | H | n-hexyl | | O | H |
| CH₃ | H | H | 2-hexyl | | O | H |
| CH₃ | H | H | 3-hexyl | | O | H |
| CH₃ | H | H | 2-methyl-2-pentyl | | O | H |
| CH₃ | H | H | cyclo-propylmethyl | | O | H |
| CH₃ | H | H | cyclo-butyl | | O | H |
| CH₃ | H | H | cyclo-pentyl | | O | H |
| CH₃ | H | H | cyclo-hexyl | | O | H |
| CH₃ | H | H | 1-methylcyclohexyl | | O | H |
| CH₃ | H | H | 3-trifluoromethylcyclohexyl | | O | H |
| CH₃ | H | H | allyl | | O | H |
| CH₃ | H | H | 1-buten-3-yl | | O | H |
| CH₃ | H | H | crotyl | | O | H |
| CH₃ | H | H | propargyl | | O | H |
| CH₃ | H | H | 1-butyn-3-yl | | O | H |
| CH₃ | H | H | 3-methyl-1-butyn-3-yl | | O | H |
| CH₃ | H | H | 2-pentyn-4-yl | | O | H |
| CH₃ | H | H | benzyl | | O | H |

TABLE-continued

Structures Ia/IA, Ib/IB, Ic/IC (thiophene/furan derivatives with R⁶Y-C(O)-, -C(O)-NR¹R², R³, R⁴, X substituents)

| R³ | R⁴ | R¹ | R² | Y | R⁶ |
|---|---|---|---|---|---|
| CH₃ | H | H | 2-phenylethyl | O | H |
| CH₃ | H | H | 2-methylthioethyl | O | H |
| CH₃ | H | H | 2-chloroethyl | O | H |
| CH₃ | H | H | 2-methoxyethyl | O | H |
| CH₃ | H | H | 2-(N,N-dimethylamino)ethyl | O | H |
| CH₃ | H | H | phenyl | O | H |
| CH₃ | H | H | 2-CH₃-phenyl | O | H |
| CH₃ | H | H | 3-CH₃-phenyl | O | H |
| CH₃ | H | H | 4-CH₃-phenyl | O | H |
| CH₃ | H | H | 2,4-(CH₃,CH₃)-phenyl | O | H |
| CH₃ | H | H | 2,3,5-(CH₃,CH₃,CH₃)-phenyl | O | H |
| CH₃ | H | H | 3-CF₃-phenyl | O | H |
| CH₃ | H | H | 3-F-phenyl | O | H |
| CH₃ | H | H | 2-Cl-phenyl | O | H |
| CH₃ | H | H | 4-Cl-phenyl | O | H |
| CH₃ | H | H | 2,4-(F,F)-phenyl | O | H |
| CH₃ | H | H | 2,3,5-(Cl,Cl,Cl)-phenyl | O | H |
| CH₃ | H | H | 2-CN-phenyl | O | H |
| CH₃ | H | H | 2-OCH₃-phenyl | O | H |
| CH₃ | H | H | 2,3-(OCH₃,OCH₃)-phenyl | O | H |
| CH₃ | H | H | 3,4,5-(OCH₃,OCH₃,OCH₃)-phenyl | O | H |
| CH₃ | H | H | 3-OCF₃-phenyl | O | H |
| CH₃ | H | H | 3-OCF₂OHF₂-phenyl | O | H |
| CH₃ | H | H | 4-OCF₂CHF₂-phenyl | O | H |
| CH₃ | H | H | 2-SCH₃-phenyl | O | H |
| CH₃ | H | H | 2,4-(SCH₃,SCH₃)-phenyl | O | H |
| CH₃ | H | H | 2-SCF₃-phenyl | O | H |
| CH₃ | H | H | 4-NO₂-phenyl | O | H |
| CH₃ | H | H | 2,4-(NO₂,NO₂)-phenyl | O | H |
| CH₃ | H | H | 3-COCH₃-phenyl | O | H |
| CH₃ | H | H | 3-COCF₃-phenyl | O | H |
| CH₃ | H | H | 1-naphthyl | O | H |
| CH₃ | H | H | 2-naphthyl | O | H |
| CH₃ | H | H | piperidino | O | H |
| CH₃ | H | H | 3-tetrahydrofuranyl | O | H |
| CH₃ | H | H | 4-tetrahydropyranyl | O | H |
| CH₃ | H | H | 2-thiazolyl | O | H |
| CH₃ | H | H | 5-CH₃-2-thiazolyl | O | H |
| CH₃ | H | H | 4-CH₃-5-COOH-2-thiazolyl | O | H |
| CH₃ | CH₃ | H | methyl | O | H |
| CH₃ | CH₃ | H | ethyl | O | H |
| CH₃ | CH₃ | H | n-propyl | O | H |
| CH₃ | CH₃ | H | iso-propyl | O | H |
| CH₃ | CH₃ | H | cyclopropyl | O | H |
| CH₃ | CH₃ | H | n-butyl | O | H |
| CH₃ | CH₃ | H | iso-butyl | O | H |
| CH₃ | CH₃ | H | sec.-butyl | O | H |
| CH₃ | CH₃ | H | tert.-butyl | O | H |
| CH₃ | CH₃ | H | n-pentyl | O | H |
| CH₃ | CH₃ | H | 2-pentyl | O | H |
| CH₃ | CH₃ | H | 3-pentyl | O | H |
| CH₃ | CH₃ | H | n-hexyl | O | H |
| CH₃ | CH₃ | H | 2-hexyl | O | H |
| CH₃ | CH₃ | H | 3-hexyl | O | H |
| CH₃ | CH₃ | H | 2-methyl-2-pentyl | O | H |
| CH₃ | CH₃ | H | cyclo-propylmethyl | O | H |
| CH₃ | CH₃ | H | cyclo-butyl | O | H |
| CH₃ | CH₃ | H | cyclo-pentyl | O | H |
| CH₃ | CH₃ | H | cyclo-hexyl | O | H |
| CH₃ | CH₃ | H | 1-methylcyclohexyl | O | H |
| CH₃ | CH₃ | H | 3-trifluoromethylcyclohexyl | O | H |
| CH₃ | CH₃ | H | allyl | O | H |
| CH₃ | CH₃ | H | 1-buten-3-yl | O | H |
| CH₃ | CH₃ | H | crotyl | O | H |
| CH₃ | CH₃ | H | propargyl | O | H |
| CH₃ | CH₃ | H | 1-butyn-3-yl | O | H |
| CH₃ | CH₃ | H | 3-methyl-1-butyn-3-yl | O | H |
| CH₃ | CH₃ | H | 2-pentyn-4-yl | O | H |
| CH₃ | CH₃ | H | benzyl | O | H |
| CH₃ | CH₃ | H | 2-phenylethyl | O | H |
| CH₃ | CH₃ | H | 2-methylthioethyl | O | H |

TABLE-continued

| | Ia/IA | | | Ib/IB | | Ic/IC | |
|---|---|---|---|---|---|---|---|

| $R^3$ | $R^4$ | $R^1$ | $R^2$ | Y | $R^6$ |
|---|---|---|---|---|---|
| $CH_3$ | $CH_3$ | H | 2-chloroethyl | O | H |
| $CH_3$ | $CH_3$ | H | 2-methoxyethyl | O | H |
| $CH_3$ | $CH_3$ | H | 2-(N,N-dimethylamino)ethyl | O | H |
| $CH_3$ | $CH_3$ | H | phenyl | O | H |
| $CH_3$ | $CH_3$ | H | 2-$CH_3$-phenyl | O | H |
| $CH_3$ | $CH_3$ | H | 3-$CH_3$-phenyl | O | H |
| $CH_3$ | $CH_3$ | H | 4-$CH_3$-phenyl | O | H |
| $CH_3$ | $CH_3$ | H | 2,4-($CH_3$,$CH_3$)-phenyl | O | H |
| $CH_3$ | $CH_3$ | H | 2,3,5-($CH_3$,$CH_3CH_3$)-phenyl | O | H |
| $CH_3$ | $CH_3$ | H | 3-$CF_3$-phenyl | O | H |
| $CH_3$ | $CH_3$ | H | 3-F-phenyl | O | H |
| $CH_3$ | $CH_3$ | H | 2-Cl-phenyl | O | H |
| $CH_3$ | $CH_3$ | H | 4-Cl-phenyl | O | H |
| $CH_3$ | $CH_3$ | H | 2,4-(F,F)-phenyl | O | H |
| $CH_3$ | $CH_3$ | H | 2,3,5-(Cl,Cl,Cl)-phenyl | O | H |
| $CH_3$ | $CH_3$ | H | 2-CN-phenyl | O | H |
| $CH_3$ | $CH_3$ | H | 2-$OCH_3$-phenyl | O | H |
| $CH_3$ | $CH_3$ | H | 2,3-($OCH_3$,$OCH_3$)-phenyl | O | H |
| $CH_3$ | $CH_3$ | H | 3,4,5-($OCH_3$,$OCH_3$,$OCH_3$)-phenyl | O | H |
| $CH_3$ | $CH_3$ | H | 3-$OCF_3$-phenyl | O | H |
| $CH_3$ | $CH_3$ | H | 3-$OCF_2OHF_2$-phenyl | O | H |
| $CH_3$ | $CH_3$ | H | 4-$OCF_2CHF_2$-phenyl | O | H |
| $CH_3$ | $CH_3$ | H | 2-$SCH_3$-phenyl | O | H |
| $CH_3$ | $CH_3$ | H | 2,4-($SCH_3$,$SCH_3$)-phenyl | O | H |
| $CH_3$ | $CH_3$ | H | 2-$SCF_3$-phenyl | O | H |
| $CH_3$ | $CH_3$ | H | 4-$NO_2$-phenyl | O | H |
| $CH_3$ | $CH_3$ | H | 2,4-($NO_2$,$NO_2$)-phenyl | O | H |
| $CH_3$ | $CH_3$ | H | 3-$COCH_3$-phenyl | O | H |
| $CH_3$ | $CH_3$ | H | 3-$COCF_3$-phenyl | O | H |
| $CH_3$ | $CH_3$ | H | 1-naphthyl | O | H |
| $CH_3$ | $CH_3$ | H | 2-naphthyl | O | H |
| $CH_3$ | $CH_3$ | H | piperidino | O | H |
| $CH_3$ | $CH_3$ | H | 3-tetrahydrofuranyl | O | H |
| $CH_3$ | $CH_3$ | H | 4-tetrahydropyranyl | O | H |
| $CH_3$ | $CH_3$ | H | 2-thiazolyl | O | H |
| $CH_3$ | $CH_3$ | H | 5-$CH_3$-2-thiazolyl | O | H |
| $CH_3$ | $CH_3$ | H | 4-$CH_3$-5-COOH-2-thiazolyl | O | H |
| H | $CH(CH_3)_2$ | H | methyl | O | H |
| H | $CH(CH_3)_2$ | H | ethyl | O | H |
| H | $CH(CH_3)_2$ | H | n-propyl | O | H |
| H | $CH(CH_3)_2$ | H | iso-propyl | O | H |
| H | $CH(CH_3)_2$ | H | cyclopropyl | O | H |
| H | $CH(CH_3)_2$ | H | n-butyl | O | H |
| H | $CH(CH_3)_2$ | H | iso-butyl | O | H |
| H | $CH(CH_3)_2$ | H | sec.-butyl | O | H |
| H | $CH(CH_3)_2$ | H | tert.-butyl | O | H |
| H | $CH(CH_3)_2$ | H | n-pentyl | O | H |
| H | $CH(CH_3)_2$ | H | 2-pentyl | O | H |
| H | $CH(CH_3)_2$ | H | 3-pentyl | O | H |
| H | $CH(CH_3)_2$ | H | n-hexyl | O | H |
| H | $CH(CH_3)_2$ | H | 2-hexyl | O | H |
| H | $CH(CH_3)_2$ | H | 3-hexyl | O | H |
| H | $CH(CH_3)_2$ | H | 2-methyl-2-pentyl | O | H |
| H | $CH(CH_3)_2$ | H | cyclo-propylmethyl | O | H |
| H | $CH(CH_3)_2$ | H | cyclo-butyl | O | H |
| H | $CH(CH_3)_2$ | H | cyclo-pentyl | O | H |
| H | $CH(CH_3)_2$ | H | cyclo-hexyl | O | H |
| H | $CH(CH_3)_2$ | H | 1-methylcyclohexyl | O | H |
| H | $CH(CH_3)_2$ | H | 3-trifluoromethylcyclohexyl | O | H |
| H | $CH(CH_3)_2$ | H | allyl | O | H |
| H | $CH(CH_3)_2$ | H | 1-buten-3-yl | O | H |
| H | $CH(CH_3)_2$ | H | crotyl | O | H |
| H | $CH(CH_3)_2$ | H | propargyl | O | H |
| H | $CH(CH_3)_2$ | H | 1-butyn-3-yl | O | H |
| H | $CH(CH_3)_2$ | H | 3-methyl-1-butyn-3-yl | O | H |
| H | $CH(CH_3)_2$ | H | 2-pentyn-4-yl | O | H |
| H | $CH(CH_3)_2$ | H | benzyl | O | H |
| H | $CH(CH_3)_2$ | H | 2-phenylethyl | O | H |
| H | $CH(CH_3)_2$ | H | 2-methylthioethyl | O | H |
| H | $CH(CH_3)_2$ | H | 2-chloroethyl | O | H |
| H | $CH(CH_3)_2$ | H | 2-methoxyethyl | O | H |

TABLE-continued

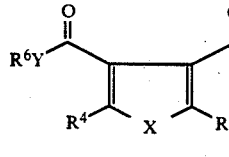

| | | | | | | |
|---|---|---|---|---|---|---|
| $R^3$ | $R^4$ | $R^1$ | $R^2$ | | Y | $R^6$ |
| H | CH(CH$_3$)$_2$ | H | 2-(N,N-dimethylamino)ethyl | | O | H |
| H | CH(CH$_3$)$_2$ | H | phenyl | | O | H |
| H | CH(CH$_3$)$_2$ | H | 2-CH$_3$-phenyl | | O | H |
| H | CH(CH$_3$)$_2$ | H | 3-CH$_3$-phenyl | | O | H |
| H | CH(CH$_3$)$_2$ | H | 4-CH$_3$-phenyl | | O | H |
| H | CH(CH$_3$)$_2$ | H | 2,4-(CH$_3$,CH$_3$)-phenyl | | O | H |
| H | CH(CH$_3$)$_2$ | H | 2,3,5-(CH$_3$,CH$_3$CH$_3$)-phenyl | | O | H |
| H | CH(CH$_3$)$_2$ | H | 3-CF$_3$-phenyl | | O | H |
| H | CH(CH$_3$)$_2$ | H | 3-F-phenyl | | O | H |
| H | CH(CH$_3$)$_2$ | H | 2-Cl-phenyl | | O | H |
| H | CH(CH$_3$)$_2$ | H | 4-Cl-phenyl | | O | H |
| H | CH(CH$_3$)$_2$ | H | 2,4-(F,F)-phenyl | | O | H |
| H | CH(CH$_3$)$_2$ | H | 2,3,5-(Cl,Cl,Cl)-phenyl | | O | H |
| H | CH(CH$_3$)$_2$ | H | 2-CN-phenyl | | O | H |
| H | CH(CH$_3$)$_2$ | H | 2-OCH$_3$-phenyl | | O | H |
| H | CH(CH$_3$)$_2$ | H | 2,3-(OCH$_3$,OCH$_3$)-phenyl | | O | H |
| H | CH(CH$_3$)$_2$ | H | 3,4,5-(OCH$_3$,OCH$_3$,OCH$_3$)-phenyl | | O | H |
| H | CH(CH$_3$)$_2$ | H | 3-OCF$_3$-phenyl | | O | H |
| H | CH(CH$_3$)$_2$ | H | 3-OCF$_2$OHF$_2$-phenyl | | O | H |
| H | CH(CH$_3$)$_2$ | H | 4-OCF$_2$CHF$_2$-phenyl | | O | H |
| H | CH(CH$_3$)$_2$ | H | 2-SCH$_3$-phenyl | | O | H |
| H | CH(CH$_3$)$_2$ | H | 2,4-(SCH$_3$,SCH$_3$)-phenyl | | O | H |
| H | CH(CH$_3$)$_2$ | H | 2-SCF$_3$-phenyl | | O | H |
| H | CH(CH$_3$)$_2$ | H | 4-NO$_2$-phenyl | | O | H |
| H | CH(CH$_3$)$_2$ | H | 2,4-(NO$_2$,NO$_2$)-phenyl | | O | H |
| H | CH(CH$_3$)$_2$ | H | 3-COCH$_3$-phenyl | | O | H |
| H | CH(CH$_3$)$_2$ | H | 3-COCF$_3$-phenyl | | O | H |
| H | CH(CH$_3$)$_2$ | H | 1-naphthyl | | O | H |
| H | CH(CH$_3$)$_2$ | H | 2-naphthyl | | O | H |
| H | CH(CH$_3$)$_2$ | H | piperidino | | O | H |
| H | CH(CH$_3$)$_2$ | H | 3-tetrahydrofuranyl | | O | H |
| H | CH(CH$_3$)$_2$ | H | 4-tetrahydropyranyl | | O | H |
| H | CH(CH$_3$)$_2$ | H | 2-thiazolyl | | O | H |
| H | CH(CH$_3$)$_2$ | H | 5-CH$_3$-2-thiazolyl | | O | H |
| H | CH(CH$_3$)$_2$ | H | 4-CH$_3$-5-COOH-2-thiazolyl | | O | H |
| OCH(CH$_3$)$_2$ | H | H | methyl | | O | H |
| OCH(CH$_3$)$_2$ | H | H | ethyl | | O | H |
| OCH(CH$_3$)$_2$ | H | H | n-propyl | | O | H |
| OCH(CH$_3$)$_2$ | H | H | iso-propyl | | O | H |
| OCH(CH$_3$)$_2$ | H | H | cyclopropyl | | O | H |
| OCH(CH$_3$)$_2$ | H | H | n-butyl | | O | H |
| OCH(CH$_3$)$_2$ | H | H | iso-butyl | | O | H |
| OCH(CH$_3$)$_2$ | H | H | sec.-butyl | | O | H |
| OCH(CH$_3$)$_2$ | H | H | tert.-butyl | | O | H |
| OCH(CH$_3$)$_2$ | H | H | n-pentyl | | O | H |
| OCH(CH$_3$)$_2$ | H | H | 2-pentyl | | O | H |
| OCH(CH$_3$)$_2$ | H | H | 3-pentyl | | O | H |
| OCH(CH$_3$)$_2$ | H | H | n-hexyl | | O | H |
| OCH(CH$_3$)$_2$ | H | H | 2-hexyl | | O | H |
| OCH(CH$_3$)$_2$ | H | H | 3-hexyl | | O | H |
| OCH(CH$_3$)$_2$ | H | H | 2-methyl-2-pentyl | | O | H |
| OCH(CH$_3$)$_2$ | H | H | cyclo-propylmethyl | | O | H |
| OCH(CH$_3$)$_2$ | H | H | cyclo-butyl | | O | H |
| OCH(CH$_3$)$_2$ | H | H | cyclo-pentyl | | O | H |
| OCH(CH$_3$)$_2$ | H | H | cyclo-hexyl | | O | H |
| OCH(CH$_3$)$_2$ | H | H | 1-methylcyclohexyl | | O | H |
| OCH(CH$_3$)$_2$ | H | H | 3-trifluoromethylcyclohexyl | | O | H |
| OCH(CH$_3$)$_2$ | H | H | allyl | | O | H |
| OCH(CH$_3$)$_2$ | H | H | 1-buten-3-yl | | O | H |
| OCH(CH$_3$)$_2$ | H | H | crotyl | | O | H |
| OCH(CH$_3$)$_2$ | H | H | propargyl | | O | H |
| OCH(CH$_3$)$_2$ | H | H | 1-butyn-3-yl | | O | H |
| OCH(CH$_3$)$_2$ | H | H | 3-methyl-1-butyn-3-yl | | O | H |
| OCH(CH$_3$)$_2$ | H | H | 2-pentyn-4-yl | | O | H |
| OCH(CH$_3$)$_2$ | H | H | benzyl | | O | H |
| OCH(CH$_3$)$_2$ | H | H | 2-phenylethyl | | O | H |
| OCH(CH$_3$)$_2$ | H | H | 2-methylthioethyl | | O | H |
| OCH(CH$_3$)$_2$ | H | H | 2-chloroethyl | | O | H |
| OCH(CH$_3$)$_2$ | H | H | 2-methoxyethyl | | O | H |
| OCH(CH$_3$)$_2$ | H | H | 2-(N,N-dimethylamino)ethyl | | O | H |
| OCH(CH$_3$)$_2$ | H | H | phenyl | | O | H |

TABLE-continued

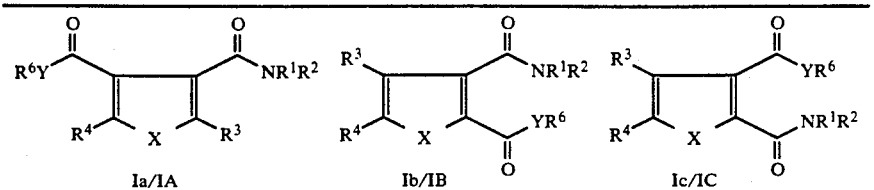

| R³ | R⁴ | R¹ | R² | Y | R⁶ |
|---|---|---|---|---|---|
| OCH(CH₃)₂ | H | H | 2-CH₃-phenyl | O | H |
| OCH(CH₃)₂ | H | H | 3-CH₃-phenyl | O | H |
| OCH(CH₃)₂ | H | H | 4-CH₃-phenyl | O | H |
| OCH(CH₃)₂ | H | H | 2,4-(CH₃,CH₃)-phenyl | O | H |
| OCH(CH₃)₂ | H | H | 2,3,5-(CH₃,CH₃CH₃)-phenyl | O | H |
| OCH(CH₃)₂ | H | H | 3-CF₃-phenyl | O | H |
| OCH(CH₃)₂ | H | H | 3-F-phenyl | O | H |
| OCH(CH₃)₂ | H | H | 2-Cl-phenyl | O | H |
| OCH(CH₃)₂ | H | H | 4-Cl-phenyl | O | H |
| OCH(CH₃)₂ | H | H | 2,4-(F,F)-phenyl | O | H |
| OCH(CH₃)₂ | H | H | 2,3,5-(Cl,Cl,Cl)-phenyl | O | H |
| OCH(CH₃)₂ | H | H | 2-CN-phenyl | O | H |
| OCH(CH₃)₂ | H | H | 2-OCH₃-phenyl | O | H |
| OCH(CH₃)₂ | H | H | 2,3-(OCH₃,OCH₃)-phenyl | O | H |
| OCH(CH₃)₂ | H | H | 3,4,5-(OCH₃,OCH₃,OCH₃)-phenyl | O | H |
| OCH(CH₃)₂ | H | H | 3-OCF₃-phenyl | O | H |
| OCH(CH₃)₂ | H | H | 3-OCF₂OHF₂-phenyl | O | H |
| OCH(CH₃)₂ | H | H | 4-OCF₂CHF₂-phenyl | O | H |
| OCH(CH₃)₂ | H | H | 2-SCH₃-phenyl | O | H |
| OCH(CH₃)₂ | H | H | 2,4-(SCH₃,SCH₃)-phenyl | O | H |
| OCH(CH₃)₂ | H | H | 2-SCF₃-phenyl | O | H |
| OCH(CH₃)₂ | H | H | 4-NO₂-phenyl | O | H |
| OCH(CH₃)₂ | H | H | 2,4-(NO₂,NO₂)-phenyl | O | H |
| OCH(CH₃)₂ | H | H | 3-COCH₃-phenyl | O | H |
| OCH(CH₃)₂ | H | H | 3-COCF₃-phenyl | O | H |
| OCH(CH₃)₂ | H | H | 1-naphthyl | O | H |
| OCH(CH₃)₂ | H | H | 2-naphthyl | O | H |
| OCH(CH₃)₂ | H | H | piperidino | O | H |
| OCH(CH₃)₂ | H | H | 3-tetrahydrofuranyl | O | H |
| OCH(CH₃)₂ | H | H | 4-tetrahydropyranyl | O | H |
| OCH(CH₃)₂ | H | H | 2-thiazolyl | O | H |
| OCH(CH₃)₂ | H | H | 5-CH₃-2-thiazolyl | O | H |
| OCH(CH₃)₂ | H | H | 4-CH₃-5-COOH-2-thiazolyl | O | H |
| H | Cl | H | methyl | O | 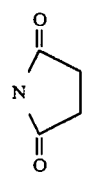 |
| H | Cl | H | ethyl | O | " |
| H | Cl | H | n-propyl | O | " |
| H | Cl | H | iso-propyl | O | " |
| H | Cl | H | cyclopropyl | O | " |
| H | Cl | H | n-butyl | O | " |
| H | Cl | H | iso-butyl | O | " |
| H | Cl | H | sec.-butyl | O | " |
| H | Cl | H | tert.-butyl | O | " |
| H | Cl | H | n-pentyl | O | " |
| H | Cl | H | 2-pentyl | O | " |
| H | Cl | H | 3-pentyl | O | " |
| H | Cl | H | n-hexyl | O | " |
| H | Cl | H | 2-hexyl | O | " |
| H | Cl | H | 3-hexyl | O | " |
| H | Cl | H | 2-methyl-2-pentyl | O | " |
| H | Cl | H | cyclo-propylmethyl | O | " |
| H | Cl | H | cyclo-butyl | O | " |
| H | Cl | H | cyclo-pentyl | O | " |
| H | Cl | H | cyclo-hexyl | O | " |
| H | Cl | H | 1-methylcyclohexyl | O | " |
| H | Cl | H | 3-trifluoromethylcyclohexyl | O | " |
| H | Cl | H | allyl | O | " |
| H | Cl | H | 1-buten-3-yl | O | " |
| H | Cl | H | crotyl | O | " |
| H | Cl | H | propargyl | O | " |
| H | Cl | H | 1-butyn-3-yl | O | " |
| H | Cl | H | 3-methyl-1-butyn-3-yl | O | " |
| H | Cl | H | 2-pentyn-4-yl | O | " |

TABLE-continued

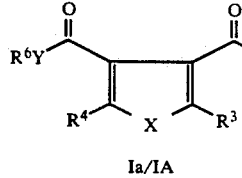

| | Ia/IA | | Ib/IB | | Ic/IC | |
|---|---|---|---|---|---|---|
| R³ | R⁴ | R¹ | R² | | Y | R⁶ |
| H | Cl | H | benzyl | | O | " |
| H | Cl | H | 2-phenylethyl | | O | " |
| H | Cl | H | 2-methylthioethyl | | O | " |
| H | Cl | H | 2-chloroethyl | | O | " |
| H | Cl | H | 2-methoxyethyl | | O | " |
| H | Cl | H | 2-(N,N-dimethylamino)ethyl | | O | " |
| H | Cl | H | phenyl | | O | " |
| H | Cl | H | 2-CH₃-phenyl | | O | " |
| H | Cl | H | 3-CH₃-phenyl | | O | " |
| H | Cl | H | 4-CH₃-phenyl | | O | " |
| H | Cl | H | 2,4-(CH₃,CH₃)-phenyl | | O | " |
| H | Cl | H | 2,3,5-(CH₃,CH₃CH₃)-phenyl | | O | " |
| H | Cl | H | 3-CF₃-phenyl | | O | " |
| H | Cl | H | 3-F-phenyl | | O | " |
| H | Cl | H | 2-Cl-phenyl | | O | " |
| H | Cl | H | 4-Cl-phenyl | | O | " |
| H | Cl | H | 2,4-(F,F)-phenyl | | O | " |
| H | Cl | H | 2,3,5-(Cl,Cl,Cl)-phenyl | | O | " |
| H | Cl | H | 2-CN-phenyl | | O | " |
| H | Cl | H | 2-OCH₃-phenyl | | O | " |
| H | Cl | H | 2,3-(OCH₃,OCH₃)-phenyl | | O | " |
| H | Cl | H | 3,4,5-(OCH₃,OCH₃,OCH₃)-phenyl | | O | " |
| H | Cl | H | 3-OCF₃-phenyl | | O | " |
| H | Cl | H | 3-OCF₂OHF₂-phenyl | | O | " |
| H | Cl | H | 4-OCF₂CHF₂-phenyl | | O | " |
| H | Cl | H | 2-SCH₃-phenyl | | O | " |
| H | Cl | H | 2,4-(SCH₃,SCH₃)-phenyl | | O | " |
| H | Cl | H | 2-SCF₃-phenyl | | O | " |
| H | Cl | H | 4-NO₂-phenyl | | O | " |
| H | Cl | H | 2,4-(NO₂,NO₂)-phenyl | | O | " |
| H | Cl | H | 3-COCH₃-phenyl | | O | " |
| H | Cl | H | 3-COCF₃-phenyl | | O | " |
| H | Cl | H | 1-naphthyl | | O | " |
| H | Cl | H | 2-naphthyl | | O | " |
| H | Cl | H | piperidino | | O | " |
| H | Cl | H | 3-tetrahydrofuranyl | | O | " |
| H | Cl | H | 4-tetrahydropyranyl | | O | " |
| H | Cl | H | 2-thiazolyl | | O | " |
| H | Cl | H | 5-CH₃-2-thiazolyl | | O | " |
| H | Cl | H | 4-CH₃-5-COOH-2-thiazolyl | | O | " |
| H | Cl | H | methyl | | O | N=C(CH₃)₂ |
| H | Cl | H | ethyl | | O | N=C(CH₃)₂ |
| H | Cl | H | n-propyl | | O | N=C(CH₃)₂ |
| H | Cl | H | iso-propyl | | O | N=C(CH₃)₂ |
| H | Cl | H | cyclopropyl | | O | N=C(CH₃)₂ |
| H | Cl | H | n-butyl | | O | N=C(CH₃)₂ |
| H | Cl | H | iso-butyl | | O | N=C(CH₃)₂ |
| H | Cl | H | sec.-butyl | | O | N=C(CH₃)₂ |
| H | Cl | H | tert.-butyl | | O | N=C(CH₃)₂ |
| H | Cl | H | n-pentyl | | O | N=C(CH₃)₂ |
| H | Cl | H | 2-pentyl | | O | N=C(CH₃)₂ |
| H | Cl | H | 3-pentyl | | O | N=C(CH₃)₂ |
| H | Cl | H | n-hexyl | | O | N=C(CH₃)₂ |
| H | Cl | H | 2-hexyl | | O | N=C(CH₃)₂ |
| H | Cl | H | 3-hexyl | | O | N=C(CH₃)₂ |
| H | Cl | H | 2-methyl-2-pentyl | | O | N=C(CH₃)₂ |
| H | Cl | H | cyclo-propylmethyl | | O | N=C(CH₃)₂ |
| H | Cl | H | cyclo-butyl | | O | N=C(CH₃)₂ |
| H | Cl | H | cyclo-pentyl | | O | N=C(CH₃)₂ |
| H | Cl | H | cyclo-hexyl | | O | N=C(CH₃)₂ |
| H | Cl | H | 1-methylcyclohexyl | | O | N=C(CH₃)₂ |
| H | Cl | H | 3-trifluoromethylcyclohexyl | | O | N=C(CH₃)₂ |
| H | Cl | H | allyl | | O | N=C(CH₃)₂ |
| H | Cl | H | 1-buten-3-yl | | O | N=C(CH₃)₂ |
| H | Cl | H | crotyl | | O | N=C(CH₃)₂ |
| H | Cl | H | propargyl | | O | N=C(CH₃)₂ |
| H | Cl | H | 1-butyn-3-yl | | O | N=C(CH₃)₂ |
| H | Cl | H | 3-methyl-1-butyn-3-yl | | O | N=C(CH₃)₂ |
| H | Cl | H | 2-pentyn-4-yl | | O | N=C(CH₃)₂ |
| H | Cl | H | benzyl | | O | N=C(CH₃)₂ |
| H | Cl | H | 2-phenylethyl | | O | N=C(CH₃)₂ |

TABLE-continued

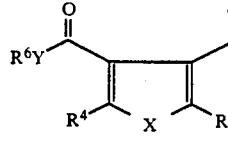
Ia/IA

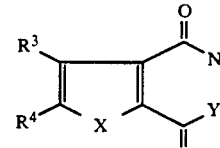
Ib/IB

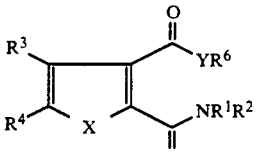
Ic/IC

| R³ | R⁴ | R¹ | R² | Y | R⁶ |
|---|---|---|---|---|---|
| H | Cl | H | 2-methylthioethyl | O | $N=C(CH_3)_2$ |
| H | Cl | H | 2-chloroethyl | O | $N=C(CH_3)_2$ |
| H | Cl | H | 2-methoxyethyl | O | $N=C(CH_3)_2$ |
| H | Cl | H | 2-(N,N-dimethylamino)ethyl | O | $N=C(CH_3)_2$ |
| H | Cl | H | phenyl | O | $N=C(CH_3)_2$ |
| H | Cl | H | 2-CH₃-phenyl | O | $N=C(CH_3)_2$ |
| H | Cl | H | 3-CH₃-phenyl | O | $N=C(CH_3)_2$ |
| H | Cl | H | 4-CH₃-phenyl | O | $N=C(CH_3)_2$ |
| H | Cl | H | 2,4-(CH₃,CH₃)-phenyl | O | $N=C(CH_3)_2$ |
| H | Cl | H | 2,3,5-(CH₃,CH₃CH₃)-phenyl | O | $N=C(CH_3)_2$ |
| H | Cl | H | 3-CF₃-phenyl | O | $N=C(CH_3)_2$ |
| H | Cl | H | 3-F-phenyl | O | $N=C(CH_3)_2$ |
| H | Cl | H | 2-Cl-phenyl | O | $N=C(CH_3)_2$ |
| H | Cl | H | 4-Cl-phenyl | O | $N=C(CH_3)_2$ |
| H | Cl | H | 2,4-(F,F)-phenyl | O | $N=C(CH_3)_2$ |
| H | Cl | H | 2,3,5-(Cl,Cl,Cl)-phenyl | O | $N=C(CH_3)_2$ |
| H | Cl | H | 2-CN-phenyl | O | $N=C(CH_3)_2$ |
| H | Cl | H | 2-OCH₃-phenyl | O | $N=C(CH_3)_2$ |
| H | Cl | H | 2,3-(OCH₃,OCH₃)-phenyl | O | $N=C(CH_3)_2$ |
| H | Cl | H | 3,4,5-(OCH₃,OCH₃,OCH₃)-phenyl | O | $N=C(CH_3)_2$ |
| H | Cl | H | 3-OCF₃-phenyl | O | $N=C(CH_3)_2$ |
| H | Cl | H | 3-OCF₂OHF₂-phenyl | O | $N=C(CH_3)_2$ |
| H | Cl | H | 4-OCF₂CHF₂-phenyl | O | $N=C(CH_3)_2$ |
| H | Cl | H | 2-SCH₃-phenyl | O | $N=C(CH_3)_2$ |
| H | Cl | H | 2,4-(SCH₃,SCH₃)-phenyl | O | $N=C(CH_3)_2$ |
| H | Cl | H | 2-SCF₃-phenyl | O | $N=C(CH_3)_2$ |
| H | Cl | H | 4-NO₂-phenyl | O | $N=C(CH_3)_2$ |
| H | Cl | H | 2,4-(NO₂,NO₂)-phenyl | O | $N=C(CH_3)_2$ |
| H | Cl | H | 3-COCH₃-phenyl | O | $N=C(CH_3)_2$ |
| H | Cl | H | 3-COCF₃-phenyl | O | $N=C(CH_3)_2$ |
| H | Cl | H | 1-naphthyl | O | $N=C(CH_3)_2$ |
| H | Cl | H | 2-naphthyl | O | $N=C(CH_3)_2$ |
| H | Cl | H | piperidino | O | $N=C(CH_3)_2$ |
| H | Cl | H | 3-tetrahydrofuranyl | O | $N=C(CH_3)_2$ |
| H | Cl | H | 4-tetrahydropyranyl | O | $N=C(CH_3)_2$ |
| H | Cl | H | 2-thiazolyl | O | $N=C(CH_3)_2$ |
| H | Cl | H | 5-CH₃-2-thiazolyl | O | $N=C(CH_3)_2$ |
| H | Cl | H | 4-CH₃-5-COOH-2-thiazolyl | O | $N=C(CH_3)_2$ |
| H | OCH₃ | H | methyl | O | 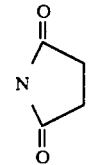 |
| H | OCH₃ | H | ethyl | O | " |
| H | OCH₃ | H | n-propyl | O | " |
| H | OCH₃ | H | iso-propyl | O | " |
| H | OCH₃ | H | cyclopropyl | O | " |
| H | OCH₃ | H | n-butyl | O | " |
| H | OCH₃ | H | iso-butyl | O | " |
| H | OCH₃ | H | sec.-butyl | O | " |
| H | OCH₃ | H | tert.-butyl | O | " |
| H | OCH₃ | H | n-pentyl | O | " |
| H | OCH₃ | H | 2-pentyl | O | " |
| H | OCH₃ | H | 3-pentyl | O | " |
| H | OCH₃ | H | n-hexyl | O | " |
| H | OCH₃ | H | 2-hexyl | O | " |
| H | OCH₃ | H | 3-hexyl | O | " |
| H | OCH₃ | H | 2-methyl-2-pentyl | O | " |
| H | OCH₃ | H | cyclo-propylmethyl | O | " |
| H | OCH₃ | H | cyclo-butyl | O | " |
| H | OCH₃ | H | cyclo-pentyl | O | " |
| H | OCH₃ | H | cyclo-hexyl | O | " |
| H | OCH₃ | H | 1-methylcyclohexyl | O | " |
| H | OCH₃ | H | 3-trifluoromethylcyclohexyl | O | " |
| H | OCH₃ | H | allyl | O | " |
| H | OCH₃ | H | 1-buten-3-yl | O | " |

TABLE-continued

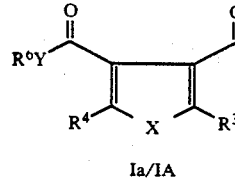

| R³ | R⁴ | R¹ | R² | Y | R⁶ |
|---|---|---|---|---|---|
| H | OCH₃ | H | crotyl | O | " |
| H | OCH₃ | H | propargyl | O | " |
| H | OCH₃ | H | 1-butyn-3-yl | O | " |
| H | OCH₃ | H | 3-methyl-1-butyn-3-yl | O | " |
| H | OCH₃ | H | 2-pentyn-4-yl | O | " |
| H | OCH₃ | H | benzyl | O | " |
| H | OCH₃ | H | 2-phenylethyl | O | " |
| H | OCH₃ | H | 2-methylthioethyl | O | " |
| H | OCH₃ | H | 2-chloroethyl | O | " |
| H | OCH₃ | H | 2-methoxyethyl | O | " |
| H | OCH₃ | H | 2-(N,N-dimethylamino)ethyl | O | " |
| H | OCH₃ | H | phenyl | O | " |
| H | OCH₃ | H | 2-CH₃-phenyl | O | " |
| H | OCH₃ | H | 3-CH₃-phenyl | O | " |
| H | OCH₃ | H | 4-CH₃-phenyl | O | " |
| H | OCH₃ | H | 2,4-(CH₃,CH₃)-phenyl | O | " |
| H | OCH₃ | H | 2,3,5-(CH₃,CH₃CH₃)-phenyl | O | " |
| H | OCH₃ | H | 3-CF₃-phenyl | O | " |
| H | OCH₃ | H | 3-F-phenyl | O | " |
| H | OCH₃ | H | 2-Cl-phenyl | O | " |
| H | OCH₃ | H | 4-Cl-phenyl | O | " |
| H | OCH₃ | H | 2,4-(F,F)-phenyl | O | " |
| H | OCH₃ | H | 2,3,5-(Cl,Cl,Cl)-phenyl | O | " |
| H | OCH₃ | H | 2-CN-phenyl | O | " |
| H | OCH₃ | H | 2-OCH₃-phenyl | O | " |
| H | OCH₃ | H | 2,3-(OCH₃,OCH₃)-phenyl | O | " |
| H | OCH₃ | H | 3,4,5-(OCH₃,OCH₃,OCH₃)-phenyl | O | " |
| H | OCH₃ | H | 3-OCF₃-phenyl | O | " |
| H | OCH₃ | H | 3-OCF₂OHF₂-phenyl | O | " |
| H | OCH₃ | H | 4-OCF₂CHF₂-phenyl | O | " |
| H | OCH₃ | H | 2-SCH₃-phenyl | O | " |
| H | OCH₃ | H | 2,4-(SCH₃,SCH₃)-phenyl | O | " |
| H | OCH₃ | H | 2-SCF₃-phenyl | O | " |
| H | OCH₃ | H | 4-NO₂-phenyl | O | " |
| H | OCH₃ | H | 2,4-(NO₂,NO₂)-phenyl | O | " |
| H | OCH₃ | H | 3-COCH₃-phenyl | O | " |
| H | OCH₃ | H | 3-COCF₃-phenyl | O | " |
| H | OCH₃ | H | 1-naphthyl | O | " |
| H | OCH₃ | H | 2-naphthyl | O | " |
| H | OCH₃ | H | piperidino | O | " |
| H | OCH₃ | H | 3-tetrahydrofuranyl | O | " |
| H | OCH₃ | H | 4-tetrahydropyranyl | O | " |
| H | OCH₃ | H | 2-thiazolyl | O | " |
| H | OCH₃ | H | 5-CH₃-2-thiazolyl | O | " |
| H | OCH₃ | H | 4-CH₃-5-COOH-2-thiazolyl | O | " |
| H | OCH₃ | H | methyl | O | N=C(CH₃)₂ |
| H | OCH₃ | H | ethyl | O | N=C(CH₃)₂ |
| H | OCH₃ | H | n-propyl | O | N=C(CH₃)₂ |
| H | OCH₃ | H | iso-propyl | O | N=C(CH₃)₂ |
| H | OCH₃ | H | cyclopropyl | O | N=C(CH₃)₂ |
| H | OCH₃ | H | n-butyl | O | N=C(CH₃)₂ |
| H | OCH₃ | H | iso-butyl | O | N=C(CH₃)₂ |
| H | OCH₃ | H | sec.-butyl | O | N=C(CH₃)₂ |
| H | OCH₃ | H | tert.-butyl | O | N=C(CH₃)₂ |
| H | OCH₃ | H | n-pentyl | O | N=C(CH₃)₂ |
| H | OCH₃ | H | 2-pentyl | O | N=C(CH₃)₂ |
| H | OCH₃ | H | 3-pentyl | O | N=C(CH₃)₂ |
| H | OCH₃ | H | n-hexyl | O | N=C(CH₃)₂ |
| H | OCH₃ | H | 2-hexyl | O | N=C(CH₃)₂ |
| H | OCH₃ | H | 3-hexyl | O | N=C(CH₃)₂ |
| H | OCH₃ | H | 2-methyl-2-pentyl | O | N=C(CH₃)₂ |
| H | OCH₃ | H | cyclo-propylmethyl | O | N=C(CH₃)₂ |
| H | OCH₃ | H | cyclo-butyl | O | N=C(CH₃)₂ |
| H | OCH₃ | H | cyclo-pentyl | O | N=C(CH₃)₂ |
| H | OCH₃ | H | cyclo-hexyl | O | N=C(CH₃)₂ |
| H | OCH₃ | H | 1-methylcyclohexyl | O | N=C(CH₃)₂ |
| H | OCH₃ | H | 3-trifluoromethylcyclohexyl | O | N=C(CH₃)₂ |
| H | OCH₃ | H | allyl | O | N=C(CH₃)₂ |
| H | OCH₃ | H | 1-buten-3-yl | O | N=C(CH₃)₂ |
| H | OCH₃ | H | crotyl | O | N=C(CH₃)₂ |
| H | OCH₃ | H | propargyl | O | N=C(CH₃)₂ |

TABLE-continued

Ia/IA: R⁶Y-C(=O)-C=C(-NR¹R²-C(=O))... with R⁴, X, R³
Ib/IB: R³, R⁴, X with C(=O)NR¹R² and YR⁶-C(=O)
Ic/IC: R³, R⁴, X with C(=O)YR⁶ and NR¹R²-C(=O)

| R³ | R⁴ | R¹ | R² | Y | R⁶ |
|---|---|---|---|---|---|
| H | OCH₃ | H | 1-butyn-3-yl | O | N=C(CH₃)₂ |
| H | OCH₃ | H | 3-methyl-1-butyn-3-yl | O | N=C(CH₃)₂ |
| H | OCH₃ | H | 2-pentyn-4-yl | O | N=C(CH₃)₂ |
| H | OCH₃ | H | benzyl | O | N=C(CH₃)₂ |
| H | OCH₃ | H | 2-phenylethyl | O | N=C(CH₃)₂ |
| H | OCH₃ | H | 2-methylthioethyl | O | N=C(CH₃)₂ |
| H | OCH₃ | H | 2-chloroethyl | O | N=C(CH₃)₂ |
| H | OCH₃ | H | 2-methoxyethyl | O | N=C(CH₃)₂ |
| H | OCH₃ | H | 2-(N,N-dimethylamino)ethyl | O | N=C(CH₃)₂ |
| H | OCH₃ | H | phenyl | O | N=C(CH₃)₂ |
| H | OCH₃ | H | 2-CH₃-phenyl | O | N=C(CH₃)₂ |
| H | OCH₃ | H | 3-CH₃-phenyl | O | N=C(CH₃)₂ |
| H | OCH₃ | H | 4-CH₃-phenyl | O | N=C(CH₃)₂ |
| H | OCH₃ | H | 2,4-(CH₃,CH₃)-phenyl | O | N=C(CH₃)₂ |
| H | OCH₃ | H | 2,3,5-(CH₃,CH₃CH₃)-phenyl | O | N=C(CH₃)₂ |
| H | OCH₃ | H | 3-CF₃-phenyl | O | N=C(CH₃)₂ |
| H | OCH₃ | H | 3-F-phenyl | O | N=C(CH₃)₂ |
| H | OCH₃ | H | 2-Cl-phenyl | O | N=C(CH₃)₂ |
| H | OCH₃ | H | 4-Cl-phenyl | O | N=C(CH₃)₂ |
| H | OCH₃ | H | 2,4-(F,F)-phenyl | O | N=C(CH₃)₂ |
| H | OCH₃ | H | 2,3,5-(Cl,Cl,Cl)-phenyl | O | N=C(CH₃)₂ |
| H | OCH₃ | H | 2-CN-phenyl | O | N=C(CH₃)₂ |
| H | OCH₃ | H | 2-OCH₃-phenyl | O | N=C(CH₃)₂ |
| H | OCH₃ | H | 2,3-(OCH₃,OCH₃)-phenyl | O | N=C(CH₃)₂ |
| H | OCH₃ | H | 3,4,5-(OCH₃,OCH₃,OCH₃)-phenyl | O | N=C(CH₃)₂ |
| H | OCH₃ | H | 3-OCF₃-phenyl | O | N=C(CH₃)₂ |
| H | OCH₃ | H | 3-OCF₂OHF₂-phenyl | O | N=C(CH₃)₂ |
| H | OCH₃ | H | 4-OCF₂CHF₂-phenyl | O | N=C(CH₃)₂ |
| H | OCH₃ | H | 2-SCH₃-phenyl | O | N=C(CH₃)₂ |
| H | OCH₃ | H | 2,4-(SCH₃,SCH₃)-phenyl | O | N=C(CH₃)₂ |
| H | OCH₃ | H | 2-SCF₃-phenyl | O | N=C(CH₃)₂ |
| H | OCH₃ | H | 4-NO₂-phenyl | O | N=C(CH₃)₂ |
| H | OCH₃ | H | 2,4-(NO₂,NO₂)-phenyl | O | N=C(CH₃)₂ |
| H | OCH₃ | H | 3-COCH₃-phenyl | O | N=C(CH₃)₂ |
| H | OCH₃ | H | 3-COCF₃-phenyl | O | N=C(CH₃)₂ |
| H | OCH₃ | H | 1-naphthyl | O | N=C(CH₃)₂ |
| H | OCH₃ | H | 2-naphthyl | O | N=C(CH₃)₂ |
| H | OCH₃ | H | piperidino | O | N=C(CH₃)₂ |
| H | OCH₃ | H | 3-tetrahydrofuranyl | O | N=C(CH₃)₂ |
| H | OCH₃ | H | 4-tetrahydropyranyl | O | N=C(CH₃)₂ |
| H | OCH₃ | H | 2-thiazolyl | O | N=C(CH₃)₂ |
| H | OCH₃ | H | 5-CH₃-2-thiazolyl | O | N=C(CH₃)₂ |
| H | OCH₃ | H | 4-CH₃-5-COOH-2-thiazolyl | O | N=C(CH₃)₂ |
| Br | H | CH₃ | methyl | O | H |
| Br | H | CH₃ | ethyl | O | H |
| Br | H | CH₃ | n-propyl | O | H |
| Br | H | CH₃ | iso-propyl | O | H |
| Br | H | CH₃ | cyclopropyl | O | H |
| Br | H | CH₃ | n-butyl | O | H |
| Br | H | CH₃ | iso-butyl | O | H |
| Br | H | CH₃ | sec.-butyl | O | H |
| Br | H | CH₃ | tert.-butyl | O | H |
| Br | H | CH₃ | n-pentyl | O | H |
| Br | H | CH₃ | 2-pentyl | O | H |
| Br | H | CH₃ | 3-pentyl | O | H |
| Br | H | CH₃ | n-hexyl | O | H |
| Br | H | CH₃ | 2-hexyl | O | H |
| Br | H | CH₃ | 3-hexyl | O | H |
| Br | H | CH₃ | 2-methyl-2-pentyl | O | H |
| Br | H | CH₃ | cyclo-propylmethyl | O | H |
| Br | H | CH₃ | cyclo-butyl | O | H |
| Br | H | CH₃ | cyclo-pentyl | O | H |
| Br | H | CH₃ | cyclo-hexyl | O | H |
| Br | H | CH₃ | 1-methylcyclohexyl | O | H |
| Br | H | CH₃ | 3-trifluoromethylcyclohexyl | O | H |
| Br | H | CH₃ | allyl | O | H |
| Br | H | CH₃ | 1-buten-3-yl | O | H |
| Br | H | CH₃ | crotyl | O | H |
| Br | H | CH₃ | propargyl | O | H |
| Br | H | CH₃ | 1-butyn-3-yl | O | H |
| Br | H | CH₃ | 3-methyl-1-butyn-3-yl | O | H |

TABLE-continued

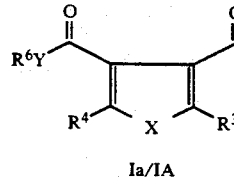

| $R^3$ | $R^4$ | $R^1$ | $R^2$ | Y | $R^6$ |
|---|---|---|---|---|---|
| Br | H | CH$_3$ | 2-pentyn-4-yl | O | H |
| Br | H | CH$_3$ | benzyl | O | H |
| Br | H | CH$_3$ | 2-phenylethyl | O | H |
| Br | H | CH$_3$ | 2-methylthioethyl | O | H |
| Br | H | CH$_3$ | 2-chloroethyl | O | H |
| Br | H | CH$_3$ | 2-methoxyethyl | O | H |
| Br | H | CH$_3$ | 2-(N,N-dimethylamino)ethyl | O | H |
| Br | H | CH$_3$ | phenyl | O | H |
| Br | H | CH$_3$ | 2-CH$_3$-phenyl | O | H |
| Br | H | CH$_3$ | 3-CH$_3$-phenyl | O | H |
| Br | H | CH$_3$ | 4-CH$_3$-phenyl | O | H |
| Br | H | CH$_3$ | 2,4-(CH$_3$,CH$_3$)-phenyl | O | H |
| Br | H | CH$_3$ | 2,3,5-(CH$_3$,CH$_3$CH$_3$)-phenyl | O | H |
| Br | H | CH$_3$ | 3-CF$_3$-phenyl | O | H |
| Br | H | CH$_3$ | 3-F-phenyl | O | H |
| Br | H | CH$_3$ | 2-Cl-phenyl | O | H |
| Br | H | CH$_3$ | 4-Cl-phenyl | O | H |
| Br | H | CH$_3$ | 2,4-(F,F)-phenyl | O | H |
| Br | H | CH$_3$ | 2,3,5-(Cl,Cl,Cl)-phenyl | O | H |
| Br | H | CH$_3$ | 2-CN-phenyl | O | H |
| Br | H | CH$_3$ | 2-OCH$_3$-phenyl | O | H |
| Br | H | CH$_3$ | 2,3-(OCH$_3$,OCH$_3$)-phenyl | O | H |
| Br | H | CH$_3$ | 3,4,5-(OCH$_3$,OCH$_3$,OCH$_3$)-phenyl | O | H |
| Br | H | CH$_3$ | 3-OCF$_3$-phenyl | O | H |
| Br | H | CH$_3$ | 3-OCF$_2$OHF$_2$-phenyl | O | H |
| Br | H | CH$_3$ | 4-OCF$_2$CHF$_2$-phenyl | O | H |
| Br | H | CH$_3$ | 2-SCH$_3$-phenyl | O | H |
| Br | H | CH$_3$ | 2,4-(SCH$_3$,SCH$_3$)-phenyl | O | H |
| Br | H | CH$_3$ | 2-SCF$_3$-phenyl | O | H |
| Br | H | CH$_3$ | 4-NO$_2$-phenyl | O | H |
| Br | H | CH$_3$ | 2,4-(NO$_2$,NO$_2$)-phenyl | O | H |
| Br | H | CH$_3$ | 3-COCH$_3$-phenyl | O | H |
| Br | H | CH$_3$ | 3-COCF$_3$-phenyl | O | H |
| Br | H | CH$_3$ | 1-naphthyl | O | H |
| Br | H | CH$_3$ | 2-naphthyl | O | H |
| Br | H | CH$_3$ | piperidino | O | H |
| Br | H | CH$_3$ | 3-tetrahydrofuranyl | O | H |
| Br | H | CH$_3$ | 4-tetrahydropyranyl | O | H |
| Br | H | CH$_3$ | 2-thiazolyl | O | H |
| Br | H | CH$_3$ | 5-CH$_3$-2-thiazolyl | O | H |
| Br | H | CH$_3$ | 4-CH$_3$-5-COOH-2-thiazolyl | O | H |
| CH$_3$ | CH$_3$ | allyl | methyl | O | H |
| CH$_3$ | CH$_3$ | allyl | ethyl | O | H |
| CH$_3$ | CH$_3$ | allyl | n-propyl | O | H |
| CH$_3$ | CH$_3$ | allyl | iso-propyl | O | H |
| CH$_3$ | CH$_3$ | allyl | cyclopropyl | O | H |
| CH$_3$ | CH$_3$ | allyl | n-butyl | O | H |
| CH$_3$ | CH$_3$ | allyl | iso-butyl | O | H |
| CH$_3$ | CH$_3$ | allyl | sec.-butyl | O | H |
| CH$_3$ | CH$_3$ | allyl | tert.-butyl | O | H |
| CH$_3$ | CH$_3$ | allyl | n-pentyl | O | H |
| CH$_3$ | CH$_3$ | allyl | 2-pentyl | O | H |
| CH$_3$ | CH$_3$ | allyl | 3-pentyl | O | H |
| CH$_3$ | CH$_3$ | allyl | n-hexyl | O | H |
| CH$_3$ | CH$_3$ | allyl | 2-hexyl | O | H |
| CH$_3$ | CH$_3$ | allyl | 3-hexyl | O | H |
| CH$_3$ | CH$_3$ | allyl | 2-methyl-2-pentyl | O | H |
| CH$_3$ | CH$_3$ | allyl | cyclo-propylmethyl | O | H |
| CH$_3$ | CH$_3$ | allyl | cyclo-butyl | O | H |
| CH$_3$ | CH$_3$ | allyl | cyclo-pentyl | O | H |
| CH$_3$ | CH$_3$ | allyl | cyclo-hexyl | O | H |
| CH$_3$ | CH$_3$ | allyl | 1-methylcyclohexyl | O | H |
| CH$_3$ | CH$_3$ | allyl | 3-trifluoromethylcyclohexyl | O | H |
| CH$_3$ | CH$_3$ | allyl | allyl | O | H |
| CH$_3$ | CH$_3$ | allyl | 1-buten-3-yl | O | H |
| CH$_3$ | CH$_3$ | allyl | crotyl | O | H |
| CH$_3$ | CH$_3$ | allyl | propargyl | O | H |
| CH$_3$ | CH$_3$ | allyl | 1-butyn-3-yl | O | H |
| CH$_3$ | CH$_3$ | allyl | 3-methyl-1-butyn-3-yl | O | H |
| CH$_3$ | CH$_3$ | allyl | 2-pentyn-4-yl | O | H |
| CH$_3$ | CH$_3$ | allyl | benzyl | O | H |

TABLE-continued

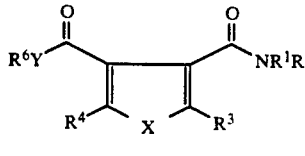 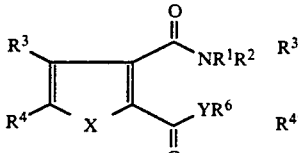 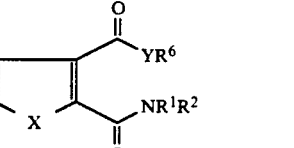

Ia/IA    Ib/IB    Ic/IC

| R³ | R⁴ | R¹ | R² | Y | R⁶ |
|---|---|---|---|---|---|
| CH₃ | CH₃ | allyl | 2-phenylethyl | O | H |
| CH₃ | CH₃ | allyl | 2-methylthioethyl | O | H |
| CH₃ | CH₃ | allyl | 2-chloroethyl | O | H |
| CH₃ | CH₃ | allyl | 2-methoxyethyl | O | H |
| CH₃ | CH₃ | allyl | 2-(N,N-dimethylamino)ethyl | O | H |
| CH₃ | CH₃ | allyl | phenyl | O | H |
| CH₃ | CH₃ | allyl | 2-CH₃-phenyl | O | H |
| CH₃ | CH₃ | allyl | 3-CH₃-phenyl | O | H |
| CH₃ | CH₃ | allyl | 4-CH₃-phenyl | O | H |
| CH₃ | CH₃ | allyl | 2,4-(CH₃,CH₃)-phenyl | O | H |
| CH₃ | CH₃ | allyl | 2,3,5-(CH₃,CH₃CH₃)-phenyl | O | H |
| CH₃ | CH₃ | allyl | 3-CF₃-phenyl | O | H |
| CH₃ | CH₃ | allyl | 3-F-phenyl | O | H |
| CH₃ | CH₃ | allyl | 2-Cl-phenyl | O | H |
| CH₃ | CH₃ | allyl | 4-Cl-phenyl | O | H |
| CH₃ | CH₃ | allyl | 2,4-(F,F)-phenyl | O | H |
| CH₃ | CH₃ | allyl | 2,3,5-(Cl,Cl,Cl)-phenyl | O | H |
| CH₃ | CH₃ | allyl | 2-CN-phenyl | O | H |
| CH₃ | CH₃ | allyl | 2-OCH₃-phenyl | O | H |
| CH₃ | CH₃ | allyl | 2,3-(OCH₃,OCH₃)-phenyl | O | H |
| CH₃ | CH₃ | allyl | 3,4,5-(OCH₃,OCH₃,OCH₃)-phenyl | O | H |
| CH₃ | CH₃ | allyl | 3-OCF₃-phenyl | O | H |
| CH₃ | CH₃ | allyl | 3-OCF₂OHF₂-phenyl | O | H |
| CH₃ | CH₃ | allyl | 4-OCF₂CHF₂-phenyl | O | H |
| CH₃ | CH₃ | allyl | 2-SCH₃-phenyl | O | H |
| CH₃ | CH₃ | allyl | 2,4-(SCH₃,SCH₃)-phenyl | O | H |
| CH₃ | CH₃ | allyl | 2-SCF₃-phenyl | O | H |
| CH₃ | CH₃ | allyl | 4-NO₂-phenyl | O | H |
| CH₃ | CH₃ | allyl | 2,4-(NO₂,NO₂)-phenyl | O | H |
| CH₃ | CH₃ | allyl | 3-COCH₃-phenyl | O | H |
| CH₃ | CH₃ | allyl | 3-COCF₃-phenyl | O | H |
| CH₃ | CH₃ | allyl | 1-naphthyl | O | H |
| CH₃ | CH₃ | allyl | 2-naphthyl | O | H |
| CH₃ | CH₃ | allyl | piperidino | O | H |
| CH₃ | CH₃ | allyl | 3-tetrahydrofuranyl | O | H |
| CH₃ | CH₃ | allyl | 4-tetrahydropyranyl | O | H |
| CH₃ | CH₃ | allyl | 2-thiazolyl | O | H |
| CH₃ | CH₃ | allyl | 5-CH₃-2-thiazolyl | O | H |
| CH₃ | CH₃ | allyl | 4-CH₃-5-COOH-2-thiazolyl | O | H |
| H | Cl | H | methyl | S | CH₃ |
| H | Cl | H | ethyl | S | CH₃ |
| H | Cl | H | n-propyl | S | CH₃ |
| H | Cl | H | iso-propyl | S | CH₃ |
| H | Cl | H | cyclopropyl | S | CH₃ |
| H | Cl | H | n-butyl | S | CH₃ |
| H | Cl | H | iso-butyl | S | CH₃ |
| H | Cl | H | sec.-butyl | S | CH₃ |
| H | Cl | H | tert.-butyl | S | CH₃ |
| H | Cl | H | n-pentyl | S | CH₃ |
| H | Cl | H | 2-pentyl | S | CH₃ |
| H | Cl | H | 3-pentyl | S | CH₃ |
| H | Cl | H | n-hexyl | S | CH₃ |
| H | Cl | H | 2-hexyl | S | CH₃ |
| H | Cl | H | 3-hexyl | S | CH₃ |
| H | Cl | H | 2-methyl-2-pentyl | S | CH₃ |
| H | Cl | H | cyclo-propylmethyl | S | CH₃ |
| H | Cl | H | cyclo-butyl | S | CH₃ |
| H | Cl | H | cyclo-pentyl | S | CH₃ |
| H | Cl | H | cyclo-hexyl | S | CH₃ |
| H | Cl | H | 1-methylcyclohexyl | S | CH₃ |
| H | Cl | H | 3-trifluoromethylcyclohexyl | S | CH₃ |
| H | Cl | H | allyl | S | CH₃ |
| H | Cl | H | 1-buten-3-yl | S | CH₃ |
| H | Cl | H | crotyl | S | CH₃ |
| H | Cl | H | propargyl | S | CH₃ |
| H | Cl | H | 1-butyn-3-yl | S | CH₃ |
| H | Cl | H | 3-methyl-1-butyn-3-yl | S | CH₃ |
| H | Cl | H | 2-pentyn-4-yl | S | CH₃ |
| H | Cl | H | benzyl | S | CH₃ |
| H | Cl | H | 2-phenylethyl | S | CH₃ |
| H | Cl | H | 2-methylthioethyl | S | CH₃ |

TABLE-continued

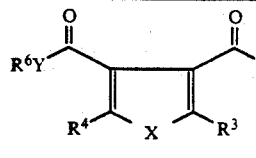

| $R^3$ | $R^4$ | $R^1$ | $R^2$ | X | $YR^6$ |
|---|---|---|---|---|---|
| H | Cl | H | 2-chloroethyl | S | $CH_3$ |
| H | Cl | H | 2-methoxyethyl | S | $CH_3$ |
| H | Cl | H | 2-(N,N-dimethylamino)ethyl | S | $CH_3$ |
| H | Cl | H | phenyl | S | $CH_3$ |
| H | Cl | H | 2-$CH_3$-phenyl | S | $CH_3$ |
| H | Cl | H | 3-$CH_3$-phenyl | S | $CH_3$ |
| H | Cl | H | 4-$CH_3$-phenyl | S | $CH_3$ |
| H | Cl | H | 2,4-($CH_3$,$CH_3$)-phenyl | S | $CH_3$ |
| H | Cl | H | 2,3,5-($CH_3$,$CH_3$$CH_3$)-phenyl | S | $CH_3$ |
| H | Cl | H | 3-$CF_3$-phenyl | S | $CH_3$ |
| H | Cl | H | 3-F-phenyl | S | $CH_3$ |
| H | Cl | H | 2-Cl-phenyl | S | $CH_3$ |
| H | Cl | H | 4-Cl-phenyl | S | $CH_3$ |
| H | Cl | H | 2,4-(F,F)-phenyl | S | $CH_3$ |
| H | Cl | H | 2,3,5-(Cl,Cl,Cl)-phenyl | S | $CH_3$ |
| H | Cl | H | 2-CN-phenyl | S | $CH_3$ |
| H | Cl | H | 2-$OCH_3$-phenyl | S | $CH_3$ |
| H | Cl | H | 2,3-($OCH_3$,$OCH_3$)-phenyl | S | $CH_3$ |
| H | Cl | H | 3,4,5-($OCH_3$,$OCH_3$,$OCH_3$)-phenyl | S | $CH_3$ |
| H | Cl | H | 3-$OCF_3$-phenyl | S | $CH_3$ |
| H | Cl | H | 3-$OCF_2OHF_2$-phenyl | S | $CH_3$ |
| H | Cl | H | 4-$OCF_2CHF_2$-phenyl | S | $CH_3$ |
| H | Cl | H | 2-$SCH_3$-phenyl | S | $CH_3$ |
| H | Cl | H | 2,4-($SCH_3$,$SCH_3$)-phenyl | S | $CH_3$ |
| H | Cl | H | 2-$SCF_3$-phenyl | S | $CH_3$ |
| H | Cl | H | 4-$NO_2$-phenyl | S | $CH_3$ |
| H | Cl | H | 2,4-($NO_2$,$NO_2$)-phenyl | S | $CH_3$ |
| H | Cl | H | 3-$COCH_3$-phenyl | S | $CH_3$ |
| H | Cl | H | 3-$COCF_3$-phenyl | S | $CH_3$ |
| H | Cl | H | 1-naphthyl | S | $CH_3$ |
| H | Cl | H | 2-naphthyl | S | $CH_3$ |
| H | Cl | H | piperidino | S | $CH_3$ |
| H | Cl | H | 3-tetrahydrofuranyl | S | $CH_3$ |
| H | Cl | H | 4-tetrahydropyranyl | S | $CH_3$ |
| H | Cl | H | 2-thiazolyl | S | $CH_3$ |
| H | Cl | H | 5-$CH_3$-2-thiazolyl | S | $CH_3$ |
| H | Cl | H | 4-$CH_3$-5-COOH-2-thiazolyl | S | $CH_3$ |
| H | $C_2H_5$ | H | methyl | O | $CH_2C\equiv CH$ |
| H | $C_2H_5$ | H | ethyl | O | $CH_2C\equiv CH$ |
| H | $C_2H_5$ | H | n-propyl | O | $CH_2C\equiv CH$ |
| H | $C_2H_5$ | H | iso-propyl | O | $CH_2C\equiv CH$ |
| H | $C_2H_5$ | H | cyclopropyl | O | $CH_2C\equiv CH$ |
| H | $C_2H_5$ | H | n-butyl | O | $CH_2C\equiv CH$ |
| H | $C_2H_5$ | H | iso-butyl | O | $CH_2C\equiv CH$ |
| H | $C_2H_5$ | H | sec.-butyl | O | $CH_2C\equiv CH$ |
| H | $C_2H_5$ | H | tert.-butyl | O | $CH_2C\equiv CH$ |
| H | $C_2H_5$ | H | n-pentyl | O | $CH_2C\equiv CH$ |
| H | $C_2H_5$ | H | 2-pentyl | O | $CH_2C\equiv CH$ |
| H | $C_2H_5$ | H | 3-pentyl | O | $CH_2C\equiv CH$ |
| H | $C_2H_5$ | H | n-hexyl | O | $CH_2C\equiv CH$ |
| H | $C_2H_5$ | H | 2-hexyl | O | $CH_2C\equiv CH$ |
| H | $C_2H_5$ | H | 3-hexyl | O | $CH_2C\equiv CH$ |
| H | $C_2H_5$ | H | 2-methyl-2-pentyl | O | $CH_2C\equiv CH$ |
| H | $C_2H_5$ | H | cyclo-propylmethyl | O | $CH_2C\equiv CH$ |
| H | $C_2H_5$ | H | cyclo-butyl | O | $CH_2C\equiv CH$ |
| H | $C_2H_5$ | H | cyclo-pentyl | O | $CH_2C\equiv CH$ |
| H | $C_2H_5$ | H | cyclo-hexyl | O | $CH_2C\equiv CH$ |
| H | $C_2H_5$ | H | 1-methylcyclohexyl | O | $CH_2C\equiv CH$ |
| H | $C_2H_5$ | H | 3-trifluoromethylcyclohexyl | O | $CH_2C\equiv CH$ |
| H | $C_2H_5$ | H | allyl | O | $CH_2C\equiv CH$ |
| H | $C_2H_5$ | H | 1-buten-3-yl | O | $CH_2C\equiv CH$ |
| H | $C_2H_5$ | H | crotyl | O | $CH_2C\equiv CH$ |
| H | $C_2H_5$ | H | propargyl | O | $CH_2C\equiv CH$ |
| H | $C_2H_5$ | H | 1-butyn-3-yl | O | $CH_2C\equiv CH$ |
| H | $C_2H_5$ | H | 3-methyl-1-butyn-3-yl | O | $CH_2C\equiv CH$ |
| H | $C_2H_5$ | H | 2-pentyn-4-yl | O | $CH_2C\equiv CH$ |
| H | $C_2H_5$ | H | benzyl | O | $CH_2C\equiv CH$ |
| H | $C_2H_5$ | H | 2-phenylethyl | O | $CH_2C\equiv CH$ |
| H | $C_2H_5$ | H | 2-methylthioethyl | O | $CH_2C\equiv CH$ |
| H | $C_2H_5$ | H | 2-chloroethyl | O | $CH_2C\equiv CH$ |
| H | $C_2H_5$ | H | 2-methoxyethyl | O | $CH_2C\equiv CH$ |

TABLE-continued

Ia/IA: $R^6Y-C(=O)-C(R^4)=C(X)-C(R^3)=C-C(=O)-NR^1R^2$ (ring structure)

Ib/IB: $R^3-C(=O)-... -YR^6$ with NR$^1$R$^2$

Ic/IC: $R^3-...-YR^6$ with NR$^1$R$^2$

X = O or S

| R³ | R⁴ | R¹ | R² | Y | R⁶ |
|---|---|---|---|---|---|
| H | C₂H₅ | H | 2-(N,N-dimethylamino)ethyl | O | CH₂C≡CH |
| H | C₂H₅ | H | phenyl | O | CH₂C≡CH |
| H | C₂H₅ | H | 2-CH₃-phenyl | O | CH₂C≡CH |
| H | C₂H₅ | H | 3-CH₃-phenyl | O | CH₂C≡CH |
| H | C₂H₅ | H | 4-CH₃-phenyl | O | CH₂C≡CH |
| H | C₂H₅ | H | 2,4-(CH₃,CH₃)-phenyl | O | CH₂C≡CH |
| H | C₂H₅ | H | 2,3,5-(CH₃,CH₃CH₃)-phenyl | O | CH₂C≡CH |
| H | C₂H₅ | H | 3-CF₃-phenyl | O | CH₂C≡CH |
| H | C₂H₅ | H | 3-F-phenyl | O | CH₂C≡CH |
| H | C₂H₅ | H | 2-Cl-phenyl | O | CH₂C≡CH |
| H | C₂H₅ | H | 4-Cl-phenyl | O | CH₂C≡CH |
| H | C₂H₅ | H | 2,4-(F,F)-phenyl | O | CH₂C≡CH |
| H | C₂H₅ | H | 2,3,5-(Cl,Cl,Cl)-phenyl | O | CH₂C≡CH |
| H | C₂H₅ | H | 2-CN-phenyl | O | CH₂C≡CH |
| H | C₂H₅ | H | 2-OCH₃-phenyl | O | CH₂C≡CH |
| H | C₂H₅ | H | 2,3-(OCH₃,OCH₃)-phenyl | O | CH₂C≡CH |
| H | C₂H₅ | H | 3,4,5-(OCH₃,OCH₃,OCH₃)-phenyl | O | CH₂C≡CH |
| H | C₂H₅ | H | 3-OCF₃-phenyl | O | CH₂C≡CH |
| H | C₂H₅ | H | 3-OCF₂OHF₂-phenyl | O | CH₂C≡CH |
| H | C₂H₅ | H | 4-OCF₂CHF₂-phenyl | O | CH₂C≡CH |
| H | C₂H₅ | H | 2-SCH₃-phenyl | O | CH₂C≡CH |
| H | C₂H₅ | H | 2,4-(SCH₃,SCH₃)-phenyl | O | CH₂C≡CH |
| H | C₂H₅ | H | 2-SCF₃-phenyl | O | CH₂C≡CH |
| H | C₂H₅ | H | 4-NO₂-phenyl | O | CH₂C≡CH |
| H | C₂H₅ | H | 2,4-(NO₂,NO₂)-phenyl | O | CH₂C≡CH |
| H | C₂H₅ | H | 3-COCH₃-phenyl | O | CH₂C≡CH |
| H | C₂H₅ | H | 3-COCF₃-phenyl | O | CH₂C≡CH |
| H | C₂H₅ | H | 1-naphthyl | O | CH₂C≡CH |
| H | C₂H₅ | H | 2-naphthyl | O | CH₂C≡CH |
| H | C₂H₅ | H | piperidino | O | CH₂C≡CH |
| H | C₂H₅ | H | 3-tetrahydrofuranyl | O | CH₂C≡CH |
| H | C₂H₅ | H | 4-tetrahydropyranyl | O | CH₂C≡CH |
| H | C₂H₅ | H | 2-thiazolyl | O | CH₂C≡CH |
| H | C₂H₅ | H | 5-CH₃-2-thiazolyl | O | CH₂C≡CH |
| H | C₂H₅ | H | 4-CH₃-5-COOH-2-thiazolyl | O | CH₂C≡CH |

X = O or S

Suitable salts of compounds of the formula IA, IB and IC are agriculturally useful salts, for example alkali metal salts, such as the potassium or sodium salt, alkaline earth metal salts, such as the calcium, magnesium or barium salt, manganese, copper, zinc or iron salts, and ammonium, phosphonium, sulfonium or sulfoxonium salts, e.g., ammonium salts, tetraalkylammonium salts, benzyltrialkylammonium salts, trialkylsulfonium salts and trialkylsulfoxonium salts.

The herbicidal compounds IA, IB and IC according to the invention, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.01 to 95, and preferably 0.1 to 90, % by weight of active ingredient. The active ingredients are used in a purity of 90 to 100, and preferably 95 to 100, % (according to the NMR spectrum).

The compounds IA, IB and IC may be formulated for instance as follows:

I. 90 parts by weight of compound no. 1.025 is mixed with 10 parts by weight of N-methyl-alpha-pyrrolidone. A mixture is obtained which is suitable for application in the form of very fine drops.

II. 20 parts by weight of compound no. 3.031 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzensulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1.001 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 1.025 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 3.031 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 2.005 is intimately mixed with 97 parts by weight of particulate kaolin. A dust is obtained containing 3% by weight of the active ingredient.

VII. 30 parts by weight of compound no. 3.001 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 3.031 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

IX. 90 parts by weight of compound no. 1.022 is mixed with 10 parts by weight of N-methyl-alpha-pyrrolidone. A mixture is obtained which is suitable for application in the form of very fine drops.

X. 20 parts by weight of compound no. 2.006 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

XI. 20 parts by weight of compound no. 3.036 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

XII. 20 parts by weight of compound no. 1.010 is dissolved in a mixture consisting of 25 part by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

XIII. 20 parts by weight of compound no. 3.015 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

XIV. 3 parts by weight of compound no. 1.025 is intimately mixed with 97 parts by weight of particulate kaolin. A dust is obtained containing 3% by weight of the active ingredient.

XV. 30 parts by weight of compound no. 3.031 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

XVI. 20 parts by weight of compound no. 2.001 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

When the active ingredients are used as herbicides, the application rates depend on the objective to be achieved, the time of the year, the plants to be combated and their growth stage, and are from 0.001 to 5, preferably 0.01 to 3, kg of active ingredient per hectare.

The application rates depend on the objective to be achieved, the time of the year, the plants to be combated and their growth stage, and are from 0.001 to 4, preferably 0.01 to 2, kg of active ingredient per hectare.

In view of the numerous application methods possible, the compounds according to the invention, or agents containing them, may be used in a large number of crops for removing unwanted plant growth.

To increase the spectrum of action and to achieve synergistic effects, the active ingredients IA, IB and IC according to the invention may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, (hetero)-aryloxyphenoxypropionic acids and salts, esters, amides thereof, etc.

It may also be useful to apply the active ingredients IA, IB and IC, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

SYNTHESIS EXAMPLES

The directions given in the synthesis examples below were employed, after appropriate modification of the starting materials, to obtain further compounds IA, IB and IC. The compounds thus obtained are listed in the tables below with their physical data.

MANUFACTURING EXAMPLES

EXAMPLE 1

THIOPHENE-3,4-DICARBOXYLIC ANHYDRIDE

Thiophene-3,4-dicarboxylic acid (12 g, 0.07 mol) is dissolved in acetic anhydride (60 ml) and boiled for 2.5 hours. The mixture is then concentrated to dryness. There is obtained 10.55 g (98%) of thiophene-3,4-dicarboxylic anhydride (m.p. 147°–149° C.).

EXAMPLE 2

4-(4-Chlorophenyl)-aminocarbonylthiophene-3-carboxylic acid

4-Chloroaniline (1.65 g, 0.013 mol) is added to a mixture of thiophene-3,4-dicarboxylic anhydride (2 g, 0.013 mol) in 60 ml of toluene. The mixture is stirred for 3 hours at room temperature and the precipitated carboxylic acid is filtered off and washed with a little toluene. After drying there is obtained 3.7 g (100%) of the desired product, m.p. 204°–208° C. (active ingredient no. 1.035).

EXAMPLE 3

4-(4-Chlorophenyl)-aminocarbonylthiophene-3-carboxylic acid hydroxysuccinimide ester.

N-Hydroxysuccinimide (0.7 g, 0.006 mol) and N,N-dicyclohexylcarbodiimide (1.25 g, 0.006 mol) are added to a solution of 4-(4-chlorophenyl)-aminocarbonylthiophene-3-carboxylic acid (1.7 g, 0.006 mol) in 60 ml of THF, and the mixture is stirred for several hours at room temperature. The solution is then cooled to 0° C. and kept at this temperature for several hours, and the precipitated urea is filtered off and concentrated to dryness. Yield: 1.8 g, 66%; m.p. 65°–67° C. (active ingredient no. 1.026).

Example 4

4-Chlorothiophene-3-carboxanilide

At room temperature, a solution of 4-chlorothiophene-3-carboxylic chloride (13.5 g, 0.075 mol) in 30 ml of dioxane is dripped into a solution of aniline (7.7 g, 0.083 mol) in pyridine (160 ml). The mixture is stirred for 12 hours at room temperature and concentrated to dryness, and the residue is taken up in dichloromethane. The organic phase is extracted with aqueous citric acid solution, sodium bicarbonate solution and water, dried and concentrated to dryness. Yield: 16.7 g, 94%; m.p. 119°–121° C.

Example 5

4-Chloro-3-phenylaminocarbonylthiophene-2-carboxylic acid

4-Chlorothiophene-3-carboxanilide (14.6 g, 0.061 mol) is dissolved in 450 ml of THF and the solution is cooled to −70° C.; n-butyllithium (0.13 mol, 1.6N solution in n-hexane) is then added. After 30 minutes, carbon dioxide is gassed in until the solution was saturated, and the solution is allowed to heat up slowly to room temperature. It is then concentrated to dryness, the solid residue is taken up in a mixture of water, sodium hydroxide solution and ethyl acetate, the phases are separated and the aqueous phase is acidified with hydrochloric acid, thus precipitating the carboxylic acid. Yield: 13.5 g, 78%; m.p. 208°-210° C. (active ingredient no. 2.008).

TABLE 1

Ia/IA

Structure: R5, R4, X, R3 substituents on ring with C(O)NR1R2 group

| No. | R¹ | R² | R³ | R⁴ | X | (R⁵) | mp. [°C.] |
|---|---|---|---|---|---|---|---|
| 1.001 | H | 3-OCH₃—C₆H₄ | H | H | S | CO₂—N(succinimide) | 147-149 |
| 1.002 | H | 3-CH₃—C₆H₄ | H | H | S | CO₂—N(succinimide) | 184-186 |
| 1.003 | H | 2-Cl—C₆H₄ | H | H | S | CO₂—N(succinimide) | 128-129 |
| 1.004 | H | cyclopropyl | H | H | S | CO₂—N(succinimide) | 75-77 |
| 1.005 | H | C₆H₅ | H | H | S | CO₂—N(succinimide) | 158-160 |
| 1.006 | H | CH(CH₃)₂ | H | H | S | CO₂—N(succinimide) | 179-181 |
| 1.007 | H | (3,5-dichloro-4-methyl-thiophen-2-yl) | H | H | S | CO₂H | 200-202 |
| 1.008 | H | CH(CH₃)₂ | H | H | O | CO₂CH₂CH₃ | 32-34 |
| 1.009 | H | CH(CH₂)₂ | H | H | O | CO₂H | 171-174 |
| 1.010 | H | C(CH₃)₃ | H | H | O | CO₂CH₂CH₃ | 48-50 |
| 1.011 | H | C(CH₃)₃ | H | H | O | CO₂H | 190-194 |
| 1.012 | H | C₆H₅ | H | H | O | CO₂CH₂CH₃ | 154-156 |
| 1.013 | H | C₆H₅ | H | H | O | CO₂H | 265-270 |
| 1.014 | H | 3-CF₃—C₆H₄ | H | H | O | CO₂CH₂CH₃ | 85-87 |
| 1.015 | H | 3-CF₃—C₆H₄ | H | H | O | CO₂H | 245-249 |
| 1.016 | H | 4-Cl—C₆H₄ | H | H | O | CO₂CH₂CH₃ | 111-114 |
| 1.017 | H | 4-Cl—C₆H₄ | H | H | O | CO₂H | 251-255 |

TABLE 1-continued

Ia/IA

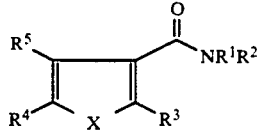

| No. | R¹ | R² | R³ | R⁴ | X | | mp. [°C.] |
|---|---|---|---|---|---|---|---|
| 1.018 | H | 3-F—$C_6H_4$ | H | H | S | $CO_2H$ | 200–204 |
| 1.019 | H | 3-$CF_3$—$C_6H_4$ | H | H | S | $CO_2H$ | 215–217 |
| 1.020 | H | $CH_2$—$C_6H_4$ | H | H | S | $CO_2H$ | 215–218 |
| 1.021 | H | 4-F—$C_6H_4$ | H | H | S | $CO_2H$ | 218–220 |
| 1.022 | H | cyclopropyl | H | H | S | $CO_2H$ | 170–173 |
| 1.023 | H | —$CH_2$-cyclopropyl | H | H | S | $CO_2H$ | 165–168 |
| 1.024 | H | 4-F—$C_6H_4$ | H | H | S | 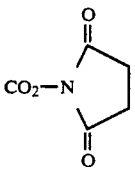 | 135–137 |
| 1.025 | H | 3-F—$C_6H_4$ | H | H | S | 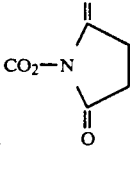 | 140–142 |
| 1.026 | H | 4-Cl—$C_6H_4$ | H | H | S | 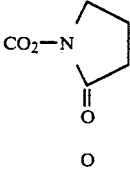 | 65–67 |
| 1.027 | H | 3-Cl—$C_6H_4$ | H | H | S | 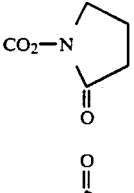 | 146–149 |
| 1.028 | H | 3,4-Cl,Cl—$C_6H_3$ | H | H | S | 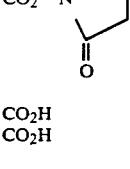 | 205–207 |
| 1.029 | H | $CH(CH_3)_2$ | H | H | S | $CO_2H$ | 161–169 |
| 1.030 | H | $C(CH_3)_3$ | H | H | S | $CO_2H$ | 127–139 |
| 1.031 | H | 3-$CF_3$—$C_6H_4$ | H | H | S | 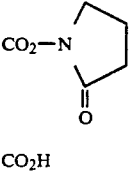 | 143–147 |
| 1.032 | H | $C_6H_5$ | H | H | S | $CO_2H$ | 205–208 |
| 1.033 | H | 3-Cl—$C_6H_4$ | H | H | S | $CO_2H$ | 235–237 |
| 1.034 | H | 2-Cl—$C_6H_4$ | H | H | S | $CO_2H$ | 186–187 |
| 1.035 | H | 4-Cl—$C_6H_4$ | H | H | S | $CO_2H$ | 204–208 |
| 1.036 | H | 3,4-Cl,Cl—$C_6H_3$ | H | H | S | $CO_2H$ | >230 |
| 1.037 | H | 3-$OCH_3$—$C_6H_4$ | H | H | S | $CO_2H$ | 170–173 |
| 1.038 | H | 4-$OCH_3$—$C_6H_4$ | H | H | S | $CO_2H$ | 250–253 |
| 1.039 | H | 3-$CH_3$—$C_6H_4$ | H | H | S | $CO_2H$ | 220–223 |

TABLE 1-continued

Ia/IA

| No. | R¹ | R² | R³ | R⁴ | X | R⁵ | mp. [°C.] |
|---|---|---|---|---|---|---|---|
| 1.040 | H | 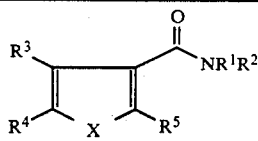 | H | H | S | CO₂H | |
| 1.041 | H | (4-fluoro-2-chloro-5-methoxyphenyl) | H | H | S | CO₂H | 183–185 |
| 1.042 | H | (2-chloro-6-(1,3-dioxolan-2-yl)phenyl) | H | H | S | CO₂H | 206–208 |

TABLE 2

Ib/IB

| No. | R¹ | R² | R³ | R⁴ | X | R⁵ | mp. [°C.] |
|---|---|---|---|---|---|---|---|
| 2.001 | H | CH(CH₃)₂ | H | H | S | CO₂H | 160–162 |
| 2.002 | H | 3-CF₃—C₆H₄ | H | H | S | CO₂H | 158–160 |
| 2.003 | H | C₆H₅ | H | H | S | CO₂H | 190–192 |
| 2.004 | H | C(CH₃)₃ | H | H | S | CO₂H | 163–165 |
| 2.005 | H | CH(CH₃)₂ | H | H | S | 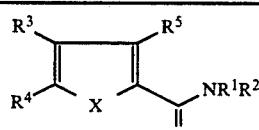 | 197–199 |

TABLE 2-continued

Ib/IB

| No. | R¹ | R² | R³ | R⁴ | X | R⁵ | mp. [°C.] |
|---|---|---|---|---|---|---|---|
| 2.006 | H | C(CH₃)₃ | Cl | H | S | CO₂H | 176–179 |
| 2.007 | H | 3-CF₃—C₆H₄ | Cl | H | S | CO₂H | 186–188 |
| 2.008 | H | C₆H₅ | Cl | H | S | CO₂H | 208–210 |
| 2.009 | H | CH(CH₃)₂ | Cl | H | S | CO₂H | 219–221 |
| 2.010 | H | CH(CH₃)₂ | CN | H | S | CO₂H | 195–197 |
| 2.011 | H | C(CH₃)₃ | H | Cl | S | CO₂H | 216–218 |
| 2.012 | H | 3-CF₃—C₆H₄ | Cl | Cl | S | CO₂H | 242–244 |

TABLE 3

Ic/IC

| No. | R¹ | R² | R³ | R⁴ | X | R⁵ | mp. [°C.] |
|---|---|---|---|---|---|---|---|
| 3.001 | H | C(CH₃)₃ | H | H | S | CO₂H | 179–182 |
| 3.002 | H | 3-CF₃—C₆H₄ | H | H | S | CO₂H | 151–153 |
| 3.003 | H | 4-Cl—C₆H₄ | H | H | S | CO₂H | 218–220 |
| 3.004 | H | C₆H₅ | H | H | S | CO₂H | 258–260 |
| 3.005 | CH₃ | CH₃ | H | H | S | CO₂H | 155–160 |
| 3.006 | H | C(CH₃)₂CH₂CH₃ | H | H | S | CO₂H | 77–84 |
| 3.007 | H | C(CH₃)₂CH=CH₂ | H | H | S | CO₂H | 98–100 |
| 3.008 | H | C(CH₃)₂C≡CH | H | H | S | CO₂H | oil |
| 3.009 | H | C(CH₃)₂CN | H | H | S | CO₂H | 200–205 |
| 3.010 | H | C(CH₃)₂CH₂SCH₃ | H | H | S | CO₂H | 108–112 |

TABLE 3-continued

Structure: R³ and R⁵ on a five-membered ring with X, R⁴ on the ring, with -C(=O)NR¹R² substituent. Ic/IC

| No. | R¹ | R² | R³ | R⁴ | X | R⁵ | mp. [°C.] |
|---|---|---|---|---|---|---|---|
| 3.011 | H | 4-F, 2-Cl, 5-(OCH₂C≡CH)-C₆H₂ | H | H | S | CO₂H | 242–247 |
| 3.012 | H | 4-F, 2-Cl, 5-(OCH₂CO₂CH₃)-C₆H₂ | H | H | S | CO₂H | 222–226 |
| 3.013 | H | C(CH₃)₃ | H | Cl | S | CO₂H | 233–235 |
| 3.014 | H | cyclopropyl | H | Cl | S | CO₂H | 204–206 |
| 3.015 | H | CH(CH₃)₂ | H | Cl | S | CO₂H | 175–177 |
| 3.016 | H | C₆H₅ | H | Cl | S | CO₂H | 220–222 |
| 3.017 | H | 3-CF₃—C₆H₄ | H | Cl | S | CO₂H | 158–160 |
| 3.018 | H | CH(CH₃)₂ | H | Cl | S | CO₂-N(succinimidyl) | 207–209 |
| 3.019 | H | C(CH₃)₃ | H | Cl | S | CO₂-N(succinimidyl) | 181–183 |
| 3.020 | H | C(CH₃)₃ | H | Cl | S | CO₂—N=C(CH₃)₂ | 188–190 |
| 3.021 | H | OC(CH₃)₃ | H | Cl | S | CO₂H | 206–208 |
| 3.022 | H | C(CH₃)₃ | H | CH₃ | S | CO₂H | 162–166 |
| 3.023 | H | CH(CH₃)₂ | H | CH₃ | S | CO₂H | 88–90 |
| 3.024 | H | C(CH₃)₃ | H | CH₃ | S | CO₂—N=C(CH₃)₂ | 148–152 |
| 3.025 | H | CH(CH₃)₂ | H | CH₃ | S | CO₂—N=C(CH₃)₂ | 78–80 |
| 3.026 | H | cyclopropyl | H | CH₃ | S | CO₂H | 147–149 |
| 3.027 | H | 4-Cl—C₆H₄ | H | CH₃ | S | CO₂H | 230–235 |
| 3.028 | H | C(CH₃)₃ | H | H | O | CO₂H | 123–126 |
| 3.029 | H | CH(CH₃)₂ | H | H | O | CO₂H | 62–70 |
| 3.030 | H | 3-CF₃—C₆H₄ | H | H | O | CO₂H | 170–173 |
| 3.031 | H | C(CH₃)₃ | H | CH₃ | O | CO₂H | 124–127 |
| 3.032 | H | C(CH₃)₃ | H | CH₃ | O | CO₂N=C(CH₃)₂ | 132–136 |
| 3.033 | H | CH(CH₃)₂ | H | CH₃ | O | CO₂H | 138–141 |
| 3.034 | H | CH(CH₃)₂ | H | CH₃ | O | CO₂N=C(CH₃)₂ | 102–106 |
| 3.035 | H | cyclopropyl | H | CH₃ | O | CO₂H | 154–160 |
| 3.036 | H | 4-Cl—C₆H₄ | H | CH₃ | O | CO₂H | 230–232 |
| 3.037 | H | 4-Cl—C₆H₄ | H | CH₃ | O | CO₂N=C(CH₃)₂ | 160–168 |
| 3.038 | H | CH(CH₃)₂ | H | H | S | CO₂H | 141–143 |
| 3.039 | H | CH(CH₃)₂ | H | Cl | S | CO₂CH₂C≡CH | 93–95 |
| 3.040 | H | C₆H₁₁ | H | Cl | S | CO₂H | 251–253 |
| 3.041 | H | cyclopropyl | H | Cl | S | CO₂N=C(CH₃)₂ | 124–126 |
| 3.042 | H | C(CH₃)₃ | H | OCH₃ | S | CO₂H | 176–178 |
| 3.043 | H | cyclopropyl | H | OCH₃ | S | CO₂H | 168–170 |

TABLE 3-continued

Structure:
$$\underset{R^4}{\overset{R^3}{\diagdown}}\underset{X}{\diagup}\overset{R^5}{\underset{\underset{O}{\|}}{\diagdown}}C-NR^1R^2$$

Ic/IC

| No. | R¹ | R² | R³ | R⁴ | X | R⁵ | mp. [°C.] |
|---|---|---|---|---|---|---|---|
| 3.044 | H | cyclopropyl | H | Cl | S | (succinimido-CO₂—N group) | 215–217 |
| 3.045 | H | 2,3,5-trimethylphenyl (CH₃, H₃C, CH₃) | H | Cl | S | CO₂H | 246–248 |
| 3.046 | H | 2,6-diethylphenyl (C₂H₅, H₅C₂) | H | Cl | S | CO₂H | 170–172 |
| 3.047 | H | 2,3-dimethylphenyl (CH₃, H₃C) | H | CH₃ | S | CO₂H | 237–239 |
| 3.048 | H | C₆H₅ | C₆H₅ | C₆H₅ | O | CO₂CH₃ | |
| 3.049 | H | 2-Cl-5-[C(CH₃)=CH—]-phenyl with CO₂CH₃ | H | H | S | CO₂H | 178–184 |
| 3.050 | H | 3-CF₃—C₆H₄ | H | 4-CH₃—C₆H₄ | S | CO₂H | 262–268 |
| 3.051 | H | C(CH₃)₃ | H | 4-CH₃—C₆H₄ | S | CO₂H | 144–146 |

Use examples

The herbicidal action of carboxamides of the formula IA, IB and IC is demonstrated in greenhouse experiments:

The vessels employed were plastic flowerpots having a volume of 300 cm³ and filled with a sandy loam containing about 3.0% humus. The seeds of the test plants were sown separately, according to species.

For the preemergence treatment, the active ingredients, suspended or emulsified in water, were applied to the surface of the soil immediately after the seeds had been sown. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated with the compounds, suspended or emulsified in water. The application rates for post-emergence treatment were 0.5 and 1.0 kg/ha.

The pots were set up in the greenhouse, heat-loving species at 20° to 35° C., and species from moderate climates at 10° to 25° C. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

The plants used in the greenhouse experiments were *Chenopodium album, Chrysanthemum coronarium, Euphorbia heterophylla, Galium aparine, Triticum aestivum, Hordeum vulgare, Polygonum persicaria, Sinapis alba, Matricaria inodora*, Ipomoea spp. and *Zea mays*.

Active ingredients nos. 1.025, 2.003, 3.014, 3.019, 3.031 and 3.032, applied postemergence at rates of 0.5 and 1.0 kg/ha, provide excellent control of unwanted broadleaved plants. Active ingredients nos. 1.025 and 3.014 are also well tolerated by wheat.

We claim:
1. A carboxamide of the formulae Ia, Ib and Ic

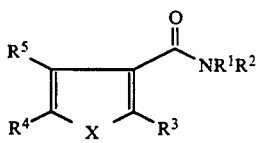

Ia

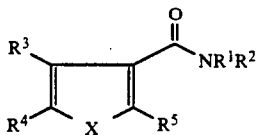

Ib

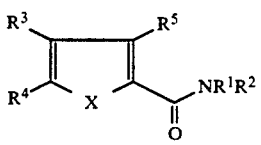

Ic where:
X is oxygen;
$R^1$ is hydrogen;
$C_3$–$C_8$-cycloalkyl which may carry from one to three of the following radicals: halogen, $C_1$–$C_4$-alkyl, $C_1$–$C_4$-haloalkyl, $C_1$–$C_4$-alkoxy and/or $C_1$–$C_4$-haloalkoxy;
$C_1$–$C_6$-alkyl which may carry from one to three of the following radicals: hydroxyl, halogen, $C_3$–$C_8$-cycloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylamino, di-$C_1$–$C_4$-alkylamino and/or $C_3$–$C_6$-cycloalkylamino and/or a radical

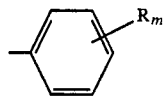

where
R is cyano; nitro; halogen; $C_1$–$C_4$-alkyl; $C_1$–$C_4$-haloalkyl; $C_1$–$C_4$-alkoxy; $C_1$–$C_4$-haloalkoxy; $C_2$–$C_4$-alkynyloxy; $C_1$–$C_4$-alkylthio; $C_1$–$C_4$-haloalkylthio; $C_3$–$C_6$-alkoxycarbonylalkoxy and/or $C_1$–$C_4$-alkoxycarbonyl and
m is 0, 1, 2 or 3, and the radicals R may be different when m is 2 or 3;
$R^2$ is hydroxy; $C_1$–$C_4$-alkoxy; $C_2$–$C_6$-cyanoalkyl; $C_3$–$C_6$-alkenyl, $C_3$–$C_6$-alkynyl, phenyl or naphthyl, where these groups may carry from one to three of the radicals stated for R;
a 5- or 6-membered heterocyclic structure containing one or two heteroatoms selected from the group consisting of 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 4-pyrrolyl, 3-pyrazolyl, 4-pyrazolyl, 5-pyrazolyl, 2-pyridyl, 3-pyridyl, 4-pyridyl and 2-(4,6-dimethylprimidinyl), where this ring may carry one or two of the following radicals: halogen, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;
one of the organic groups stated for $R^1$ or
$R^1$ and $R^2$ and the N-atom to which they are attached form a 4- to 7-membered ring which, in addition to methylene groups, may contain one of the following groups as a ring member: oxygen, sulfur, N-methyl or carbonyl;
$R^3$ and $R^4$ are each nitro; cyano; halogen;
amino which carries one or two $C_1$–$C_4$-alkyl groups and/or a $C_1$–$C_4$-alkylcarbonyl group;
$C_1$–$C_4$-alkoxy or $C_1$–$C_4$-alkylthio, where these groups may carry from one to nine halogen atoms;
a 5- or 6-membered heterocyclic structure containing one or two heteroatoms selected from the group consisting of 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 4-pyrrolyl, 3-pyrazolyl, 4-pyrazolyl, 5-pyrazolyl, 2-pyridyl, 3-pyridyl, 4-pyridyl and 2-(4,6-dimethylprimidinyl), where this ring may carry one or two of the following radicals: halogen, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;
$C_2$–$C_6$-alkenyl, $C_2$–$C_6$-alkynyl, phenyl, phenoxy or phenylthio, were these groups may carry from one to three of the radicals stated for R, or
one of the groups stated for $R^1$;
$R^5$ is formyl, 4,5-dihydrooxazol-2-yl or a group $COYR^6$;
Y is oxygen or sulfur;
$R^6$ is hydrogen;
$C_3$–$C_8$-cycloalkyl;
$C_1$–$C_6$-alkyl which may carry from one to five halogen atoms or hydroxyl groups and/or one of the following radicals: cyano, aminocarbonyl, carboxyl, trimethylsilyl, $C_1$–$C_4$-alkoxy, $C_1$–$C_4$-alkoxy-$C_1$–$C_4$-alkoxy, $C_1$–$C_4$-alkylthio, $C_1$–$C_4$-alkylamino, di-$C_1$–$C_4$-alkylamino, $C_1$–$C_4$-alkylsulfinyl, $C_1$–$C_4$-alkylsulfonyl, $C_1$–$C_4$-alkoxycarbonyl, $C_2$–$C_4$-alkoxycarbonyl-$C_1$–$C_3$-alkoxy, $C_2$–$C_4$-alkoxycarbonyl-$C_1$–$C_5$-alkoxycarbonyl, $C_1$–$C_4$-alkylaminocarbonyl, di-$C_1$–$C_4$-alkylaminocarbonyl, di-$C_1$–$C_4$-alkylphosphonyl, $C_1$–$C_4$-alkyliminoxy, phenyl, thienyl, benzyloxy, benzylthio, furyl, tetrahydrofuryl, phthalimido, pyridyl and/or benzoyl, where the cyclic radicals in turn may carry from one to three of the radicals stated for R;
$C_3$–$C_6$-alkenyl, $C_3$–$C_6$-alkynyl or $C_5$–$C_7$-cycloalkenyl, where these groups may carry one of the following radicals: hydroxy, halogen, $C_1$–$C_4$-alkoxy or phenyl, and the phenyl radical in turn may carry from one to three of the radicals stated for R;
phthalimido; tetrahydrophthalimido; succinimido; maleimido; benzotriazolyl;

phenyl which may carry from one to three of the radicals stated for R;

a group —N=CR$^7$R$^8$, where

R$^7$ is hydrogen or C$_1$–C$_6$-alkyl and

R$^8$ is C$_3$–C$_6$-cycloalkyl, phenyl, furyl or a radical R$^7$ or

R$^7$ and R$^8$ and the C-atom to which they are attached form a 4- to 7-membered alkylene ring, and if R$^5$ is carboxyl, methoxycarbonyl or ethoxycarbonyl and R$^2$ is hydrogen, R$^3$ is not hydrogen and R$^4$ is not hydrogen or methyl, and if R$^5$ is carboxyl, methoxycarbonyl or ethoxycarbonyl and R$^4$ is hydrogen, R$^3$ is not hydrogen and R$^2$ is not one of the following groups: hydrogen; C$_1$–C$_4$-alkyl; phenyl; 2-(3,4-dimethoxyphenyl)ethyl or 2,5-dichlorothien-3-yl, and their agriculturally suitable salts.

2. A process for combating the growth of unwanted plants, wherein the unwanted plants and/or their habitat are treated with a herbicidally effective amount of a carboxamide Ia, Ib or Ic as set forth in claim 1.

3. A herbicidal composition comprising conventional inert additives and a herbicidally effective amount of at least one carboxamide of the formula Ia, Ib, or Ic as set forth in claim 1.

* * * * *

UNITED STATES PATENT AND TRADEMARK OFFICE
CERTIFICATE OF CORRECTION

PATENT NO. : 5,258,357
DATED : Nov. 2, 1993
INVENTOR(S) : MUENSTER et al.

It is certified that error appears in the above-identified patent and that said Letters Patent is hereby corrected as shown below:

ON THE TITLE PAGE

Item [63], delete "Continuation" and insert -- Divisional--.

Signed and Sealed this

Tenth Day of May, 1994

Attest:

BRUCE LEHMAN

Attesting Officer

Commissioner of Patents and Trademarks